(12) United States Patent
Hu et al.

(10) Patent No.: US 11,672,174 B2
(45) Date of Patent: Jun. 6, 2023

(54) PYRENE-TRIAZINE DERIVATIVE AND APPLICATIONS THEREOF IN ORGANIC ELECTRONIC COMPONENT

(71) Applicant: GUANGZHOU CHINARAY OPTOELECTRONIC MATERIALS LTD., Guangdong (CN)

(72) Inventors: Guang Hu, Guangdong (CN); Xi Yang, Guangdong (CN); Junyou Pan, Guangdong (CN)

(73) Assignee: GUANGZHOU CHINARAY OPTOELECTRONIC MATERIALS LTD., Guangdong (CN)

( * ) Notice: Subject to any disclaimer, the term of this patent is extended or adjusted under 35 U.S.C. 154(b) by 918 days.

(21) Appl. No.: 16/467,423

(22) PCT Filed: Dec. 8, 2017

(86) PCT No.: PCT/CN2017/115312
§ 371 (c)(1),
(2) Date: Jun. 6, 2019

(87) PCT Pub. No.: WO2018/103748
PCT Pub. Date: Jun. 14, 2018

(65) Prior Publication Data
US 2019/0334093 A1 Oct. 31, 2019

(30) Foreign Application Priority Data
Dec. 8, 2016 (CN) .......................... 201611124123.1

(51) Int. Cl.
*H01L 51/54* (2006.01)
*H01L 51/00* (2006.01)
*H01L 51/50* (2006.01)
*C07D 251/22* (2006.01)
*C07D 251/24* (2006.01)

(52) U.S. Cl.
CPC ...... *H01L 51/0069* (2013.01); *H01L 51/0054* (2013.01); *H01L 51/0067* (2013.01); *H01L 51/0072* (2013.01); *H01L 51/0073* (2013.01); *H01L 51/0074* (2013.01); *H01L 51/5004* (2013.01); *H01L 51/5072* (2013.01); *C07D 251/22* (2013.01); *C07D 251/24* (2013.01); *H01L 51/5016* (2013.01); *H01L 2251/552* (2013.01)

(58) Field of Classification Search
None
See application file for complete search history.

(56) References Cited

U.S. PATENT DOCUMENTS

| 4,769,292 | A | 9/1988 | Tang et al. |
| 5,121,029 | A | 6/1992 | Hosokawa et al. |
| 5,130,603 | A | 7/1992 | Tokailin et al. |
| 6,020,078 | A | 2/2000 | Chen et al. |
| 6,251,531 | B1 | 6/2001 | Enokida et al. |
| 7,250,532 | B2 | 7/2007 | Iwakuma et al. |
| 8,785,001 | B2 | 7/2014 | Vestweber et al. |
| 9,660,198 | B2 | 5/2017 | Nakagawa et al. |
| 9,660,199 | B2 | 5/2017 | Shizu et al. |
| 9,882,146 | B2 | 1/2018 | Lee et al. |
| 10,454,038 | B2 | 10/2019 | Nakagawa et al. |
| 2006/0210830 | A1 | 9/2006 | Funahashi et al. |
| 2006/0222886 | A1 | 10/2006 | Kwong et al. |
| 2007/0252517 | A1 | 11/2007 | Owczarczyk et al. |
| 2008/0105865 | A1* | 5/2008 | Oyamada ............... C07F 7/0805 549/462 |
| 2008/0113101 | A1 | 5/2008 | Inoue et al. |
| 2009/0134784 | A1 | 5/2009 | Lin et al. |
| 2011/0240983 | A1* | 10/2011 | Sekiguchi ............. H05B 33/14 257/40 |
| 2012/0217869 | A1 | 8/2012 | Adachi et al. |
| 2014/0197381 | A1 | 7/2014 | Kim et al. |
| 2014/0203252 | A1* | 7/2014 | Kitamura .............. H05B 33/10 544/333 |
| 2015/0141642 | A1 | 5/2015 | Adachi et al. |
| 2015/0318508 | A1 | 11/2015 | Kim et al. |

FOREIGN PATENT DOCUMENTS

| CN | 1583691 A | 2/2005 |
| CN | 101003508 A | 7/2007 |
| CN | 101003508 B | 11/2010 |
| CN | 103165818 A | 6/2013 |

(Continued)

OTHER PUBLICATIONS

Machine translation of WO-2013009095-A1. (Year: 2013).*
PCT/CN2017/115312, "International Search Report", dated Feb. 26, 2018, 2 pages.
Office Action and Supplementary Search Report for Chinese Patent Application No. 201780059471.1, dated Nov. 11, 2021, 14 pages.
Endo et al., "Thermally Activated Delayed Fluorescence from $Sn^{4+}$-Porphyrin Complexes and Their Application to Organic Light-Emitting Diodes—A Novel Mechanism for Electroluminescence", Advanced Materials, vol. 21, 2009, pp. 4802-4806.
Li et al., Highly Efficient Organic Light-Emitting Diode Based on a Hidden Thermally Activated Delayed Fluorescence Channel in a Heptazine Derivative, Advanced Materials, vol. 25, 2013, pp. 1-5.
Dias et al., "Triplet Harvesting with 100% Efficiency by Way of Thermally Activated Delayed Fluorescence in Charge Transfer OLEO Emitters", Advanced Materials, vol. 25, 2013, pp. 3707-3714.

(Continued)

*Primary Examiner* — Andrew K Bohaty
(74) *Attorney, Agent, or Firm* — PV IP PC; Wei Te Chung; Zhigang Ma

(57) ABSTRACT

A pyrene-triazine compound, a mixture containing same, a formulation, an organic electronic component, and applications. The pyrene-triazine compound comprises a triazine structure of three strong electron affinity nitrogen atoms and a pyrene fused ring structure. Because the triazine structure has great optoelectronic performance and a planar structured pyrene derivative has great carrier transport performance and optoelectronic performance, the application of the pyrene-triazine compound in the organic electronic component produces a light-emitting component having high efficiency and an extended service life.

9 Claims, No Drawings

(56) References Cited

FOREIGN PATENT DOCUMENTS

| | | | |
|---|---|---|---|
| CN | 104203941 A | 12/2014 | |
| CN | 103570629 B | 10/2015 | |
| CN | 103483332 B | 8/2016 | |
| DE | 102005058557 A1 | 6/2007 | |
| EP | 1957606 A1 | 8/2008 | |
| JP | H08-53397 A | 2/1996 | |
| JP | 2913116 B2 | 6/1999 | |
| KR | 20150026055 A | 3/2015 | |
| TW | 201309696 A | 3/2013 | |
| TW | 201309778 A | 3/2013 | |
| TW | 201343874 A | 11/2013 | |
| TW | 201350558 A | 12/2013 | |
| WO | 2001021729 A1 | 3/2001 | |
| WO | 2006000388 A1 | 1/2006 | |
| WO | 2006000389 A1 | 1/2006 | |
| WO | 2006058737 A1 | 6/2006 | |
| WO | 2006122630 A1 | 11/2006 | |
| WO | 2007065549 A1 | 6/2007 | |
| WO | 2007115610 A1 | 10/2007 | |
| WO | 2007140847 A1 | 12/2007 | |
| WO | 2008006449 A1 | 1/2008 | |
| WO | 2010067894 A1 | 6/2010 | |
| WO | 2010135519 A1 | 11/2010 | |
| WO | 2011110277 A1 | 9/2011 | |
| WO | WO-2013009095 A1 * | 1/2013 | ............ C07C 51/00 |
| WO | 2011141110 A3 | 5/2013 | |
| WO | 2013133359 A1 | 9/2013 | |
| WO | 2013154064 A1 | 10/2013 | |

OTHER PUBLICATIONS

Mehes et al., "Enhanced Electroluminescence Efficiency in a Spiro-Acridine Derivative through Thermally Activated Delayed Fluorescence", Angew. Chem. Int. Ed., vol. 51, 2012, pp. 11311-11315.

Endo et al., "Efficient up-conversion of triplet excitons into a singlet state and its application for organic light emitting diodes", Applied Physics Letters, vol. 98, 2011, pp. 083302-1-083302-3.

Lee et al., "High-efficiency organic light-emitting diodes utilizing thermally activated delayed fluorescence from triazine-based donor-acceptor hybrid molecules", Applied Physics Letters, vol. 101, 2012, pp. 093306-1-093306-4.

Nakagawa et al., "Electroluminescence based on thermally activated delayed fluorescence generated by a spirobifluorene donor-acceptor structure" Chem. Commun., vol. 48, 2012, pp. 9580-9582.

Tanaka et al., "Efficient green thermally activated delayed fluorescence (TADF) from a phenoxazine-triphenyltriazine (PXZ-TRZ) derivative", Chem. Commun., vol. 48, 2012, pp. 11392-11394.

Nasu et al., "A highly luminescent spiro-anthracenone-based organic light-emitting diode exhibiting thermally activated delayed fluorescence", Chem Commun, vol. 48, 2013, pp. 1-3.

Komino et al., "Suppression of Efficiency Roll-Off Characteristics in Thermally Activated Delayed Fluorescence Based Organic Light-Emitting Diodes Using Randomly Oriented Host Molecules", Chemistry of Materials, vol. 25, 2013, pp. 3038-3047.

Tanaka et al., "Twisted Intramolecular Charge Transfer State for Long-Wavelength Thermally Activated Delayed Fluorescence", Chemistry of Materials, vol. 25, 2013, pp. 3766-3771.

Zhang et al., "Design of Efficient Thermally Activated Delayed Fluorescence Materials for Pure Blue Organic Light Emitting Diodes", J. Am. Chem. Soc., vol. 134, 2012, pp. 14706-14709.

Lee et al., "Oxadiazole- and triazole-based highly-efficient thermally activated delayed fluorescence emitters for organic light-emitting diodes", Journal of Materials Chemistry C, vol. 1, 2013, pp. 1-6.

Ishimatsu et al., "Solvent Effect on Thermally Activated Delayed Fluorescence by 1,2,3,5-Tetrakis(carbazol-9-yl)-4,6-dicyanobenzene", The Journal Physical Chemistry A, vol. 117, 2013, pp. 5607-5612.

Goushi et al., "Organic light-emitting diodes employing efficient reverse intersystem crossing for triplet-to-singlet state conversion", Nature Photonics, vol. 6, Apr. 2012, pp. 253-258.

Uoyama et al., "Highly efficient organic light-emitting diodes from delayed fluorescence", Nature, vol. 492, Dec. 13, 2012, pp. 234-238.

Kipphan (Handbook of Print Media: Technologies and Production Methods), ISBN 3-540-67326-1, Chapter 1.3, pp. 40-67, Chapter 1.5, pp. 117-144, Chapter 5.5, pp. 711-730.

Newkome, et al., Dendrimers and Dendrons, Wiley-VCH Verlag GmbH & Co. KGaA, 2002, pp. 1-21, 51-76, 76-102, 102-118, 191-234, 234-282, 282-309, 331-365, 366-393, 395-431, 431-455.

Tang et al., "Organic electroluminescent diodes" Applied Physics Letters, vol. 51, No. 12, Sep. 21, 1987, pp. 913-915.

Bulovic et al. "Transparent light-emitting devices", Nature, vol. 380, Mar. 7, 1996, p. 29.

Gu et al., "Transparent organic light emitting devices" Applied Physics Letters, vol. 68, No. 19, May 6, 1996, pp. 2606-2608.

* cited by examiner

PYRENE-TRIAZINE DERIVATIVE AND APPLICATIONS THEREOF IN ORGANIC ELECTRONIC COMPONENT

CROSS-REFERENCE TO RELATED APPLICATIONS

The present application is a national stage for International Application PCT/CN2017/115312, filed on Dec. 8, 2017, which claims priority benefit of Chinese Patent Application No. 201611124123.1 filed on Dec. 8, 2016, and entitled "PYRENE-TRIAZINE DERIVATIVE AND APPLICATIONS THEREOF IN ORGANIC ELECTRONIC COMPONENT", the entire contents of both applications are incorporated herein for all purposes.

TECHNICAL FIELD

The present disclosure relates to a pyrene-triazine compound, a formulation and a mixture comprising the pyrene-triazine compound, and application thereof in organic electronic devices.

BACKGROUND

Organic semiconductor materials have great application potential in many photoelectric apparatuses, such as an organic light-emitting diode (OLED), an organic photovoltaic cell (OPV), an organic field effect transistor (OFET), due to properties of the organic semiconductor materials such as the diversity of molecular structure design, relatively low manufacturing cost, and superior optoelectronic performance, etc. Especially, since Tang et al. (C. W. Tang and S. A. Van Slyke, Appl. Phys. Lett., 1987, 51, 913) reported the double-layer OLED structure in 1987, the organic semiconductor materials have developed rapidly in the fields for display and lighting.

The organic thin film light-emitting element must satisfy the requirements of improvement in luminous efficiency, reduction in driving voltage and improvement in durability, etc. However, currently there are still many technical challenges, especially the coexistence of high efficiency and long lifetime of the element.

In order to accelerate the process of promoting the large-scale industrialization of OLED and improve its photoelectric performance, various novel organic photoelectric materials have been developed. Organic semiconductor materials of triazines containing three strong electron-accepting nitrogen atoms have wide applications in optoelectronic devices due to their superior optoelectronic performance. In addition, pyrene derivatives with planar structures generally have good carrier transport performance and optoelectronic performance.

CN 104203941 A discloses a class of compounds in which a triazine unit is linked to a phenyl group, or a phenanthrene group, or a benzothiophene group, or a fluorenyl group, and the like. Such compounds are used as electron transport layers for blue OLED devices, so that the voltage of the device is reduced and the efficiency is improved. CN 101003508 B discloses a class of pyrene compounds characterized in that the two groups directly linked to the pyrenyl group are aromatic groups which must not contain a heteroatom. Such compounds are used as electron transport layers for OLED devices, so that the performance of the device is improved to an extent. CN 103570629 B discloses a class of compounds in which a benzanthryl group is linked to a triazine. Such compounds are used as electron transport layers for blue OLED devices, so that the voltage of the device is reduced. US 2015318508 A discloses a class of compounds in which an anthryl group or a benzophenanthryl group is linked to a triazine. Such compounds are used as electron transport layers for OLED devices, so that the voltage of the device is reduced and the efficiency is also improved.

However, all currently reported organic semiconductor materials of triazines or having pyrene fused ring structures have certain limitations in carrier transport capability, stability, lifetime, and the like in photovoltaic devices. However, when all such compounds are used in OLEDs, the overall performance thereof, especially lifetime, still needs to be improved.

In addition, large planar conjugated pyrene fused ring structures with high electron mobility and photoelectric efficiency, have not been disclosed, and may lead to higher efficiency and longer lifetime in conjugation with triazines. In order to further explore the photoelectric performance of such materials, the material with a new structure conjugating triazine with pyrene fused ring is still to be designed and developed.

In addition, in order to reduce the production costs and realize the large-area OLED devices, printing OLED is becoming one of the most promising technology options. In this regard, printing OLED materials are the key point. However, the current developed small-molecule OLED materials for evaporation technology have poor solubility and film-forming performance due to their lower molecular weight and rigid aromatic molecular structure. Particularly, it is difficult to form a non-hollow amorphous film with a regular appearance. Therefore, currently there is no corresponding material solution to the problem of printing OLEDs, and small molecule organic light-emitting diodes with high performance are still prepared by vacuum evaporation. Therefore, designing and synthesizing organic small-molecule functional compounds with good solubility and film-forming performance is especially important for realizing the high-performance solution-processing organic light-emitting diodes.

SUMMARY

In view of the above deficiencies of the prior art, the object of the present disclosure is to provide a class of novel organic optoelectronic materials, in particular a triazine-pyrene fused ring compound, a mixture and a formulation containing the triazine-pyrene fused ring compound, and application thereof in organic electronic devices, aimed to reduce driving voltage, improve luminous efficiency, stability and lifetime of devices, and provide a material solution for printing the OLED at the same time.

A technical solution of the present disclosure is described below.

A triazine fused ring compound as represented by following general formula (1):

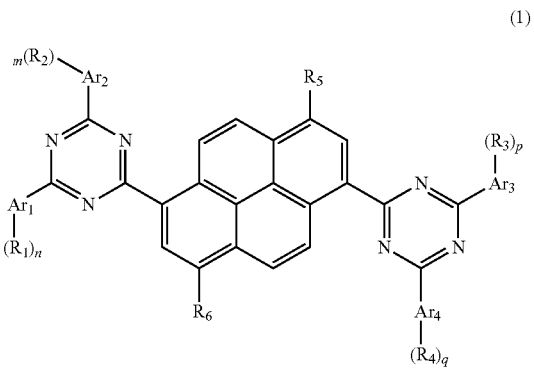

(1)

wherein $Ar_1$, $Ar_2$, $Ar_3$, and $Ar_4$ are aromatic groups containing 6 to 60 carbon atoms or heterocyclic aromatic groups containing 3 to 60 carbon atoms, and the heterocyclic aromatic group includes N, O, and S;

at least one of $Ar_1$ to $Ar_4$ is a heterocyclic aromatic group having a nitrogen atom;

$R_1$ to $R_6$ are selected from the group consisting of H, D, F, —CN, —$NO_2$, —$CF_3$, alkenyl, alkynyl, amino, acyl, amide group, cyano, isocyano, alkoxy, hydroxy, carbonyl, sulfonyl, an alkyl group containing 1 to 60 carbon atoms, a cycloalkyl group containing 3 to 60 carbon atoms, an aromatic group containing 6 to 60 carbon atoms, a heterocyclic aromatic group containing 3 to 60 carbon atoms, a fused ring aromatic group containing 7 to 60 carbon atoms, and a fused heterocyclic aromatic group containing 4 to 60 carbon atoms, or $R_1$ to $R_6$ form a monocyclic or polycyclic aliphatic or aromatic ring system with each other; and m, n, p, and q are integers from 1 to 20.

In one embodiment, at least one of $Ar_1$, $Ar_2$, $Ar_3$, and $Ar_4$ comprises the following structures Ts:

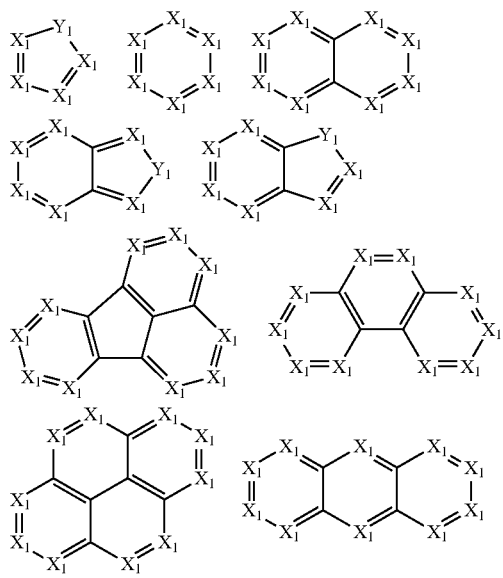

wherein, $X_1$ is $CR_7$ or N, at least one of $X_1$s in the structures Ts is N, and two adjacent $X_1$s are not simultaneously N;

$Y_1$ is selected from the group consisting of $CR_8R_9$, $SiR_{10}R_{11}$, $NR_{12}$, C(=O), S(=O)$_2$, O, and S; and $R_7$ to $R_{12}$ selected from the group consisting of H, D, F, —CN, —$NO_2$, —$CF_3$, alkenyl, alkynyl, amino, acyl, amide group, cyano, isocyano, alkoxy, hydroxy, carbonyl, sulfonyl, an alkyl group containing 1 to 60 carbon atoms, a cycloalkyl group containing 3 to 60 carbon atoms, an aromatic group containing 6 to 60 carbon atoms, a heterocyclic aromatic group containing 3 to 60 carbon atoms, a fused ring aromatic group containing 7 to 60 carbon atoms, and a fused heterocyclic aromatic group containing 4 to 60 carbon atoms.

A polymer comprises at least one repeating structural unit of the pyrene-triazine compound as represented by the general formula (1).

A mixture comprises the pyrene-triazine compound or the polymer and at least one organic functional material, the organic functional material is selected from a hole injection material, a hole transport material, a hole blocking material, an electron injection material, an electron transport material, an electron blocking material, a light-emitting host material, a fluorescent emitter, a phosphorescent emitter, a thermally activated delayed fluorescent material or an organic dye.

A formulation comprises at least one of the pyrene-triazine compound or the polymer as described above, and at least one organic solvent.

An organic electronic device comprises at least one of the pyrene-triazine compound or the polymer as described above, or is prepared by the mixture as described above. The organic electronic device may be an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, an organic sensor, or an organic plasmon emitting diode.

A method for preparing a functional layer containing the pyrene-triazine compound, comprises: forming a functional layer on a substrate by evaporation of the pyrene-triazine compound described above; or forming a functional layer on a substrate by co-evaporation of the pyrene-triazine compound together with the an organic functional material; or forming a functional layer by coating the formulation described above on a substrate via printing or coating. The printing or coating method can be selected from, but not limited to, inkjet printing, nozzle printing, letterpress printing, screen printing, dip coating, spin coating, blade coating, roller printing, torsion roll printing, lithography, flexographic printing, rotary printing, spray coating, brush coating or pad printing, slot die coating, etc.

The pyrene-triazine compound of the present disclosure comprises a triazine structure containing three strong electron-accepting nitrogen atoms, and a pyrene fused ring structure. The triazine structure has superior photoelectric performance, and the pyrene derivative with planar structure has good carrier transport performance and photoelectric performance. Therefore, the conjugation of triazine with the pyrene fused ring in the pyrene-triazine compound is beneficial to achieve better carrier transport and photoelectric response, better energy level matching, and improve the photoelectric performance and the stability of such compound. Therefore, the light-emitting device with high manufacturing efficiency and long lifetime can finally be obtained by a polymer polymerizing the pyrene-triazine compound, a mixture and a formulation containing the pyrene-triazine compound and polymer thereof, and the organic electronic device thereof.

DETAILED DESCRIPTION OF THE DISCLOSURE

The present disclosure provides a class of novel organic photoelectric materials and application thereof in organic electronic devices. In order to make the purpose, technical solution and effects of the present disclosure clearer and more specific, the present disclosure will be furthermore described in detail below. It should be noted that, the specific embodiment illustrated herein is merely for the purpose of explanation, and should not be deemed to limit the present disclosure.

In the present disclosure, formulation and printing ink, or ink, have the same meaning and they can be used interchangeably.

In the present disclosure, the host material or the matrix material, Host or Matrix have the same meaning and they are interchangeable.

In the present disclosure, the metal organic clathrate, the metal organic complexes, and organometallic complexes have the same meaning and are interchangeable.

According to the pyrene-triazine compound of the present disclosure, the concepts of aromatic and heteroaromatic will be involved for many times, and are specifically defined as follows:

The aromatic group refers to a hydrocarbyl containing at least one aromatic ring. The heterocyclic aromatic group refers to an aromatic hydrocarbyl containing at least one heteroatom. The fused ring aromatic group refers to an aromatic group whose ring may have two or more rings, wherein two carbon atoms are shared by two adjacent rings, i.e., fused ring. The fused heterocyclic aromatic group refers to a fused ring aromatic hydrocarbyl containing at least one heteroatom. For the purposes of the present disclosure, the aromatic group includes a fused ring aromatic group, and the heterocyclic aromatic group includes a fused heterocyclic aromatic group. For the purposes of the present disclosure, the aromatic group or the heterocyclic aromatic group includes not only an aromatic ring system but also a non-aromatic ring system. Therefore, systems such as pyridine, thiophene, pyrrole, pyrazole, triazole, imidazole, oxazole, oxadiazole, thiazole, tetrazole, pyrazine, pyridazine, pyrimidine, triazine, carbene, etc., are also considered to be an aromatic group or a heterocyclic aromatic group, for the purpose of the disclosure. For the purpose of the present disclosure, the fused aromatic or heteroaromatic ring systems not only include aromatic or heteroaromatic systems, but also have a plurality of aryl groups or heteroaryl groups spaced by short non-aromatic units (<10% of non-H atoms, preferably less than 5% of non-H atoms, such as C, N or O atoms). Therefore, systems such as 9,9'-spirobifluorene, 9,9-diarylfluorene, triarylamine, diaryl ether and the like are also considered to be fused aromatic ring systems for the purpose of this disclosure.

Specifically, examples of the aromatic group include: benzene, biphenyl, terphenyl, toluene, chlorobenzene, and derivatives thereof.

Specifically, examples of the fused ring aromatic group include: naphthalene, anthracene, fluoranthene, phenanthrene, benzophenanthrene, perylene, tetracene, pyrene, benzopyrene, acenaphthene, fluorene, and derivatives thereof.

Specifically, examples of heterocyclic aromatic group are: pyridine, thiophene, pyrrole, pyrazole, triazole, imidazole, oxazole, oxadiazole, thiazole, tetrazole, pyrazine, pyridazine, pyrimidine, triazine, carbene, and derivatives thereof.

Specifically, examples of the fused heterocyclic aromatic group include: benzofuran, benzothiophene, indole, carbazole, pyrroloimidazole, pyrrolopyrrole, thienopyrrole, thienothiophene, furopyrrole, furofuran, thienofuran, benzisoxazole, benzisothiazole, benzimidazole, quinoline, isoquinoline, cinnoline, quinoxaline, phenanthridine, perimidine, quinazoline, quinazolinone, and derivatives thereof.

The present disclosure provides a pyrene-triazine compound as represented by general formula (1), in which the symbols and labels used have the following meanings:

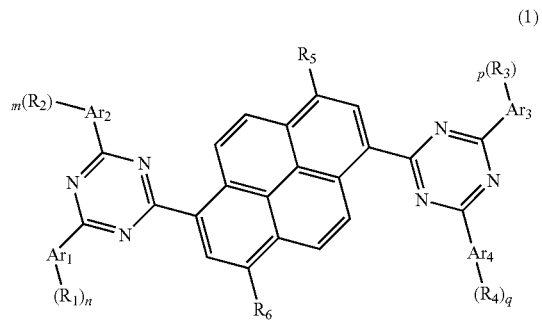

(1)

wherein, $Ar_1$, $Ar_2$, $Ar_3$, and $Ar_4$ are the same or different and are each independently selected from the group consisting of a substituted or unsubstituted aromatic group containing 6 to 60 carbon atoms, and a substituted or unsubstituted heterocyclic aromatic group containing 3 to 60 carbon atoms, and at least one group of $Ar_1$ to $Ar_4$ is a heterocyclic aromatic group having a nitrogen atom;

one or more positions on $Ar_1$ are substituted or unsubstituted by one or more groups $R_1$, and the group $R_1$ may be the same or different in multiple occurrences;

one or more positions on $Ar_2$ are substituted or unsubstituted by one or more groups $R_2$, and the group $R_2$ may be the same or different in multiple occurrences;

one or more positions on $Ar_3$ are substituted or unsubstituted by one or more groups $R_3$, and the group $R_3$ may be the same or different in multiple occurrences;

one or more positions on $Ar_4$ are substituted or unsubstituted by one or more groups $R_4$, and the group $R_4$ may be the same or different in multiple occurrences;

$R_1$ to $R_6$ are the same or different in multiple occurrences, and may be selected from the group consisting of H, D, F, —CN, —NO$_2$, —CF$_3$, alkenyl, alkynyl, amino, acyl, amide group, cyano, isocyano, alkoxy, hydroxy, carbonyl, sulfonyl, a substituted or unsubstituted alkyl containing 1 to 60 carbon atoms, a substituted or unsubstituted cycloalkyl containing 3 to 60 carbon atoms, a substituted or unsubstituted aromatic group containing 6 to 60 carbon atoms, a substituted or unsubstituted heterocyclic aromatic group containing 3 to 60 carbon atoms, a substituted or unsubstituted fused ring aromatic group containing 7 to 60 carbon atoms, and a fused heterocyclic aromatic group containing 4 to 60 carbon atoms, or one or more of the groups may form a monocyclic or polycyclic aliphatic or aromatic ring system with each other and/or with a ring bonded to the groups.

m is an integer from 0 to 20, further, m is an integer from 0 to 10, still further, m is an integer from 0 to 5, and even further, m is an integer from 0 to 3.

n is an integer from 0 to 20, further, n is an integer from 0 to 10, still further, n is an integer from 0 to 5, and even further, n is an integer from 0 to 3.

p is an integer from 0 to 20, further, p is an integer from 0 to 10, still further, p is an integer from 0 to 5, and even further, p is an integer from 0 to 3.

q is an integer from 0 to 20, further, q is an integer from 0 to 10, still further, q is an integer from 0 to 5, and even further, q is an integer from 0 to 3.

In some embodiments, $Ar_1$, $Ar_2$, $Ar_3$, and $Ar_4$ are each independently selected from the group consisting of a substituted or unsubstituted aromatic group containing 6 to 40 carbon atoms, and a substituted or unsubstituted heterocyclic aromatic group containing 3 to 40 carbon atoms, and at least one group of $Ar_1$ to $Ar_4$ is a heterocyclic aromatic group having a nitrogen atom; in a further embodiment, $Ar_1$, $Ar_2$, $Ar_3$, and $Ar_4$ are each independently selected from the group consisting of a substituted or unsubstituted aromatic group containing 6 to 30 carbon atoms, and a substituted or unsubstituted heterocyclic aromatic group containing 3 to 30 carbon atoms, and at least one group of $Ar_1$ to $Ar_4$ is a heterocyclic aromatic group having a nitrogen atom; in the most embodiment, $Ar_1$, $Ar_2$, $Ar_3$, and $Ar_4$ are each independently selected from the group consisting of a substituted or unsubstituted aromatic group containing 6 to 20 carbon atoms, and a substituted or unsubstituted heterocyclic aromatic group containing 3 to 20 carbon atoms, and at least one group of $Ar_1$ to $Ar_4$ is a heterocyclic aromatic group having a nitrogen atom;

In some embodiments, the heteroatoms of the heteroaromatic fused ring are selected from Si, N, P, O, S and/or Ge, particularly selected from Si, N, P, O and/or S, and even more particularly selected from N, O or S.

According to the pyrene-triazine compound of the present disclosure, at least one of $Ar_1$, $Ar_2$, $Ar_3$, and $Ar_4$ is an aromatic heterocyclic ring having an N atom, and such heterocyclic ring has, but is not limited to, the following structures:

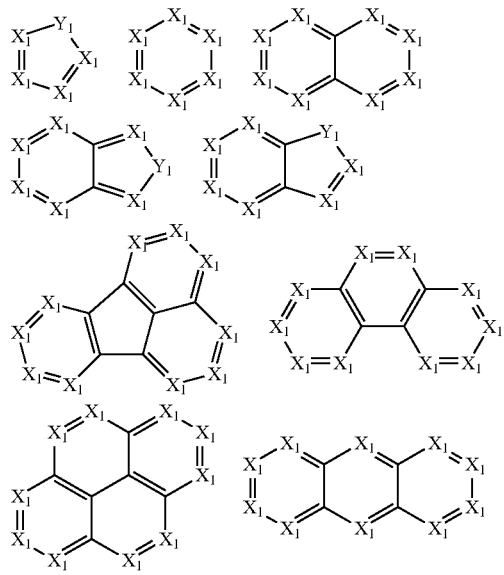

wherein $X_1$ is $CR_7$ or N, and at least one $X_1$s in each structure is N, and in one embodiment, the number of N is an integer from 1 to 6, further, the number of N is an integer from 1 to 3;

$Y_1$ is selected from the group consisting of $CR_8R_9$, $SiR_{10}R_{11}$, $NR_{12}$, $C(=O)$, $S(=O)_2$, and O, particularly selected from $CR_8R_9$, O, and S;

$R_7$ to $R_{12}$ are the same or different in multiple occurrences, and may be a linking site to other groups, or selected from the group consisting of H, D, F, —CN, —$NO_2$, —$CF_3$, alkenyl, alkynyl, amino, acyl, amide group, cyano, isocyano, alkoxy, hydroxy, carbonyl, sulfonyl, a substituted or unsubstituted alkyl containing 1 to 60 carbon atoms, a substituted or unsubstituted cycloalkyl containing 3 to 60 carbon atoms, a substituted or unsubstituted aromatic group containing 6 to 60 carbon atoms, a substituted or unsubstituted heterocyclic aromatic group containing 3 to 60 carbon atoms, a substituted or unsubstituted fused ring aromatic group containing 7 to 60 carbon atoms, and a fused heterocyclic aromatic group containing 4 to 60 carbon atoms, or one or more of the groups may form a monocyclic or polycyclic aliphatic or aromatic ring system with each other and/or with a ring bonded to the groups.

In some embodiments, $R_7$ to $R_{12}$ are the same or different in multiple occurrences, and may be a linking site to other groups, or selected from the group consisting of H, D, F, —CN, —$NO_2$, —$CF_3$, alkenyl, alkynyl, amino, acyl, amide group, cyano, isocyano, alkoxy, hydroxy, carbonyl, sulfonyl, a substituted or unsubstituted alkyl containing 1 to 30 carbon atoms, a substituted or unsubstituted cycloalkyl containing 3 to 30 carbon atoms, a substituted or unsubstituted aromatic group containing 6 to 30 carbon atoms, a substituted or unsubstituted heterocyclic aromatic group containing 3 to 30 carbon atoms, a substituted or unsubstituted fused ring aromatic group containing 7 to 30 carbon atoms, and a fused heterocyclic aromatic group containing 4 to 30 carbon atoms, or one or more of the groups may form a monocyclic or polycyclic aliphatic or aromatic ring system with each other and/or with a ring bonded to the groups.

In some embodiments, at least one of $Ar_1$, $Ar_2$, $Ar_3$, and $Ar_4$ is an aromatic heterocyclic ring having an N atom, and the aromatic heterocyclic ring is selected from the following structures:

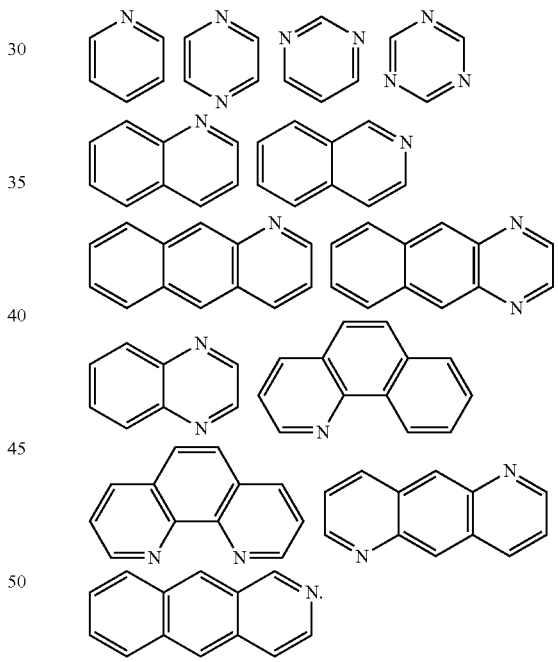

In certain embodiments, $Ar_1$ or $Ar_2$ or $Ar_3$ or $Ar_4$ in the general formula (1) is selected from the following structures:

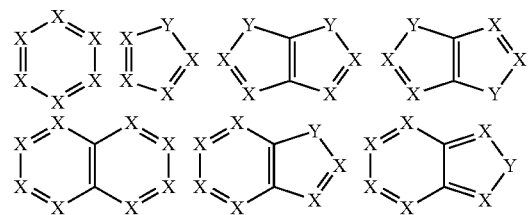

-continued
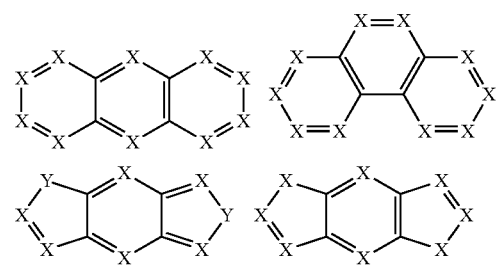
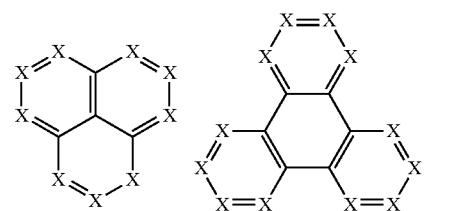
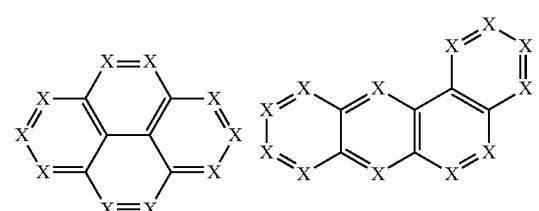
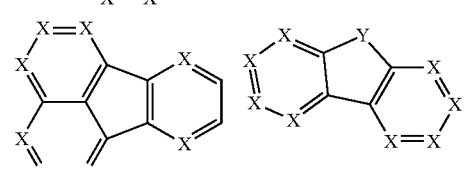
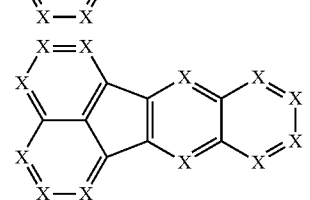
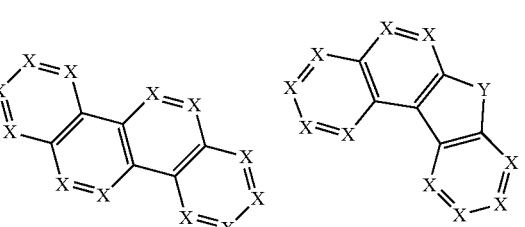
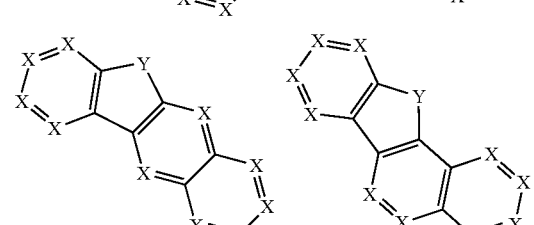
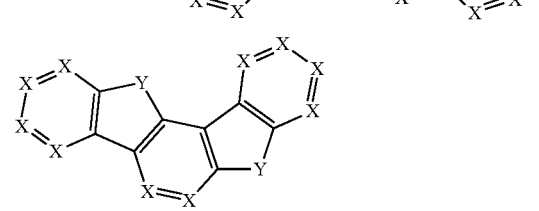
-continued
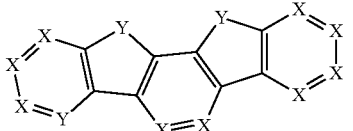
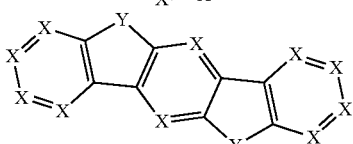
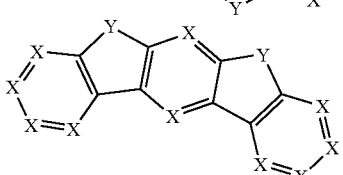
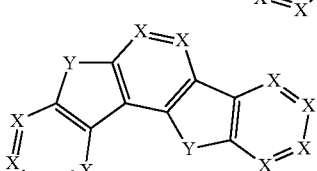
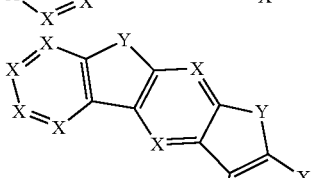
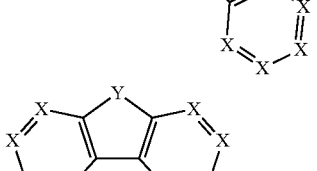
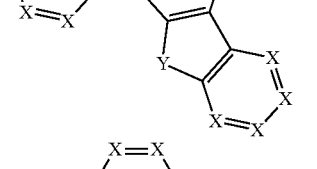
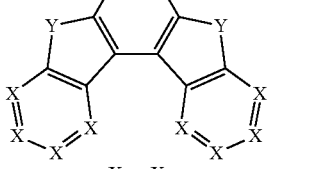
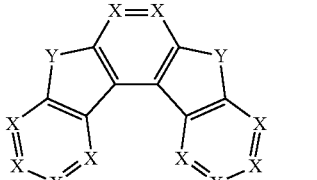
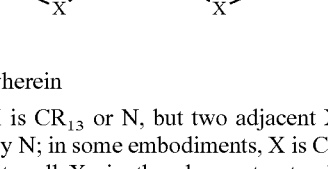
wherein
X is $CR_{13}$ or N, but two adjacent Xs are not simultaneously N; in some embodiments, X is $CR_{13}$. In some embodiments, all Xs in the above structural formulas are $CR_{13}$, wherein $R_{13}$ is H or D;
Y is selected from the group consisting of $CR_{14}R_{15}$, $SiR_{16}R_{17}$, $NR_{18}$, C(=O), S(=O)$_2$, O, and S, further, Y is $CR_{14}R_{15}$ or O;

$R_{13}$ to $R_{18}$ are the same or different in multiple occurrences, and may be a site linking to other groups, or is selected from the group consisting of H, D, F, —CN, —NO$_2$, —CF$_3$, alkenyl, alkynyl, amino, acyl, amide group, cyano, isocyano, alkoxy, hydroxy, carbonyl, sulfonyl, a substituted or unsubstituted alkyl containing 1 to 60 carbon atoms, a substituted or unsubstituted cycloalkyl containing 3 to 60 carbon atoms, a substituted or unsubstituted aromatic group containing 6 to 60 carbon atoms, a substituted or unsubstituted heterocyclic aromatic group containing 3 to 60 carbon atoms, a substituted or unsubstituted fused ring aromatic group containing 7 to 60 carbon atoms and a fused heterocyclic aromatic group containing 4 to 60 carbon atoms, or one or more of the groups may form a monocyclic or polycyclic aliphatic or aromatic ring system with each other and/or with a ring bonded to the groups.

In some embodiments, $R_{13}$ to $R_{18}$ are the same or different in multiple occurrences, and may be a linking site to other groups, or is selected from the group consisting of H, D, F, —CN, —NO$_2$, —CF$_3$, alkenyl, alkynyl, amino, acyl, amide group, cyano, isocyano, alkoxy, hydroxy, carbonyl, sulfonyl, a substituted or unsubstituted alkyl containing 1 to 30 carbon atoms, a substituted or unsubstituted cycloalkyl containing 3 to 30 carbon atoms, a substituted or unsubstituted aromatic group containing 6 to 30 carbon atoms, a substituted or unsubstituted heterocyclic aromatic group containing 3 to 30 carbon atoms, a substituted or unsubstituted fused ring aromatic group containing 7 to 30 carbon atoms and a fused heterocyclic aromatic group containing 4 to 30 carbon atoms, or one or more of the groups may form a monocyclic or polycyclic aliphatic or aromatic ring system with each other and/or with a ring bonded to the groups.

In some embodiments, suitable examples of aromatic or heteroaromatic groups which may be used as Ar$_1$-Ar$_4$ are groups independently selected from, but not limited to, anthracene, fluoranthene, phenanthrene, benzophenanthrene, perylene, tetracene, pyrene, benzopyrene, acenaphthene, fluorene, carbazole, dibenzofuran, dibenzothiophene and the like.

Further, Ar$_1$ or Ar$_2$ or Ar$_3$ or Ar$_4$ in the general formula (1) may be the same or different and contain the following structural units or a combination thereof:

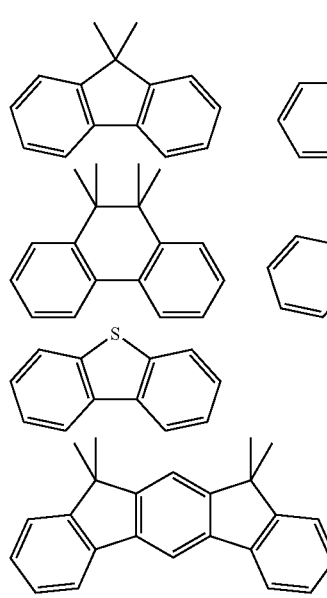

-continued

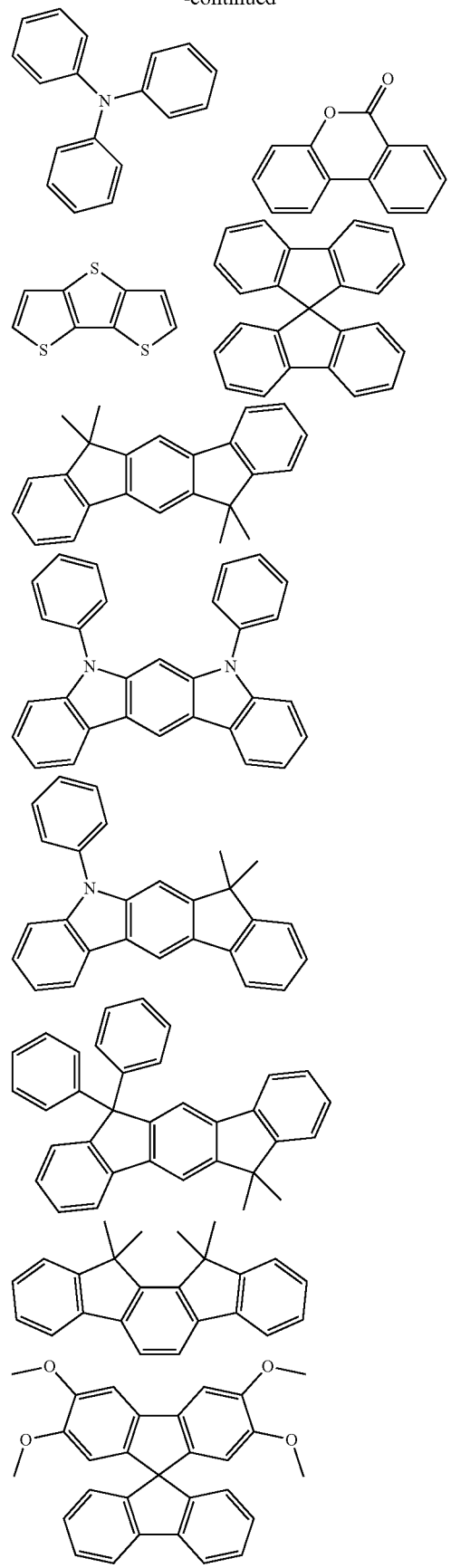

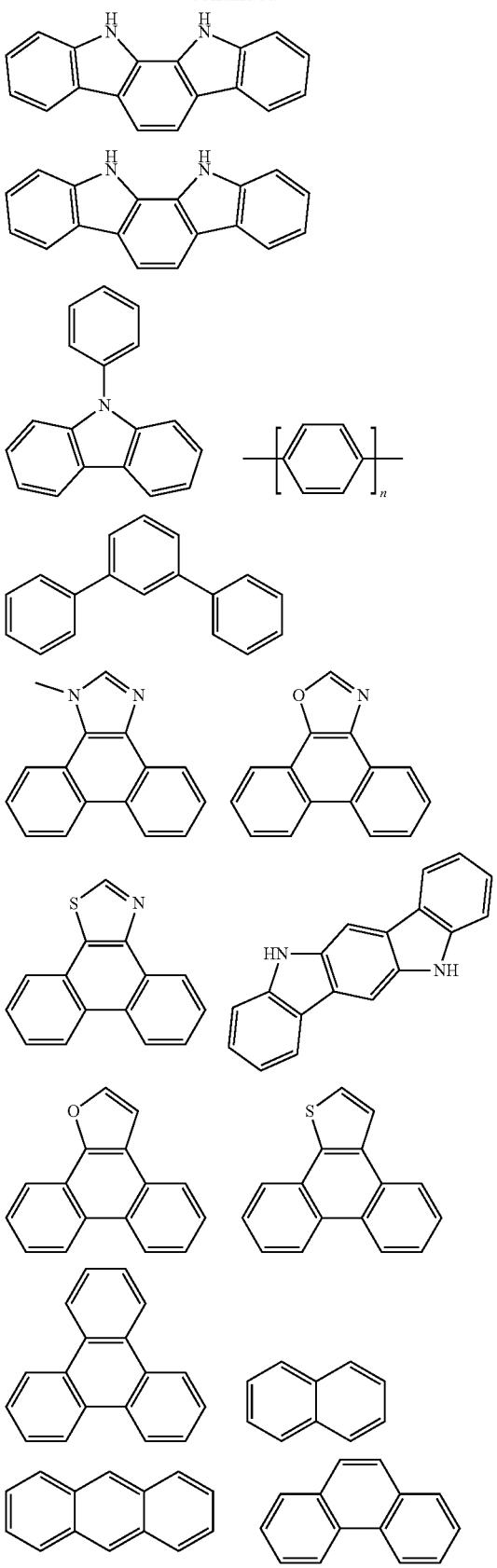

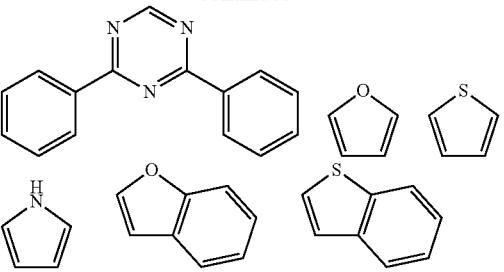

wherein n is 1, 2, 3 or 4.

In some embodiments, the compound according to the present disclosure has a relatively high electron mobility, typically greater than or equal to $10^{-5}$ cm$^2$/V·s, further greater than or equal to $10^{-4}$ cm$^2$/V·s, still further greater than or equal to $10^{-3}$ cm$^2$/V·s.

In other embodiments, the compound according to the present disclosure has a glass transition temperature greater than or equal to 100° C., further greater than or equal to 110° C., still further greater than or equal to 120° C., even further greater than or equal to 140° C.

In other embodiments, the lowest unoccupied molecular orbital energy level LUMO of the compound according to the present disclosure is less than or equal to −2.9 eV, further less than or equal to −2.95 eV, still further less than or equal to −3.0 eV, even further less than or equal to −3.05 eV.

In other embodiments, the highest occupied molecular orbital energy level HOMO of the compound according to the present disclosure is less than or equal to −5.7 eV, further less than or equal to −5.8 eV, still further less than or equal to −5.9 eV, even further less than or equal to −6.0 eV.

In other embodiments, the triplet excited state energy level T1 of the compound according to the present disclosure is greater than or equal to 1.8 eV, further greater than or equal to 1.9 eV, still further greater than or equal to 2.0 eV, even further greater than or equal to 2.1 eV.

In other embodiments, the ΔHOMO of the compound according to the present disclosure is greater than or equal to 0.5 eV, further greater than or equal to 0.55 eV, still further greater than or equal to 0.6 eV, even further greater than or equal to 0.7 eV.

In the embodiments of the present disclosure, the energy level structure, i.e., the triplet excited state energy level $E_T$, HOMO and LUMO of the organic compound play a key role. The determination of these energy levels is described below.

The HOMO and LUMO energy levels can be measured by photoelectric effect, such as XPS (X-ray Photoelectron Spectroscopy) and UPS (Ultraviolet Photoelectron Spectroscopy) or by Cyclic Voltammetry (hereinafter referred to as CV). Recently, quantum chemistry method such as density functional theory (hereinafter referred to as DFT), has also become a feasible method for calculating molecular orbital energy levels.

The triplet excited state energy level $E_T$ of organic materials can be measured by low temperature time-resolved luminescence spectroscopy, or obtained by quantum simulation calculation (e.g., by Time-dependent DFT), such as by the commercial software Gaussian 03W (Gaussian Inc.), and the specific simulation method may refer to WO2011141110 or may be as described in the embodiments below.

It should be noted that, the absolute values of HOMO, LUMO, $E_T$ depend on the measurement method or calculation method used, even for the same method, different HOMO/LUMO value may be obtained by different evaluation methods, such as at starting point and peak point on the CV curve. Therefore, reasonable and meaningful comparisons should be made by using same measurement method and same evaluation method. In the description of the embodiments of the present disclosure, the values of HOMO, LUMO and $E_T$ are based on the simulations of Time-dependent DFT, but this does not affect the application of other measurement or calculation methods. The energy level values determined by different methods should be calibrated against each other.

In the present disclosure, (HOMO-1) is defined as the second highest occupied molecular orbital energy level, (HOMO-2) is the third highest occupied molecular orbital energy level, and so on. Δ HOMO=|(HOMO-1)−HOMO|. (LUMO+1) is defined as the second lowest unoccupied molecular orbital energy level, (LUMO+2) is defined as the third lowest occupied molecular orbital energy level, and so on.

In an embodiment, the compound according to the present disclosure is at least partially deuterated, further 10% of H is deuterated, still further 20% of H is deuterated, even further 30% of H is deuterated, and even further 40% of H is deuterated.

Suitable examples of the compound according to the present disclosure are listed below, but are not limited to the following structures:

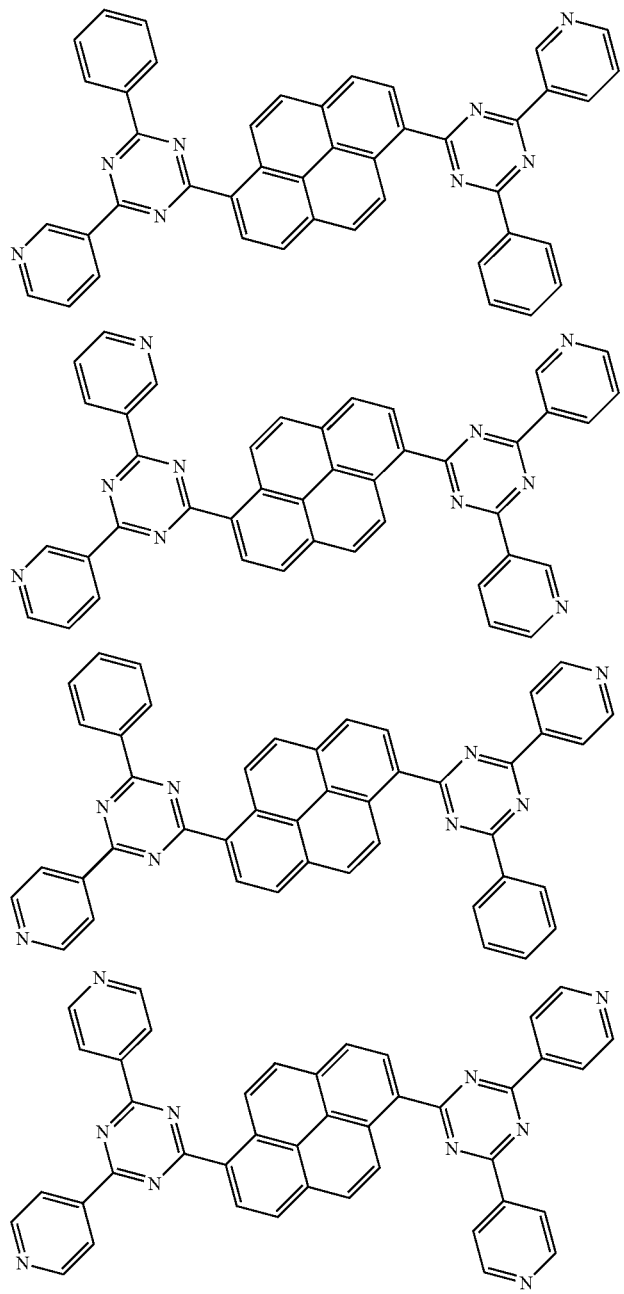

-continued
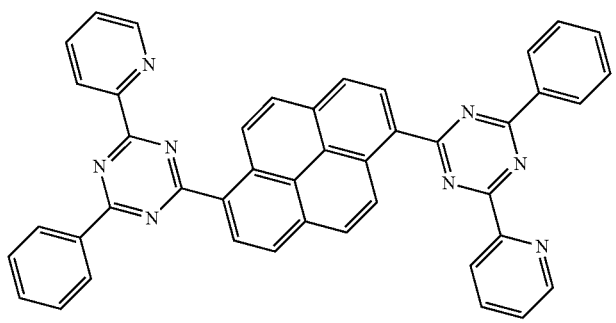
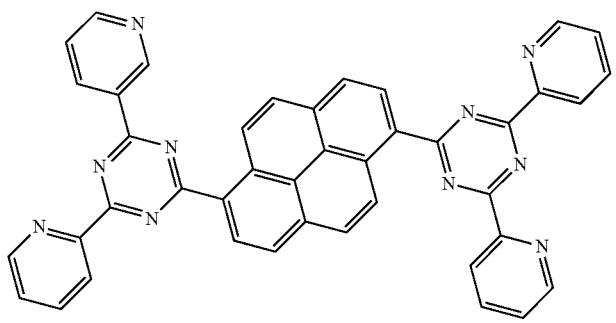
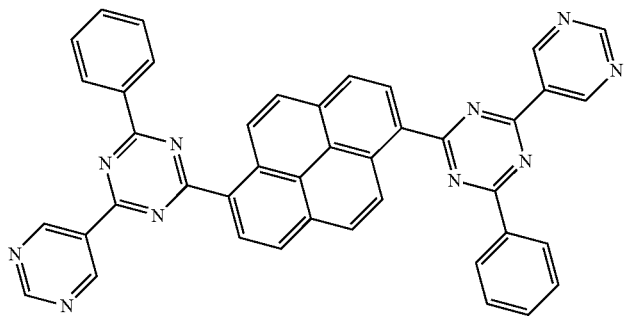
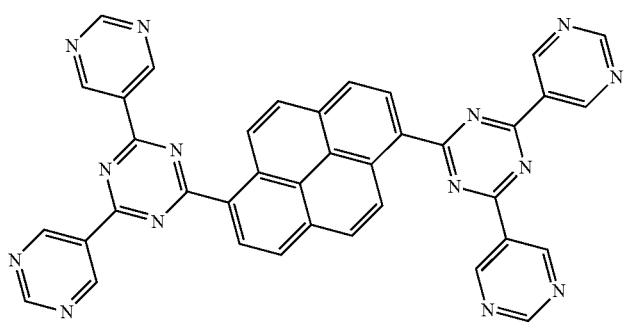

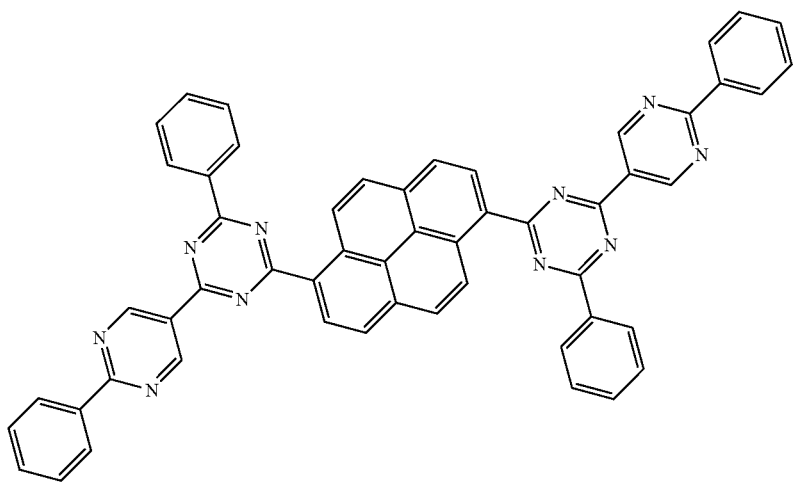
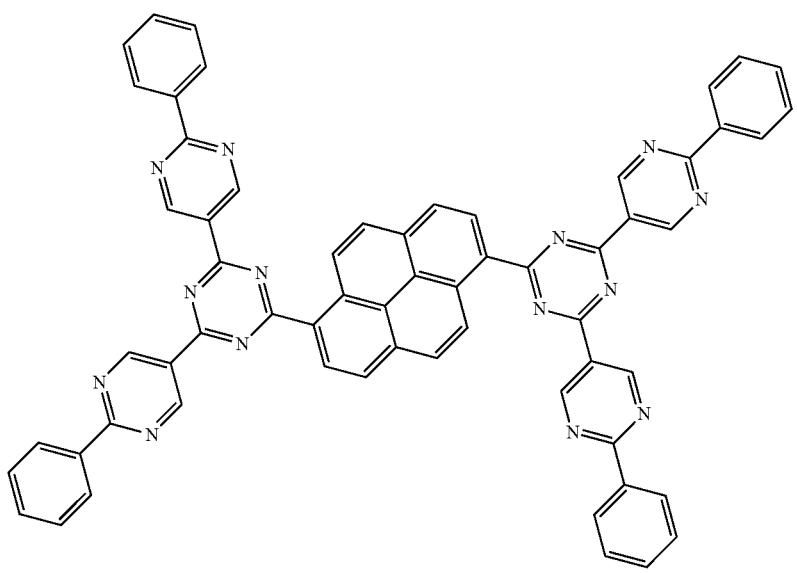
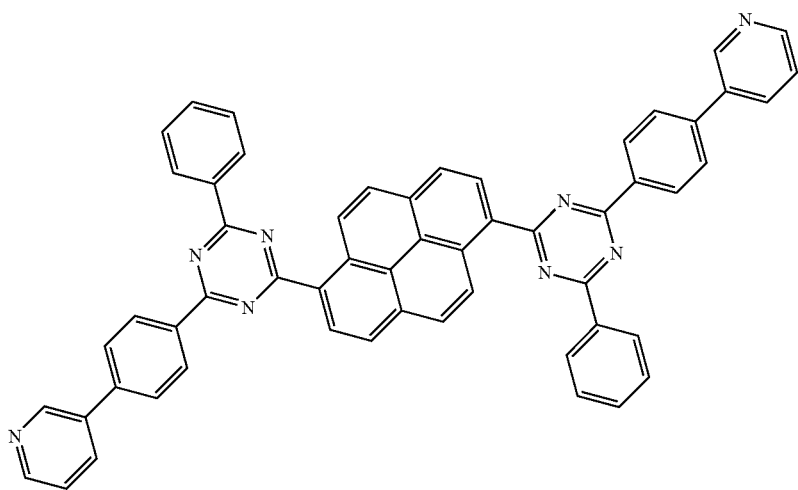

-continued
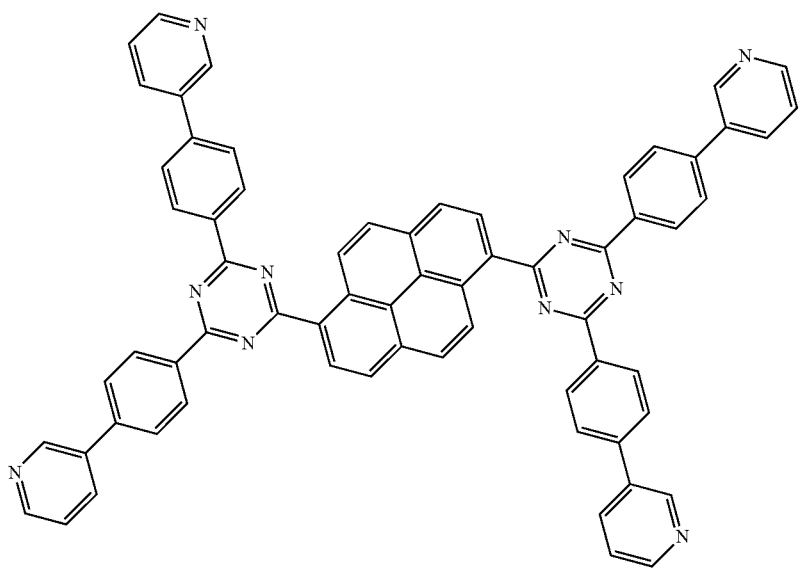
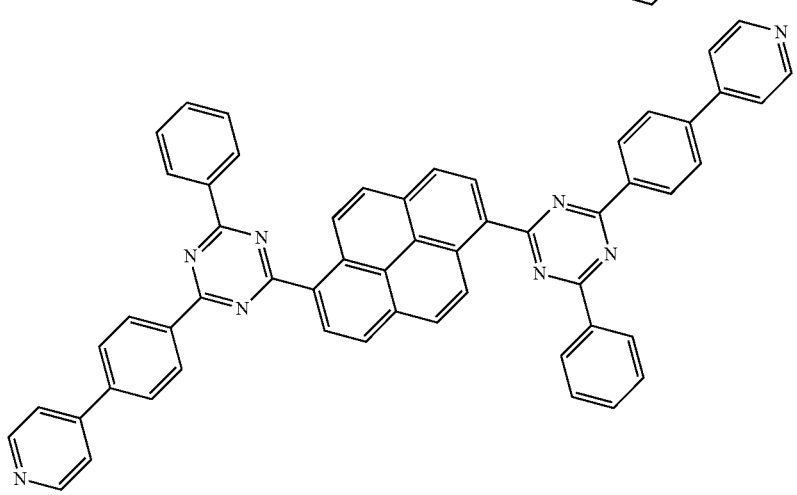
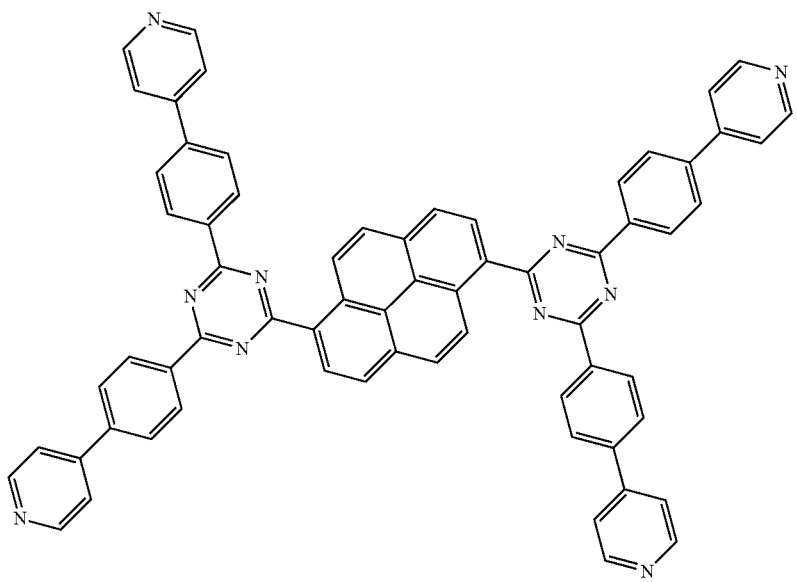

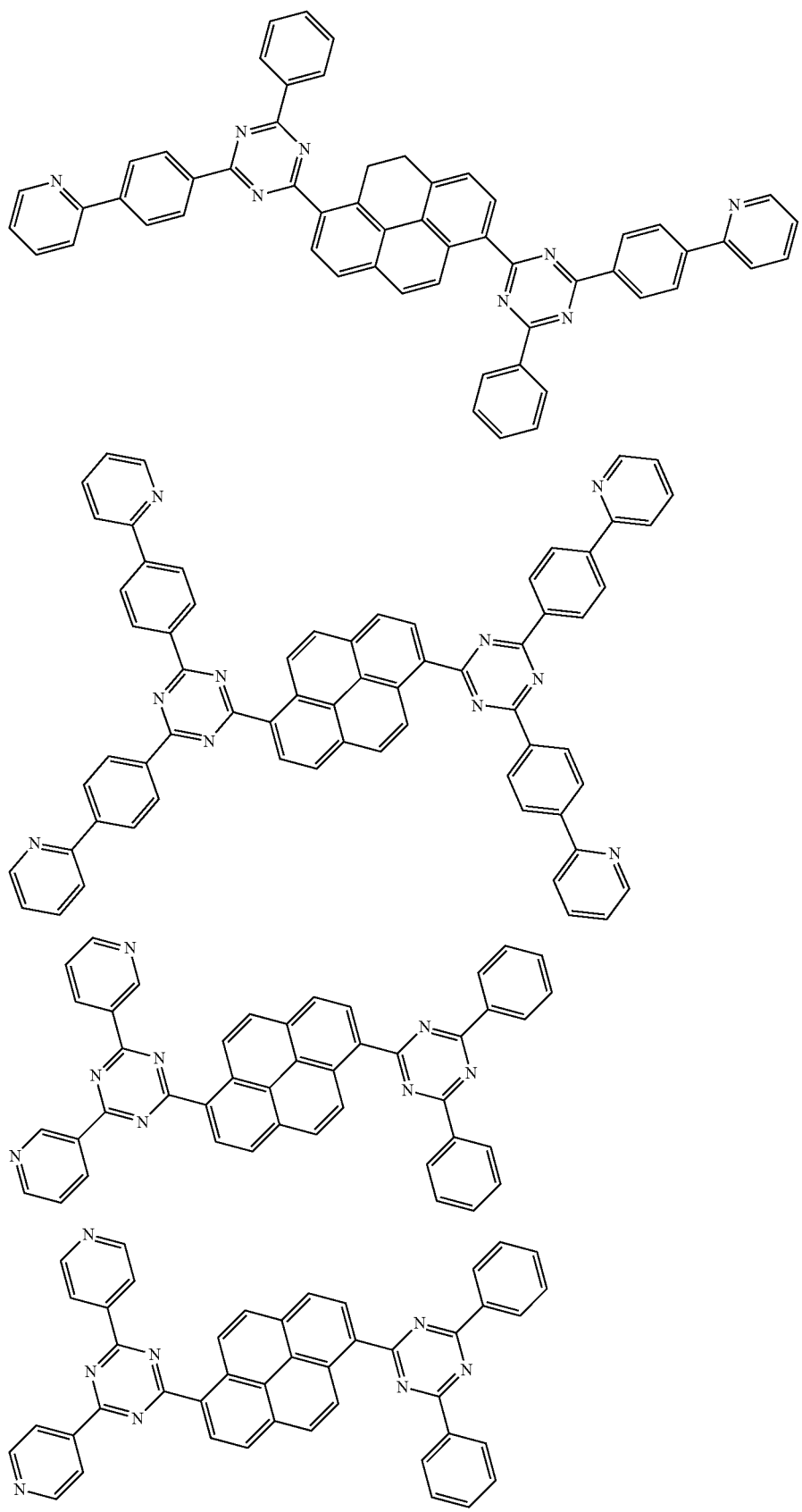

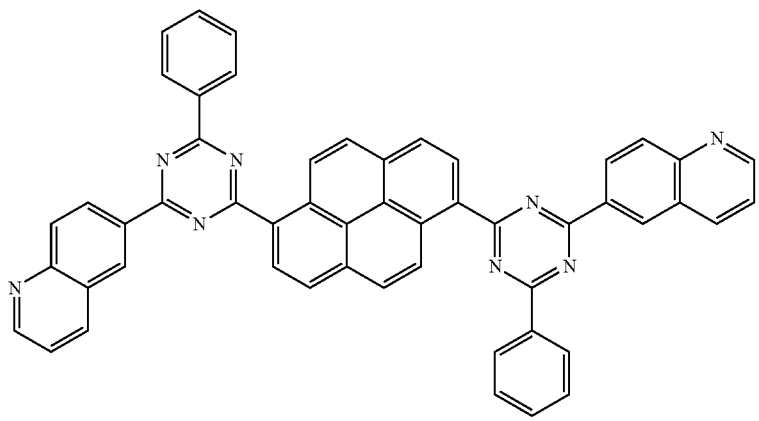
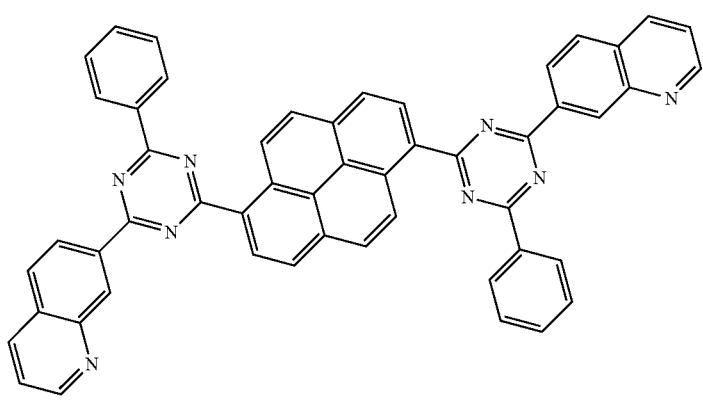
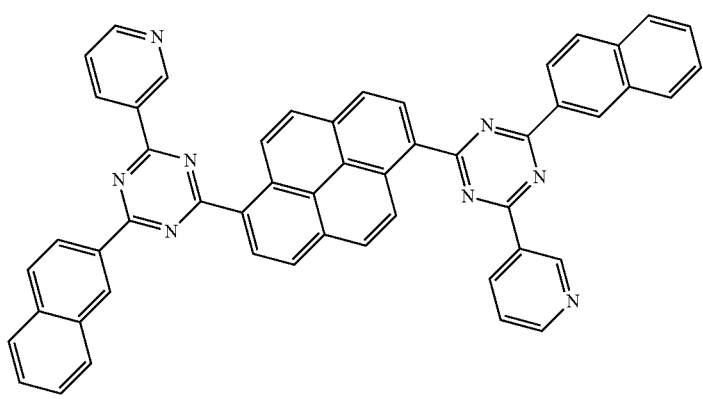
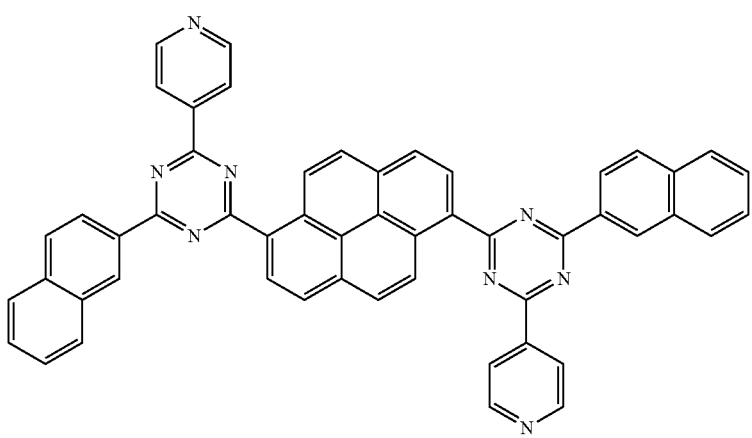

-continued
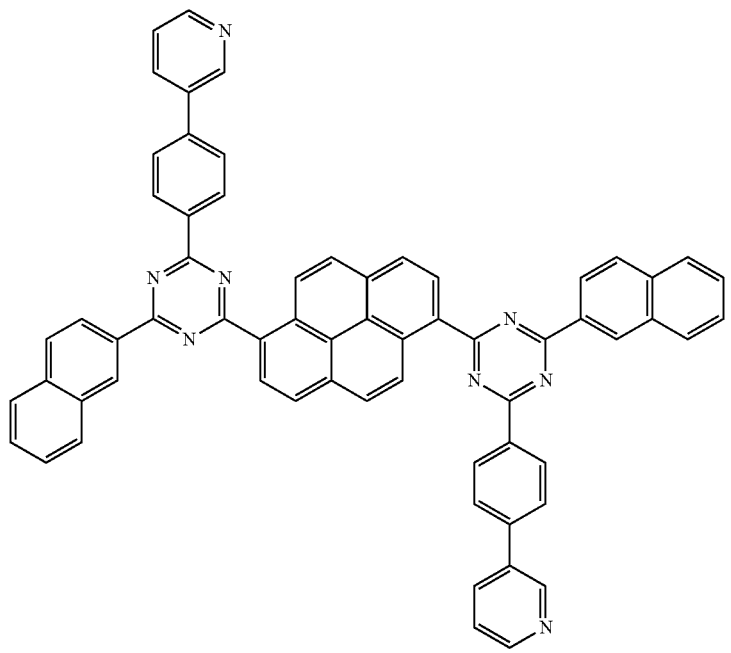
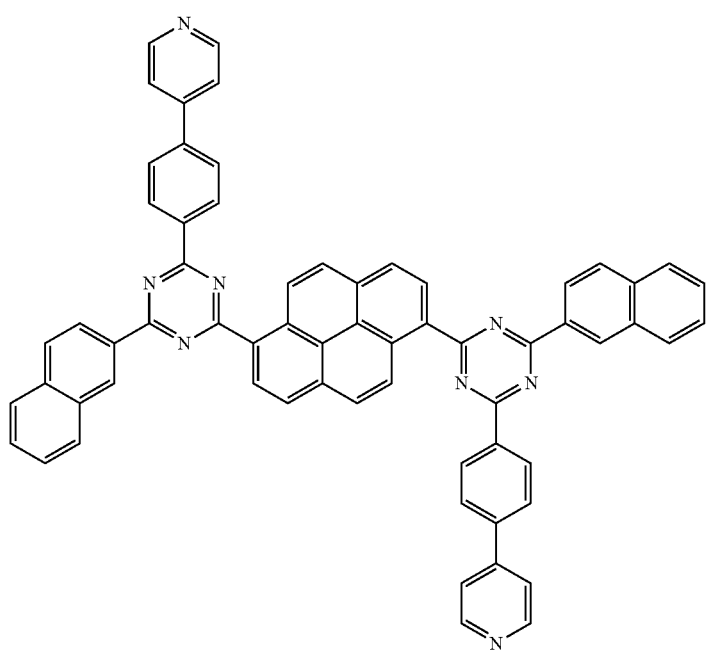
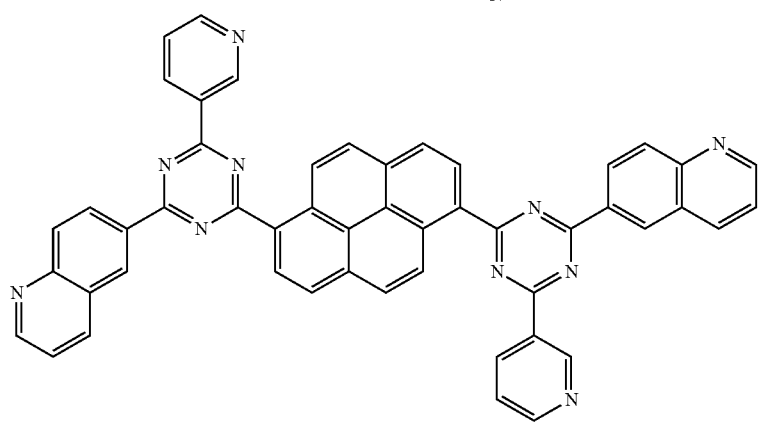

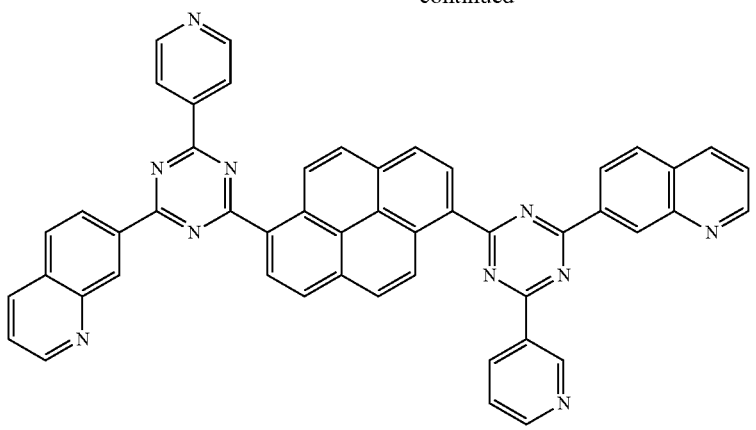
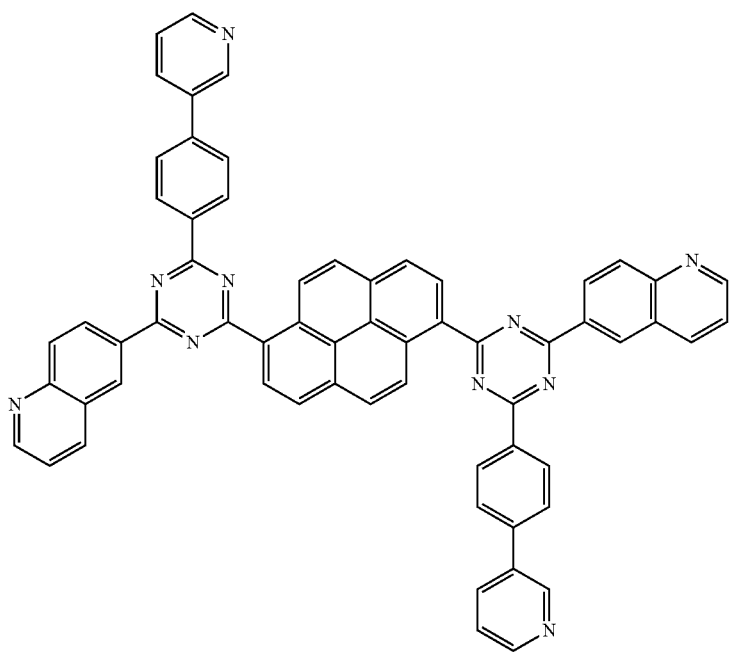
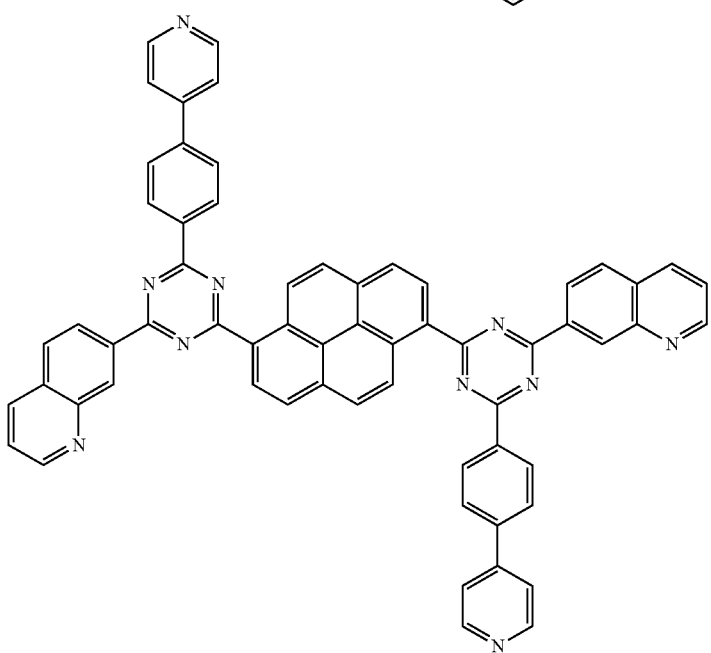

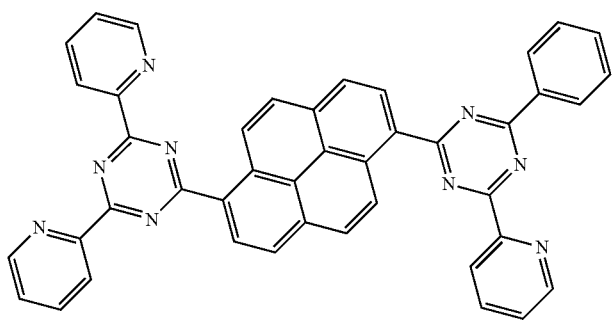
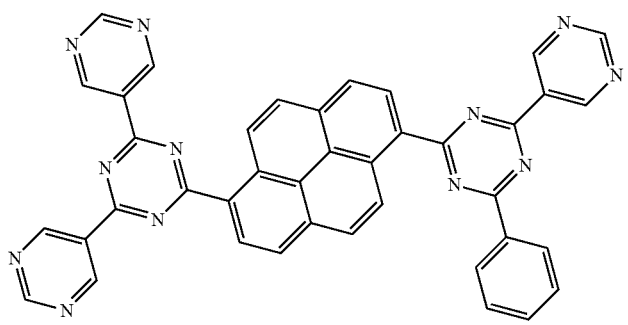
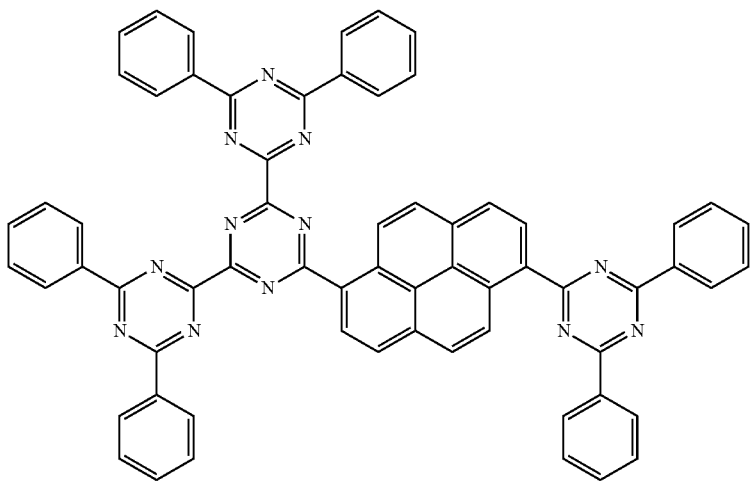

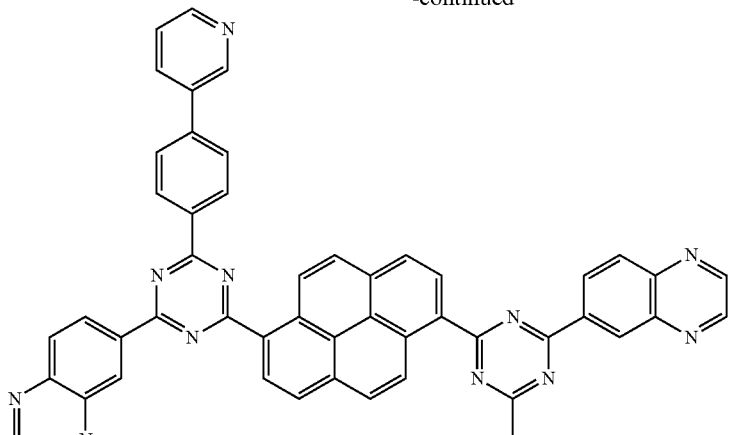
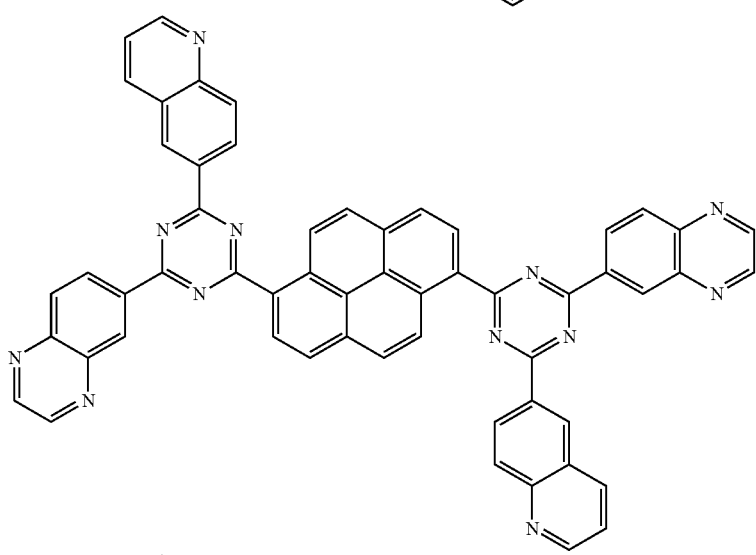
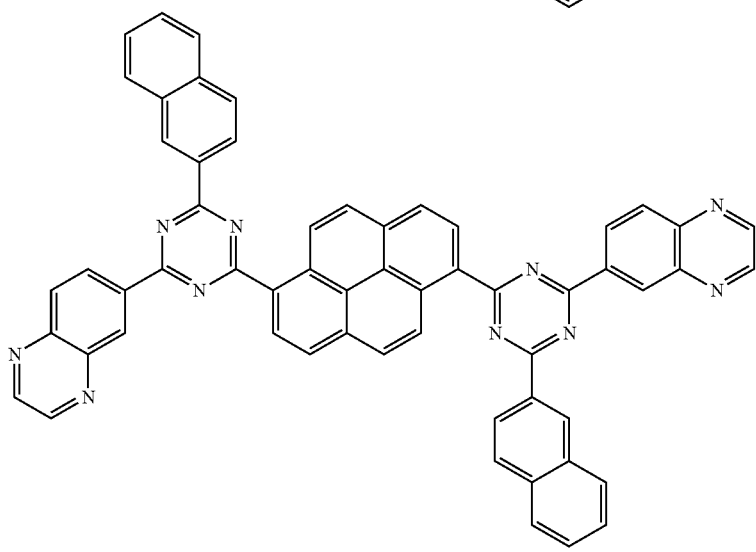

-continued
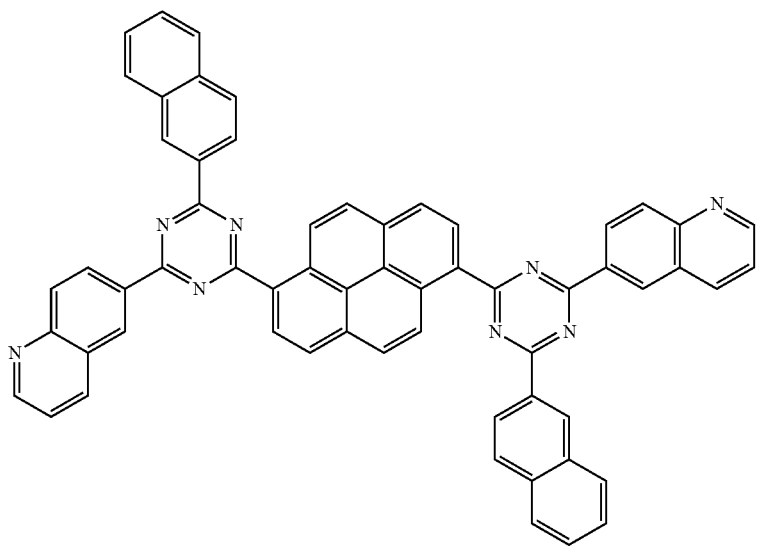
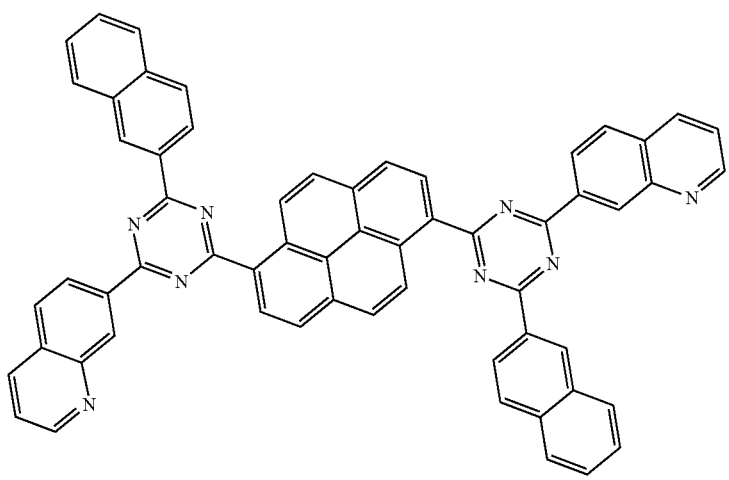
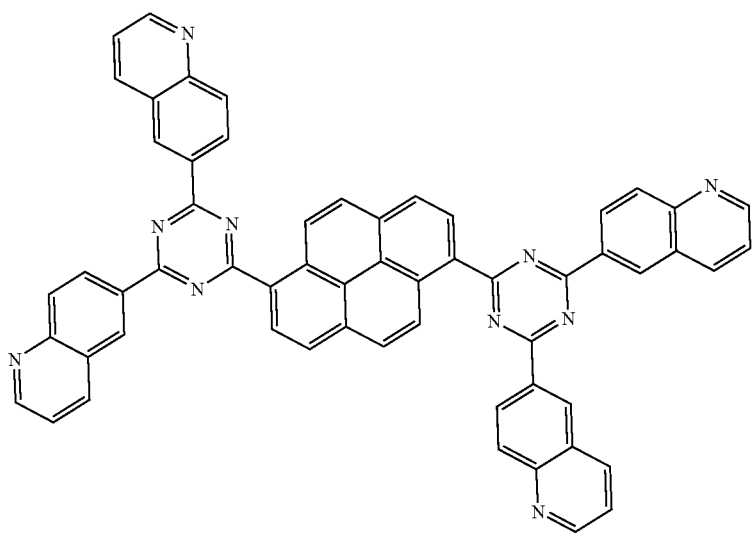

-continued
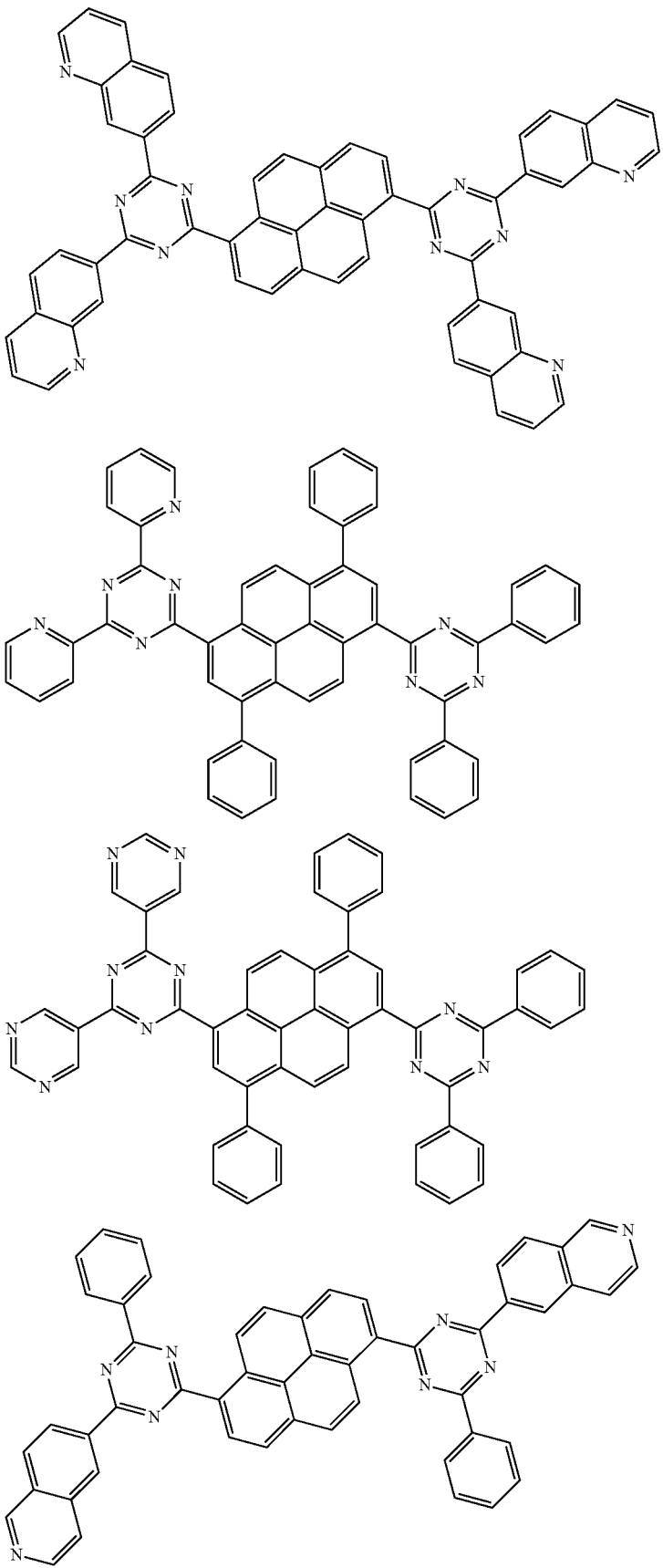

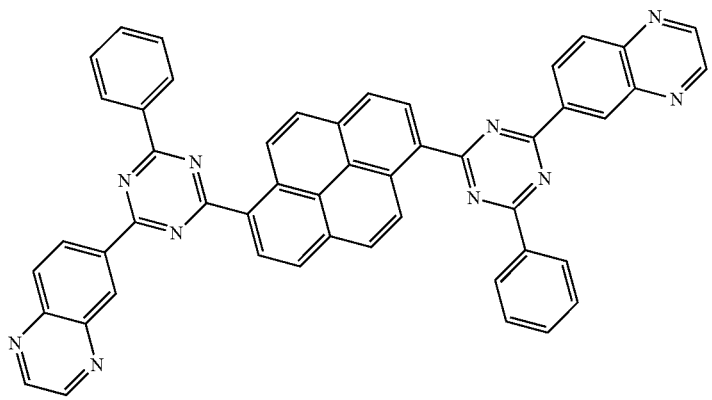
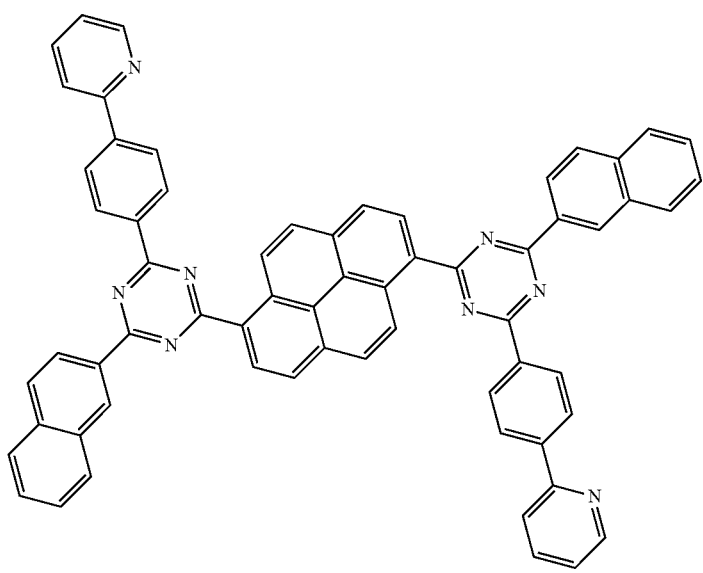
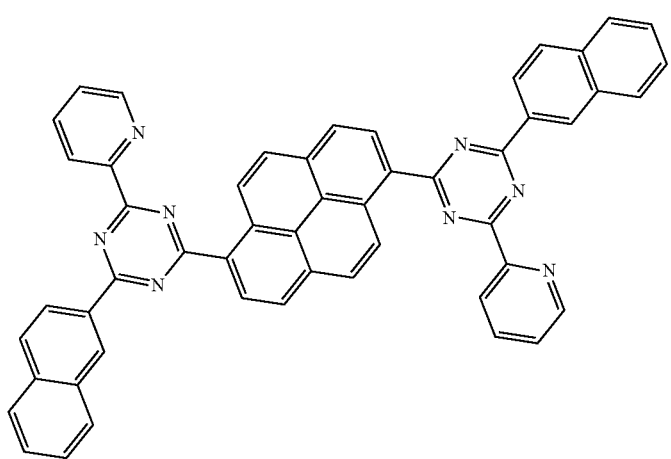

-continued
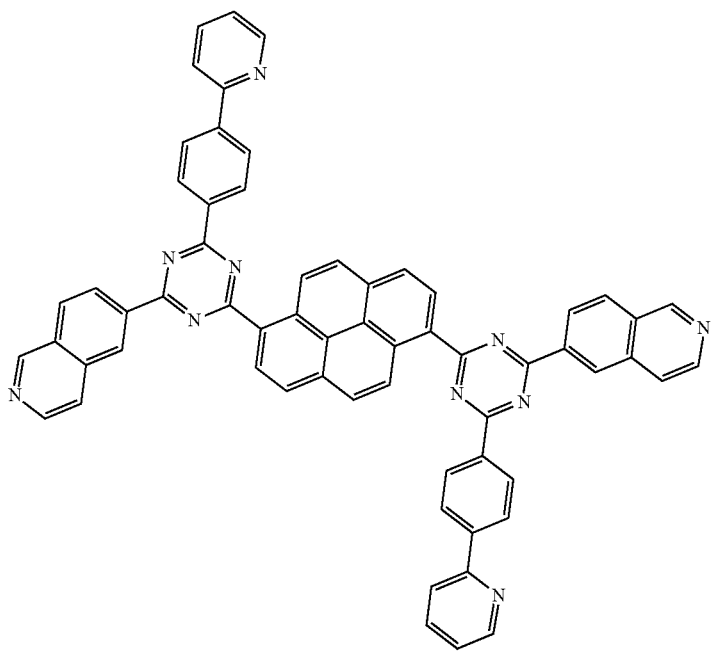
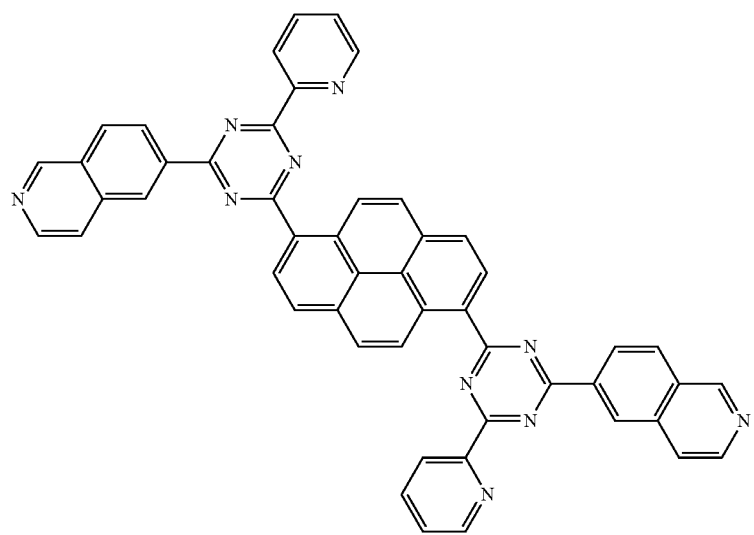

-continued
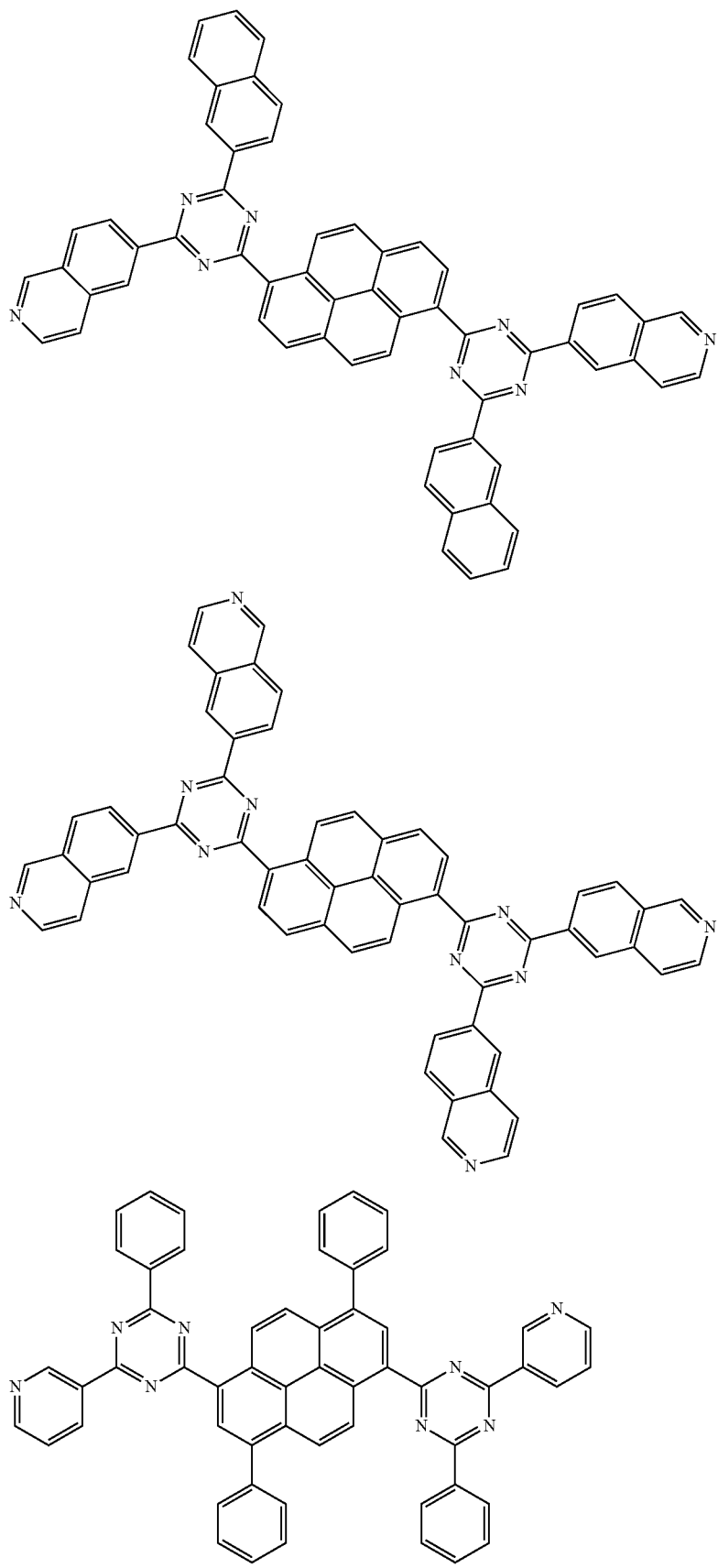

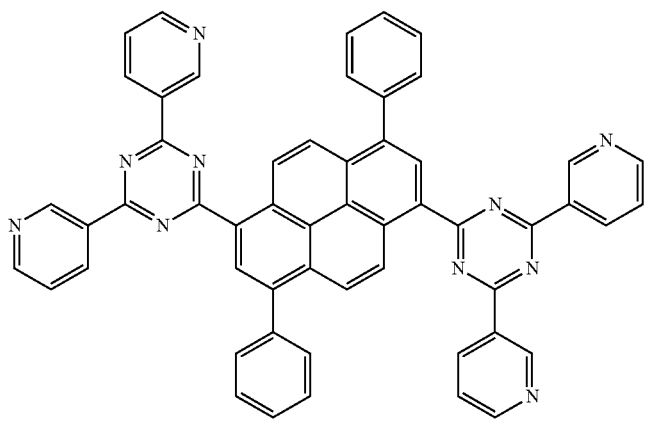
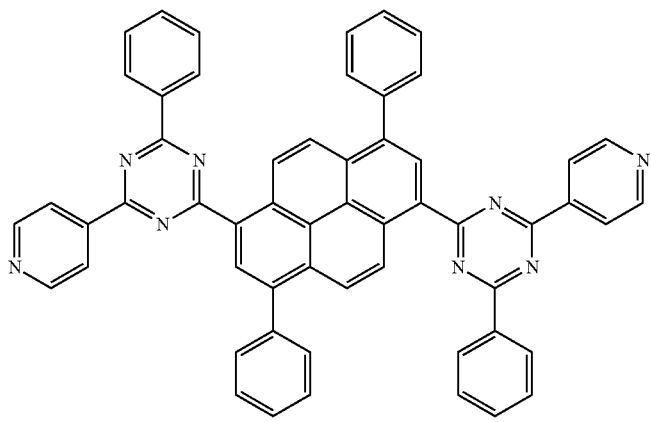
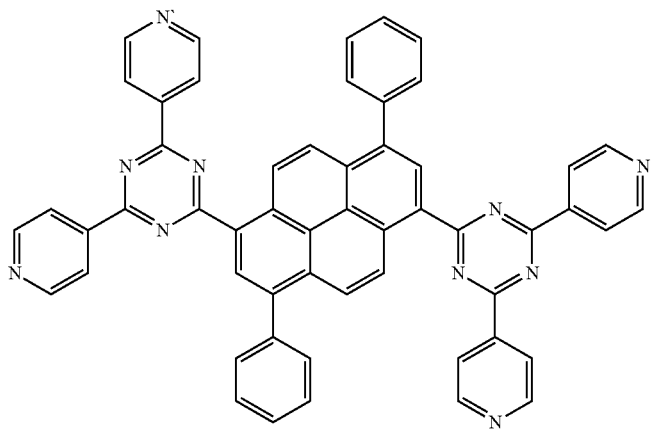
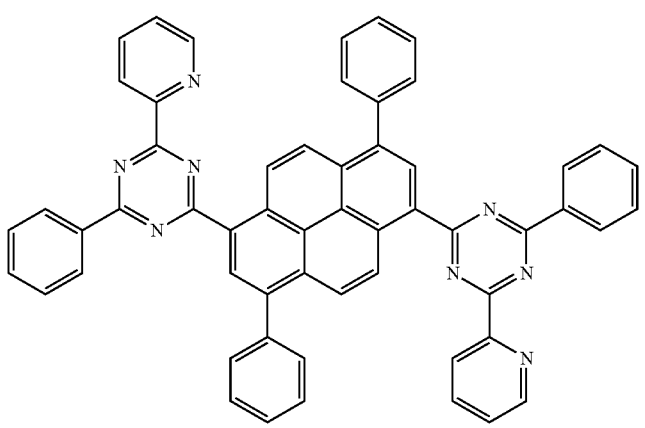

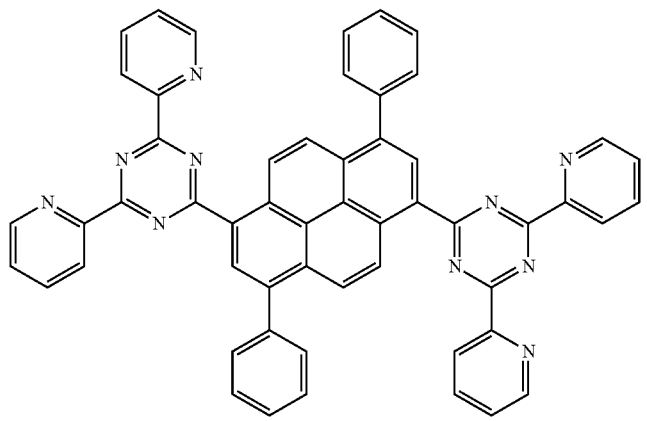
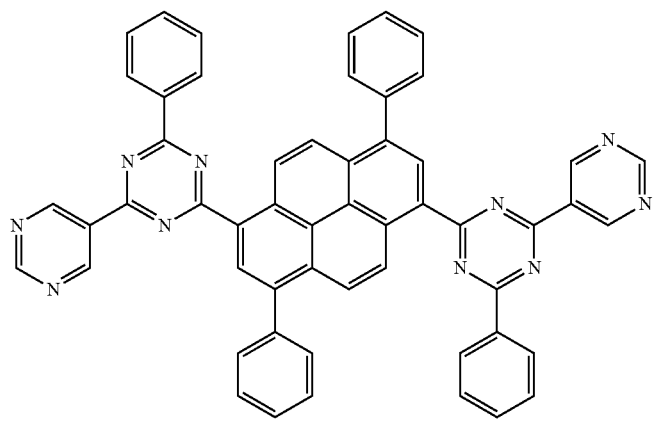
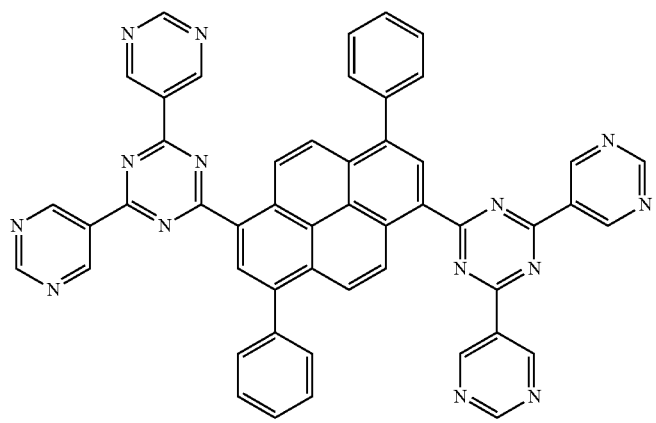

-continued
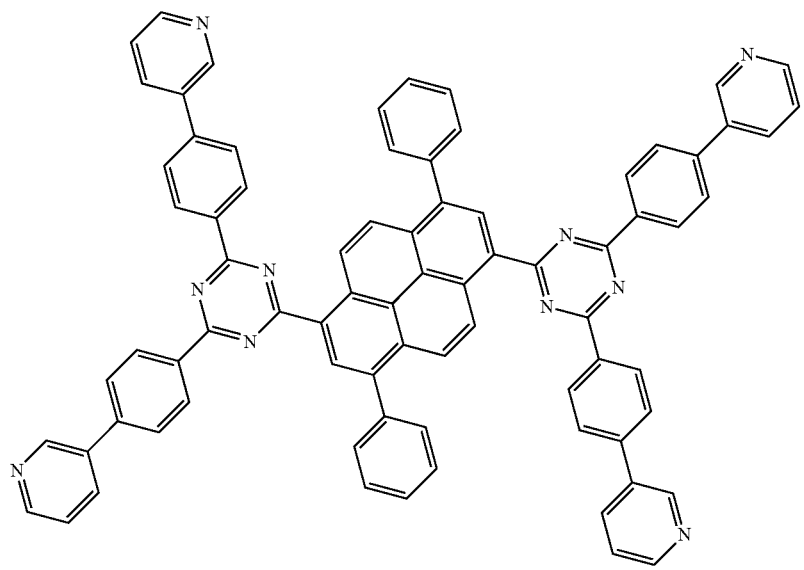
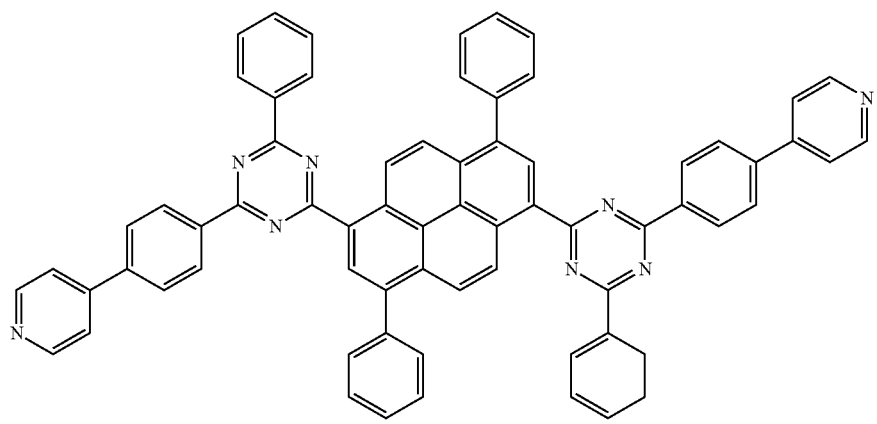
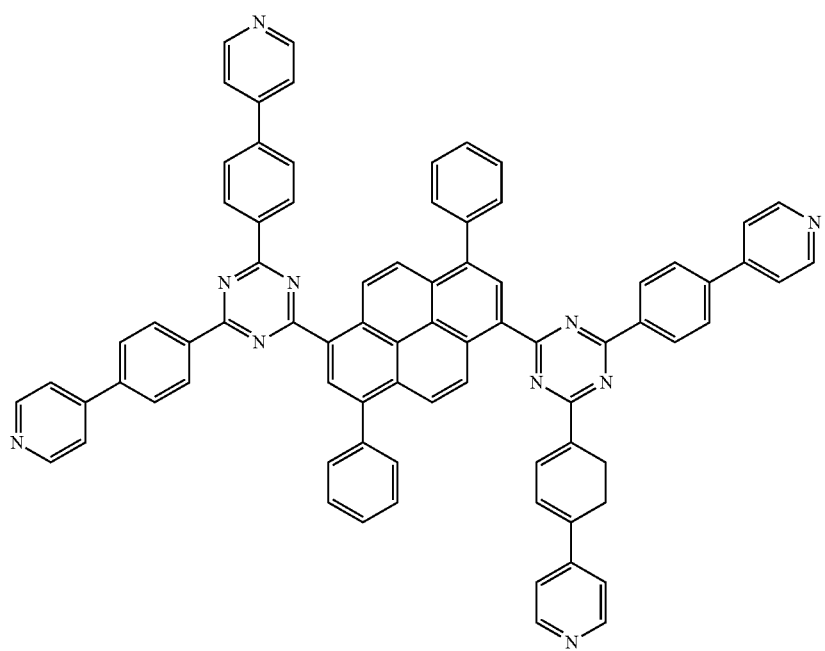

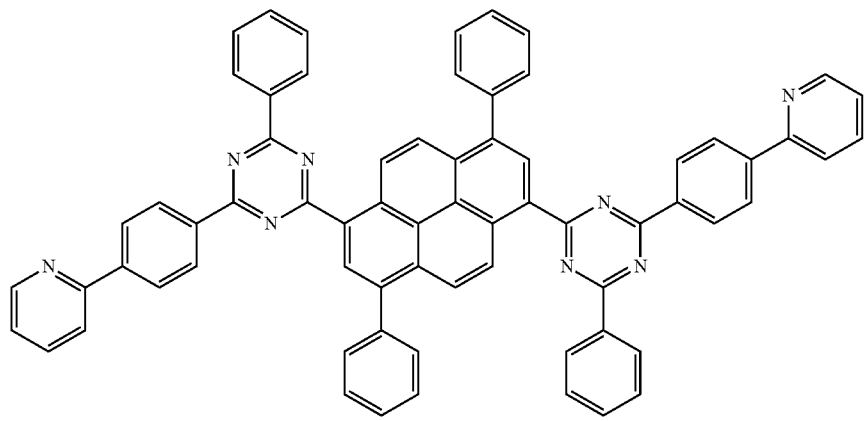
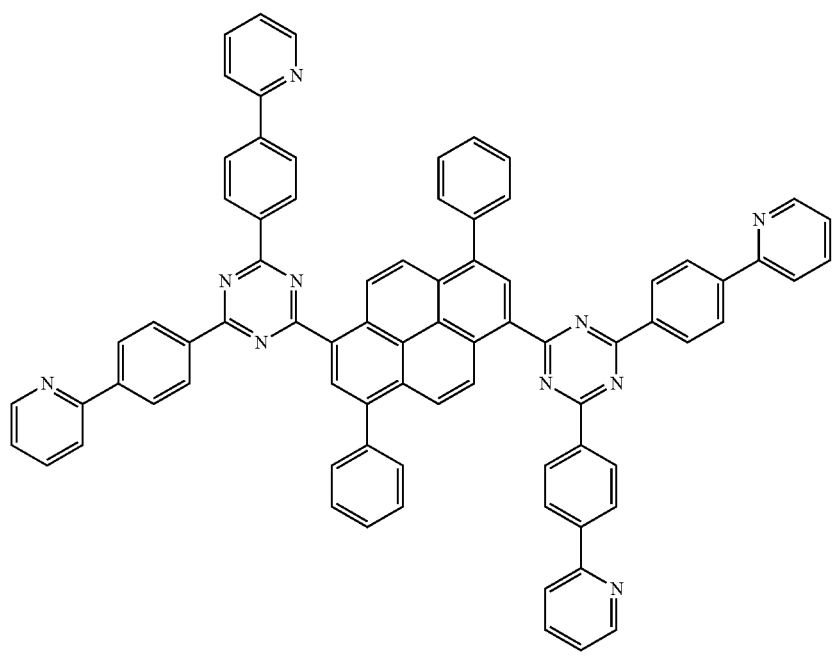
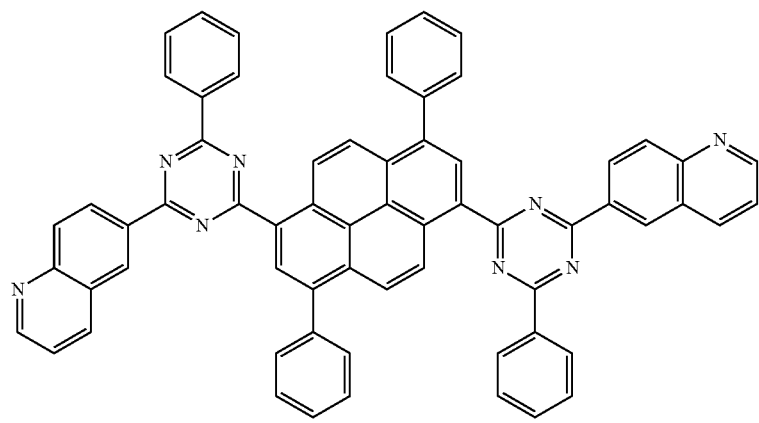

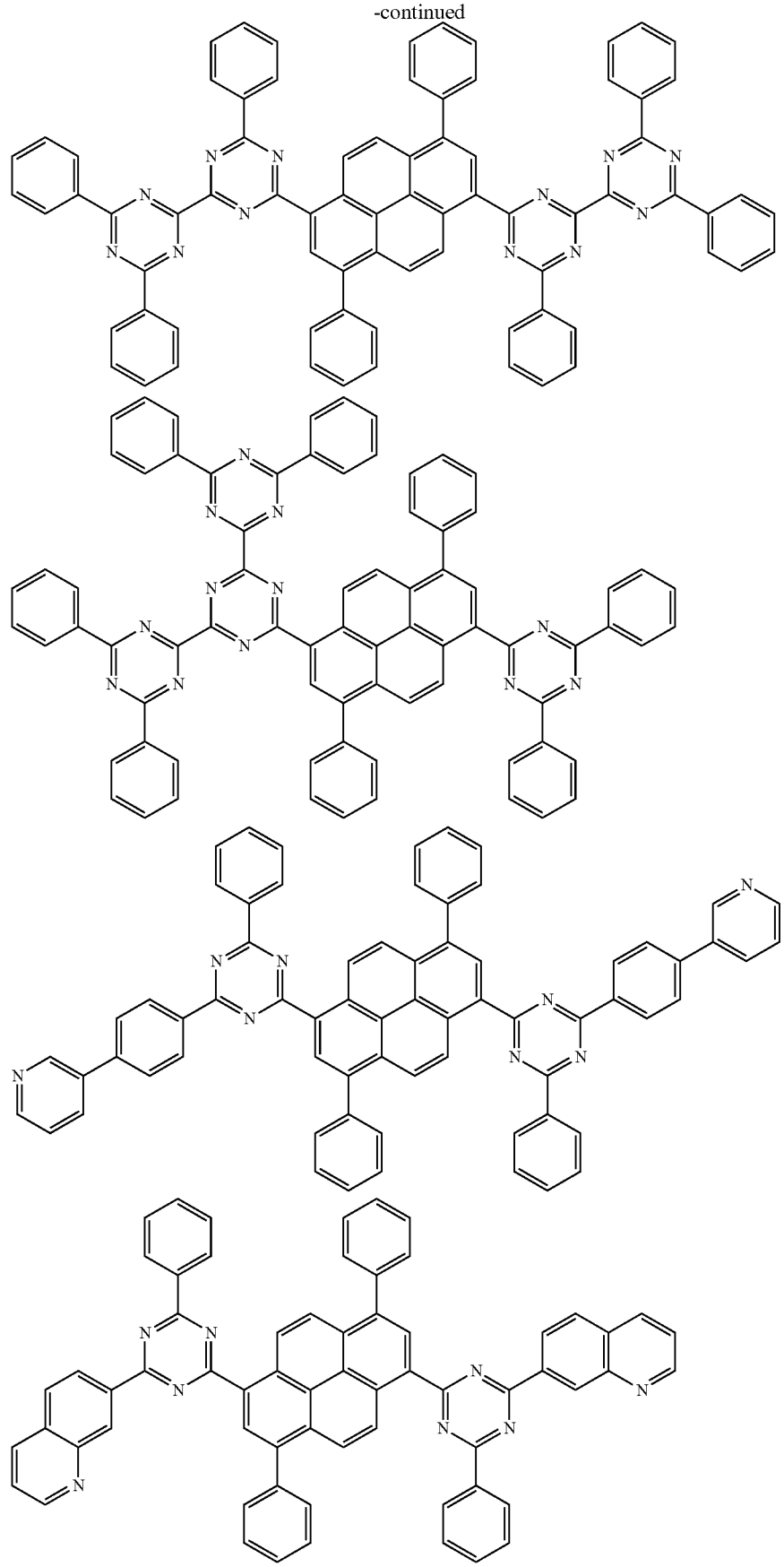

-continued
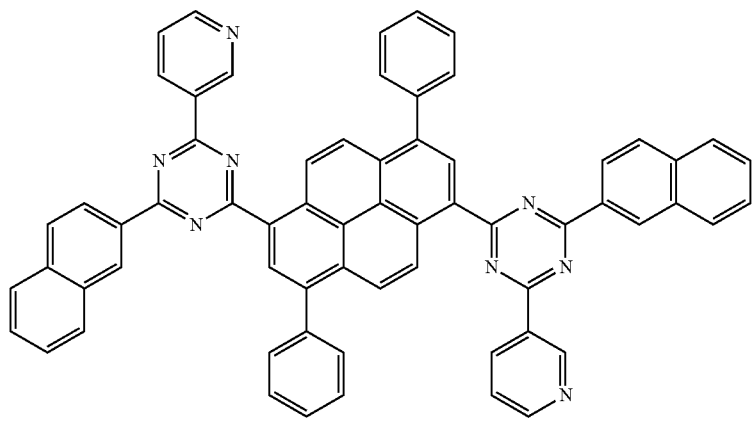
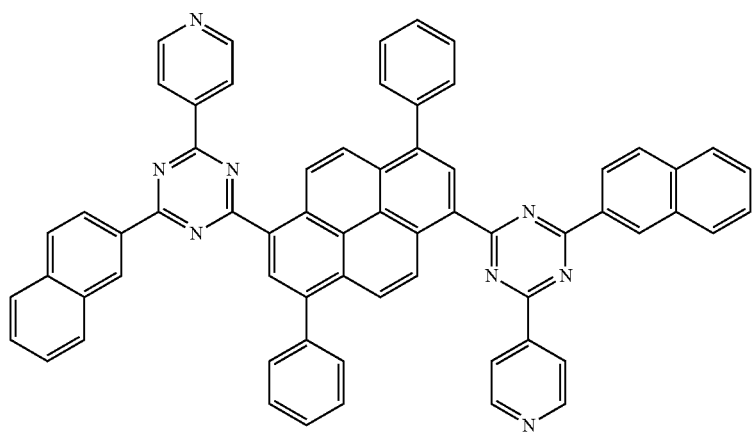
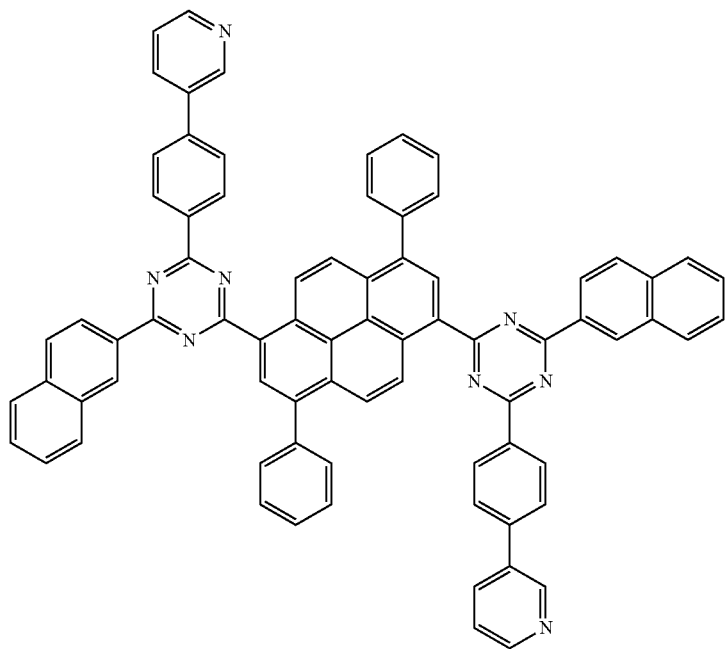

-continued
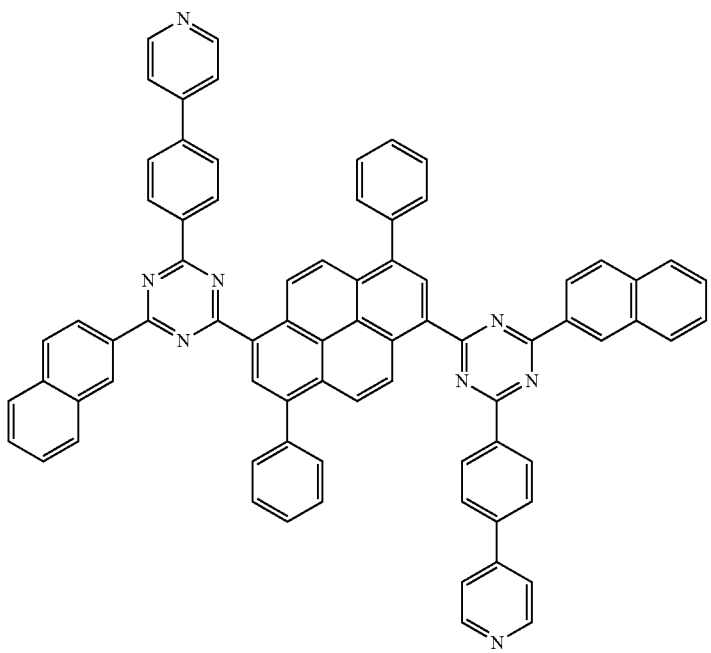
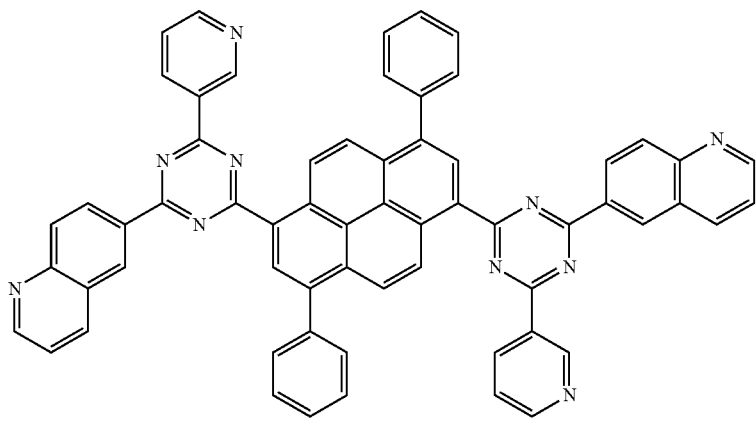
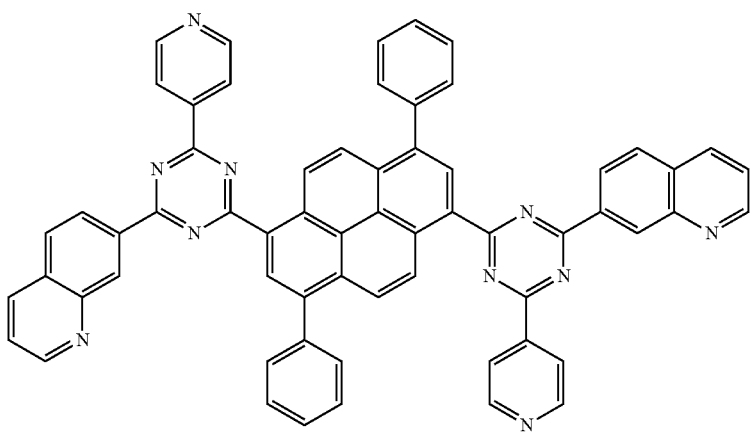

-continued
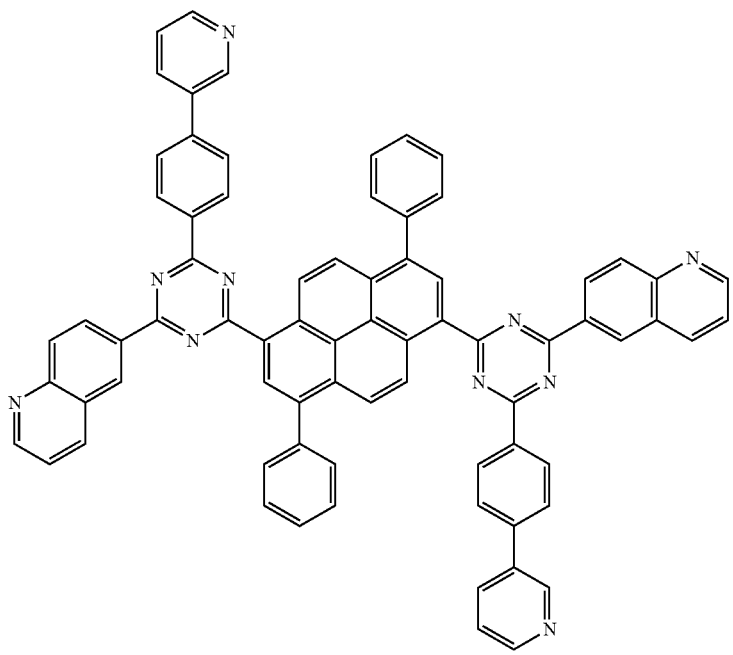
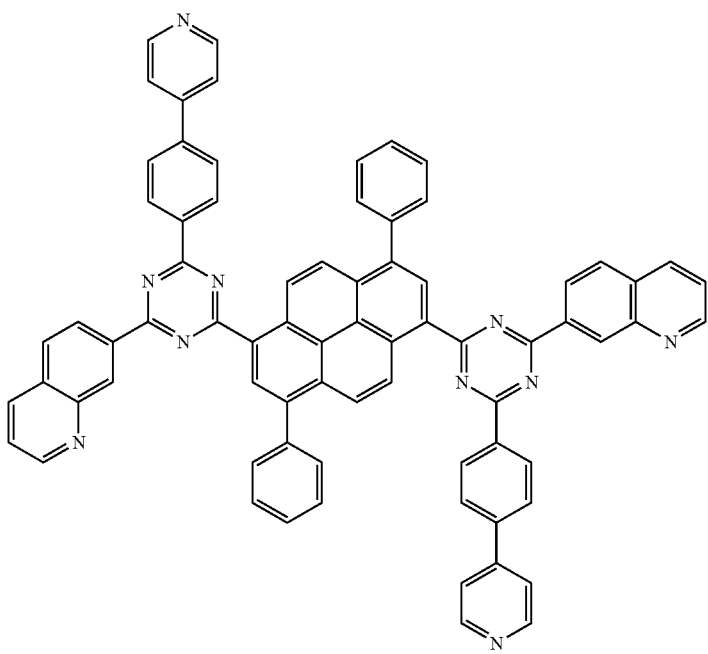
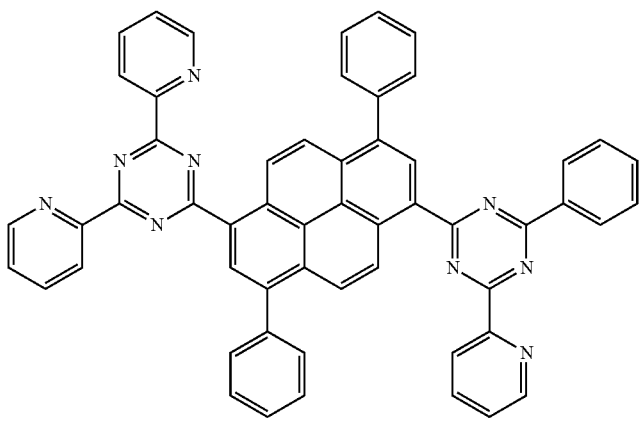

-continued
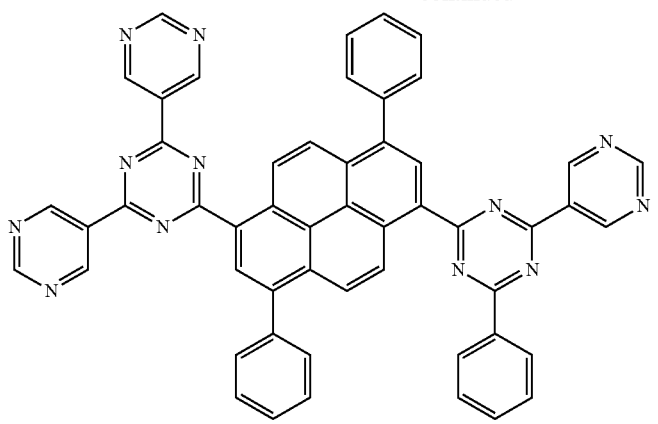
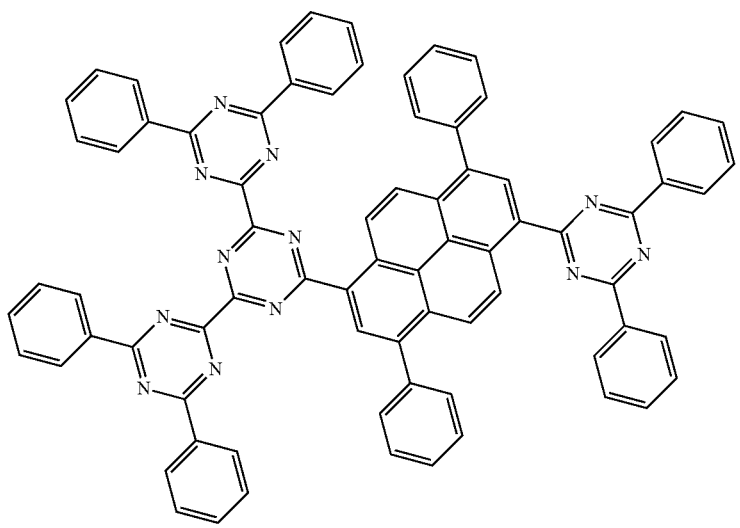
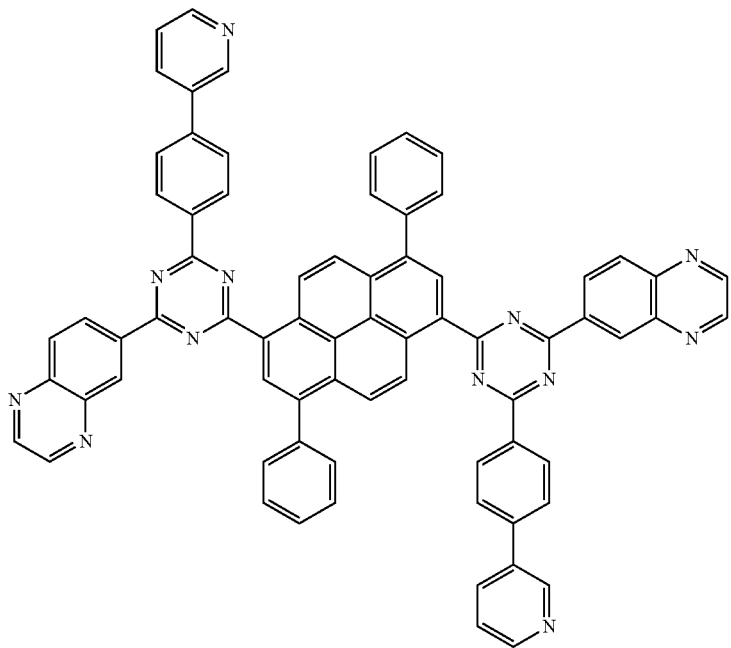

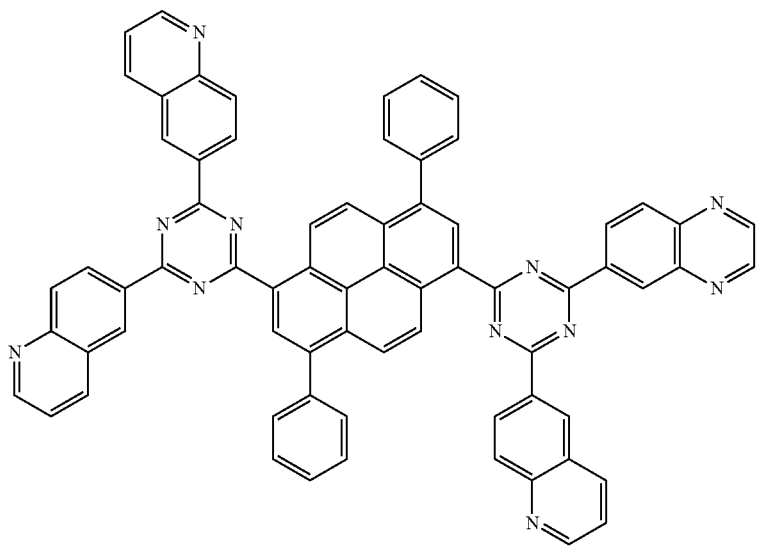
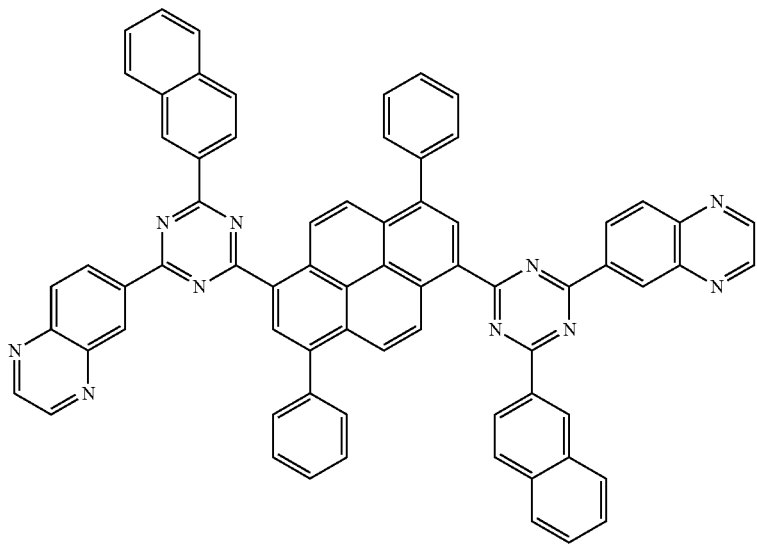
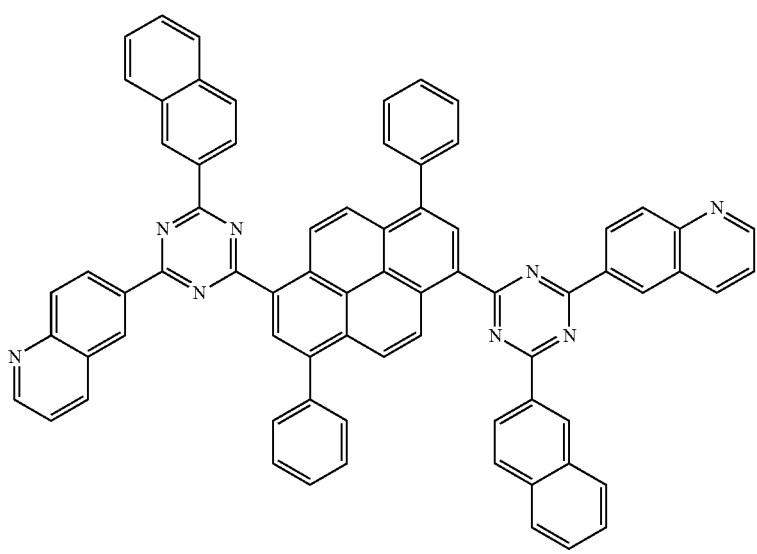

-continued
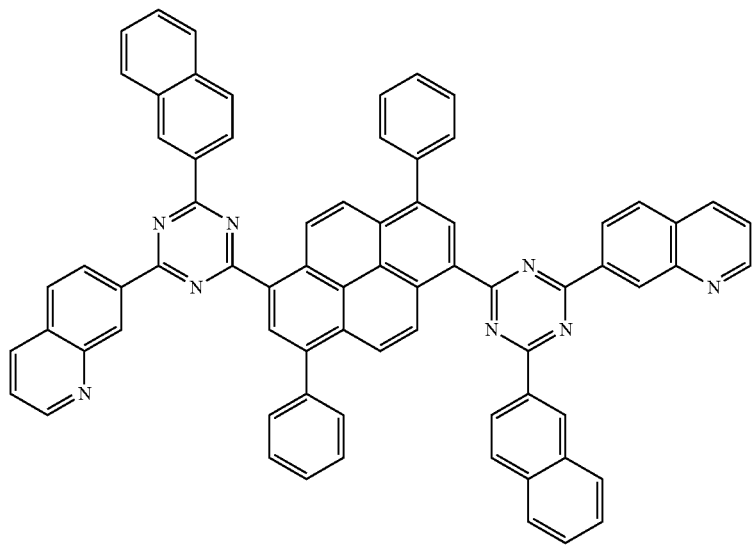
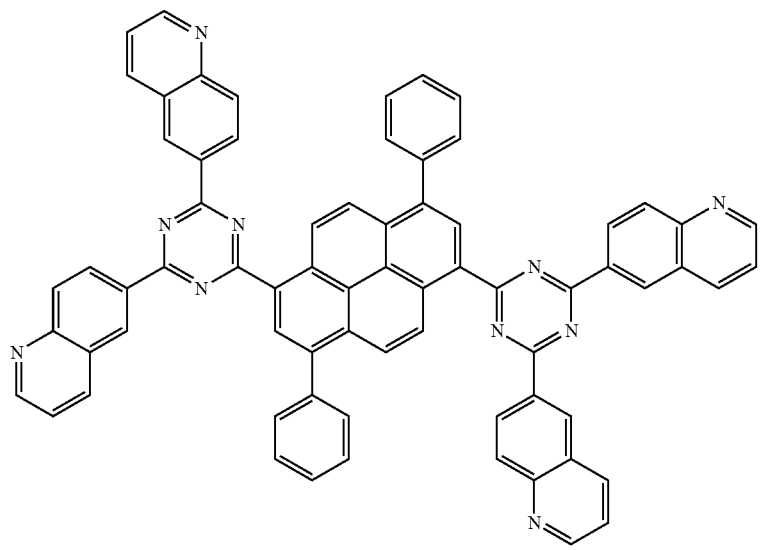
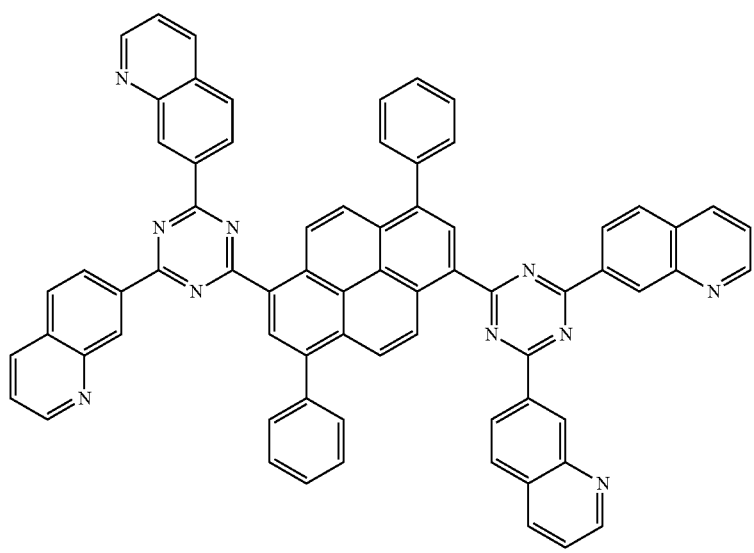

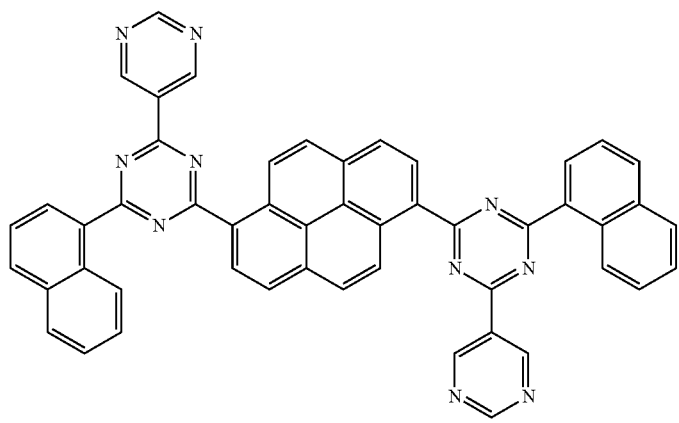
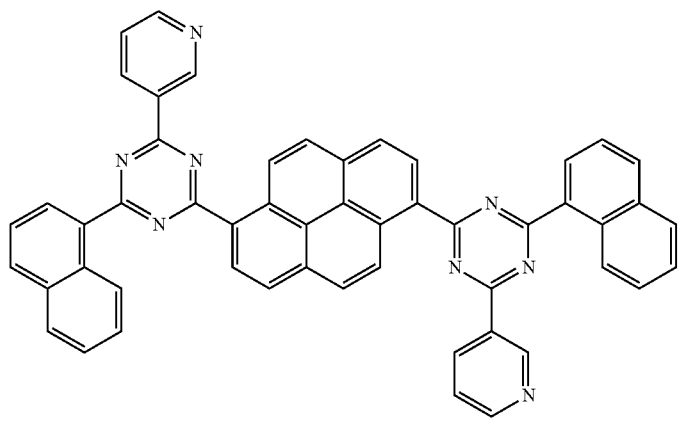
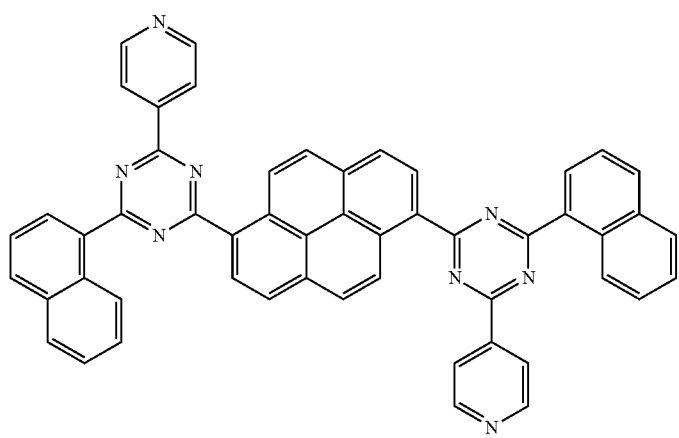
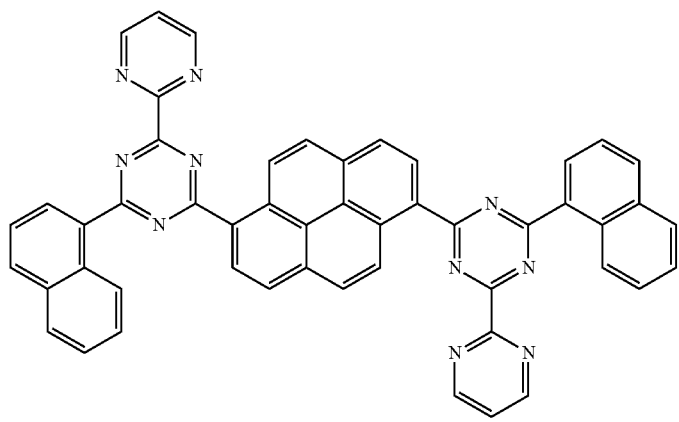

-continued
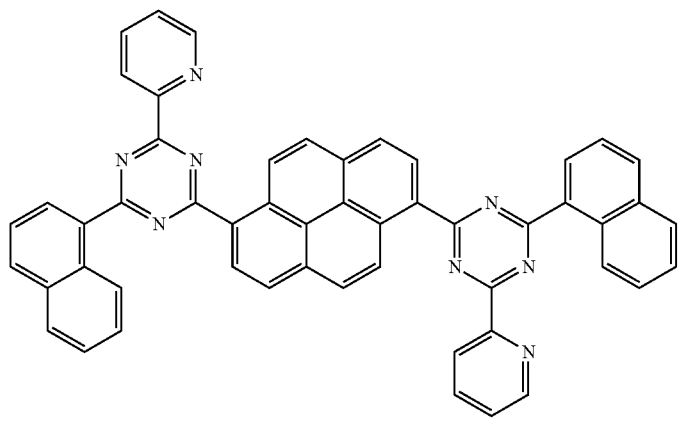
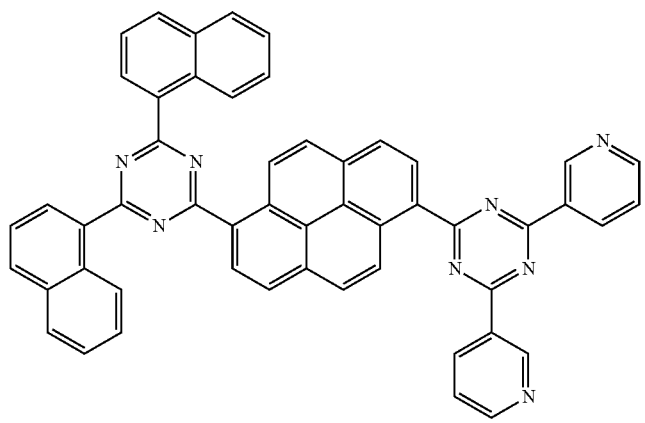
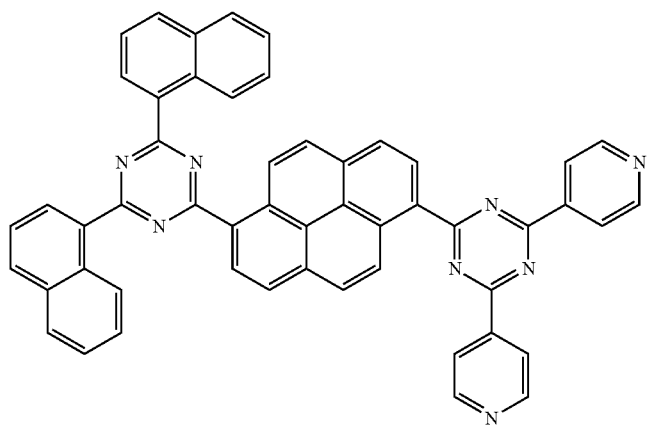
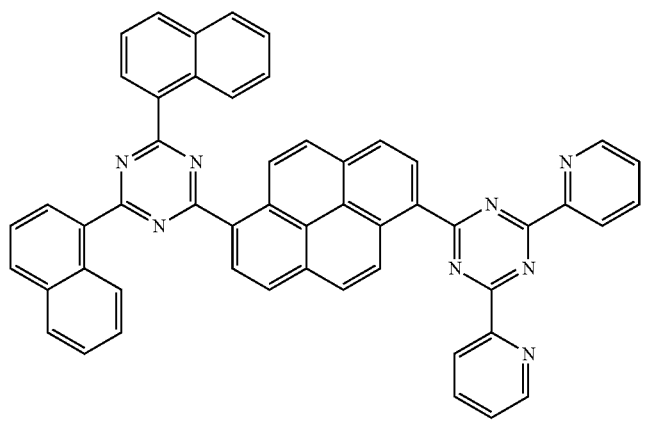

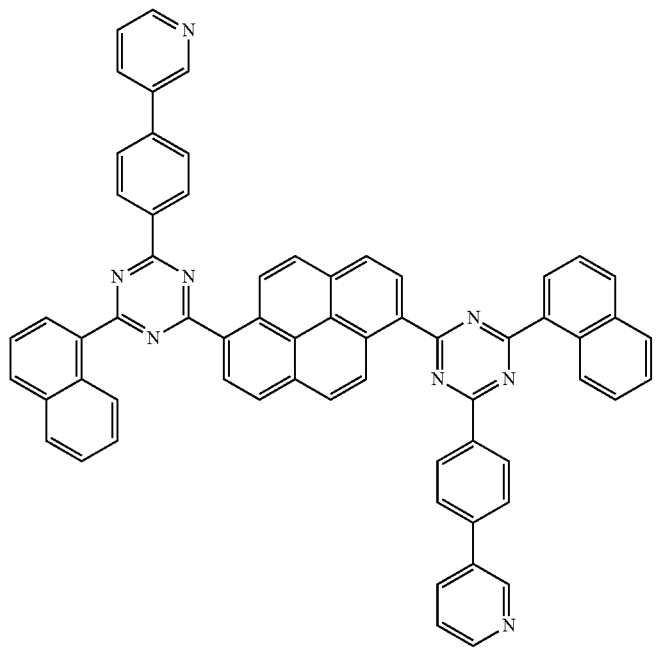
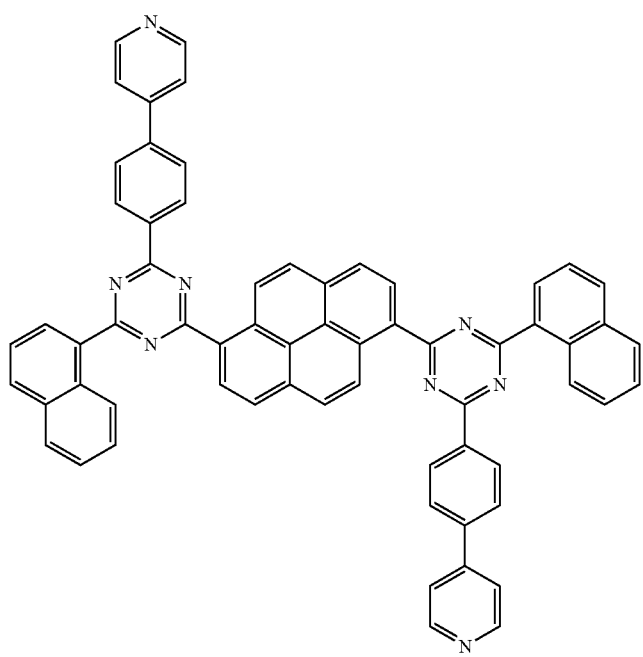

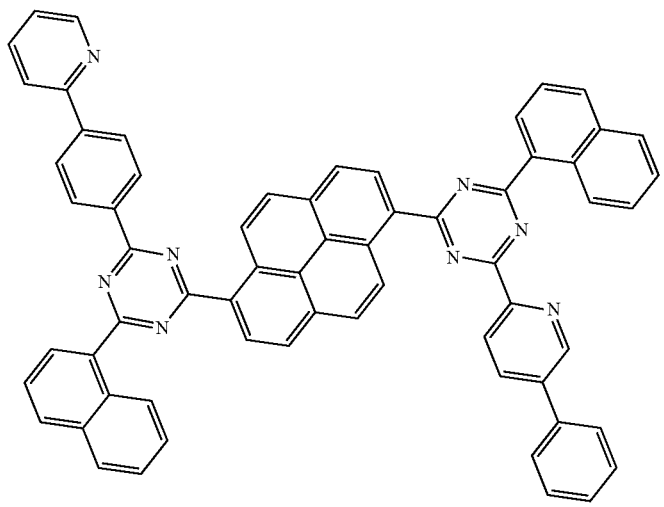
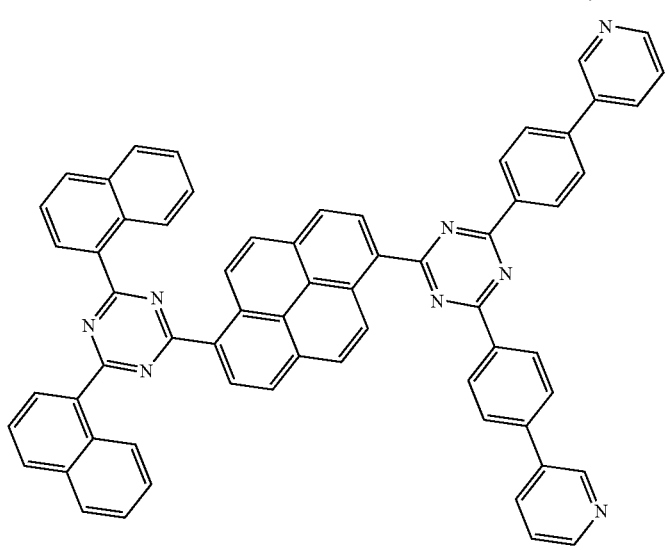
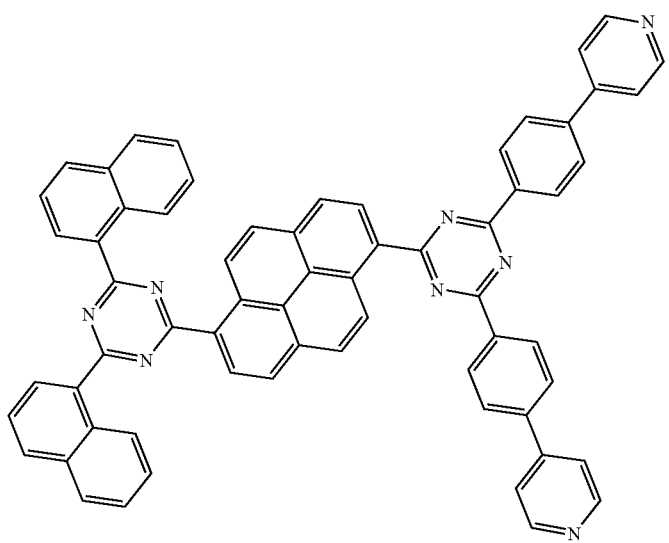

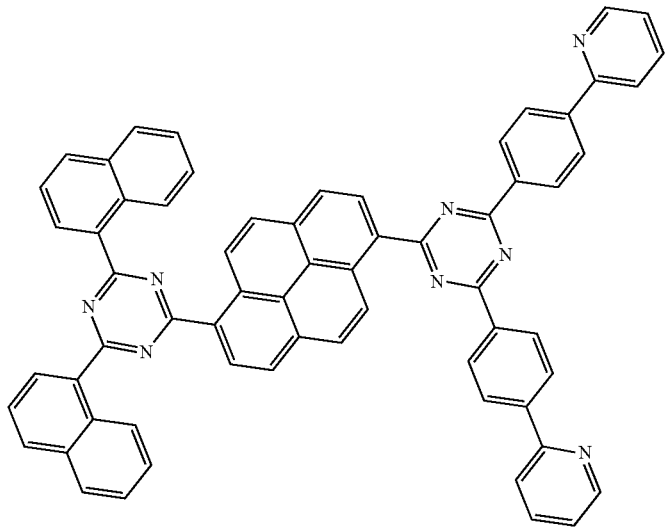
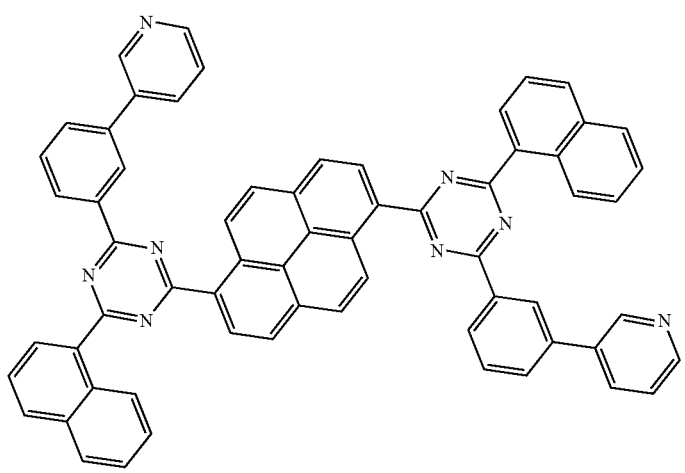
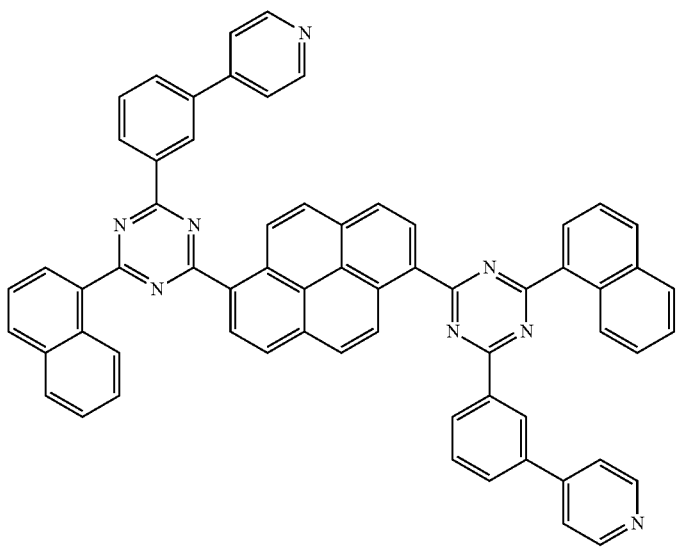

-continued
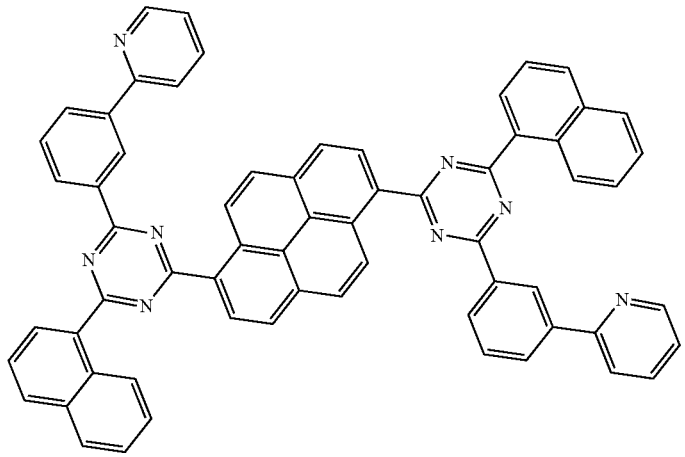
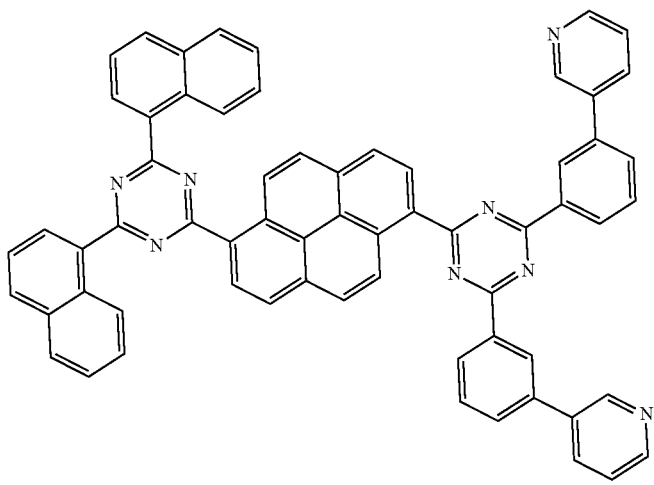
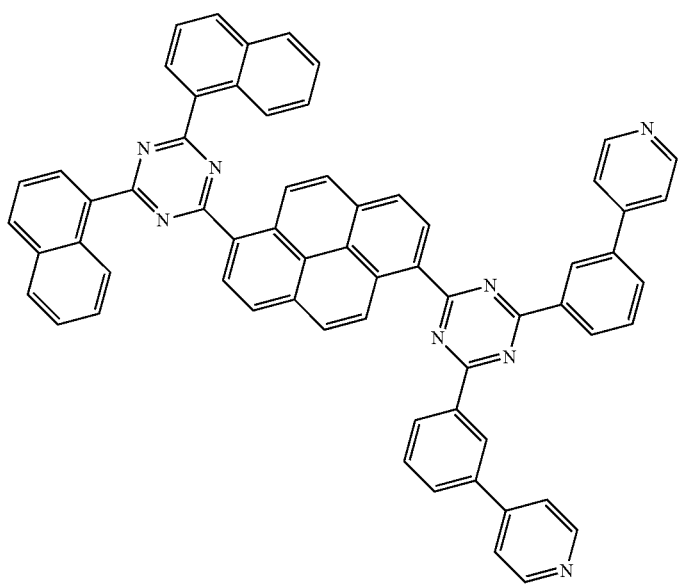

| 79 | 80 |
|---|---|
| 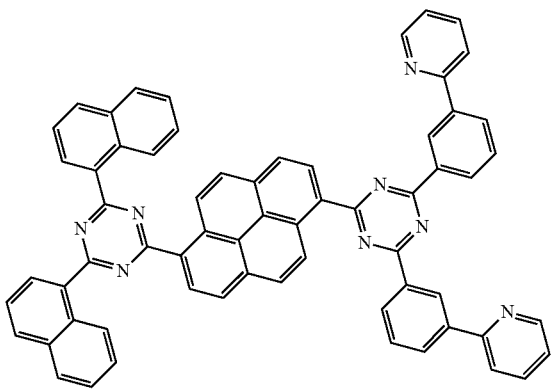 | 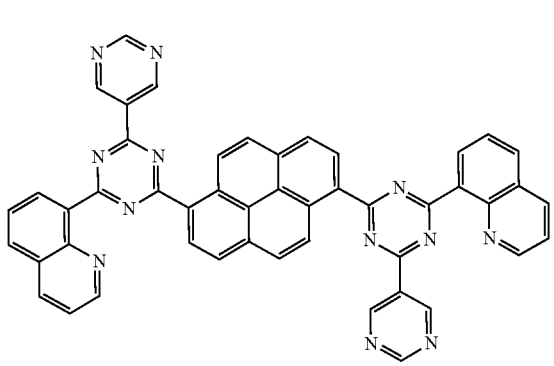 |
| 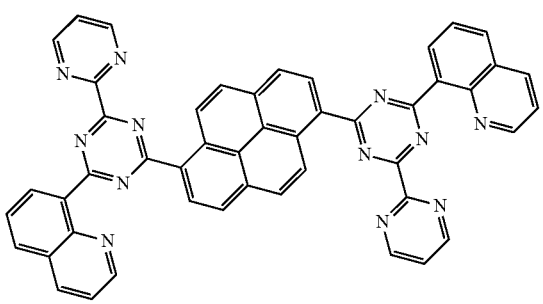 | 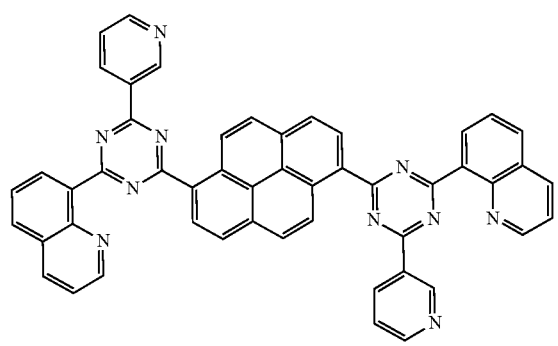 |
| 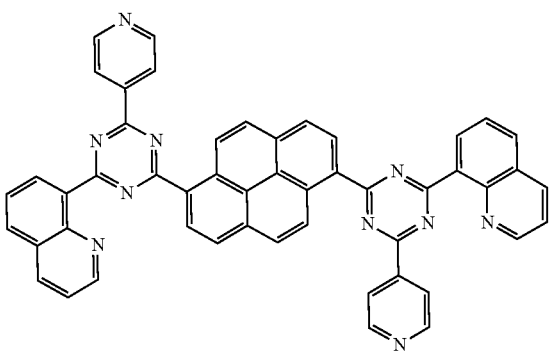 | 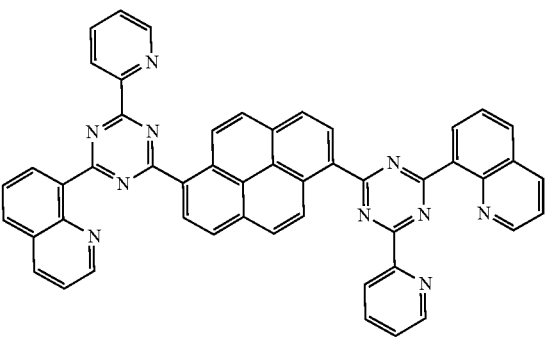 |
| 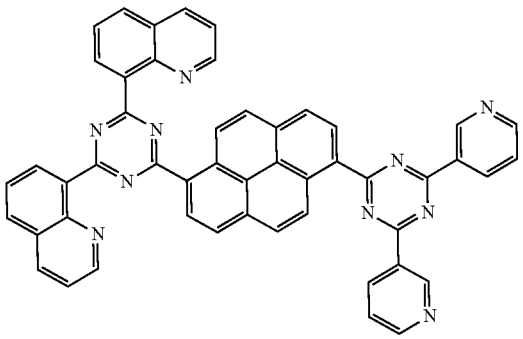 | 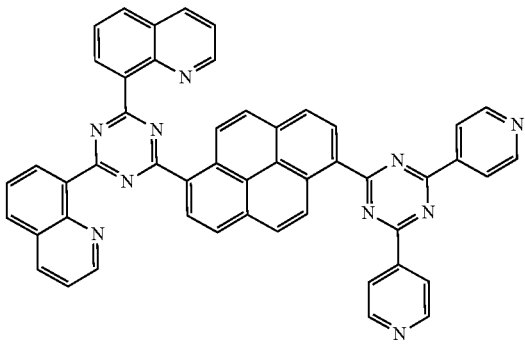 |

81
82
-continued
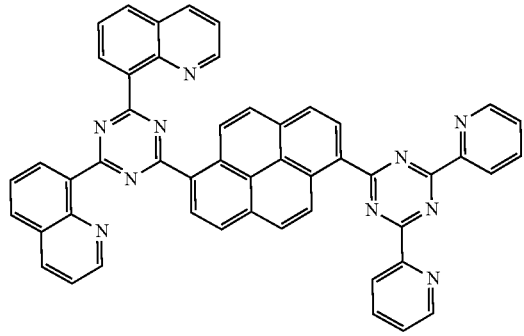
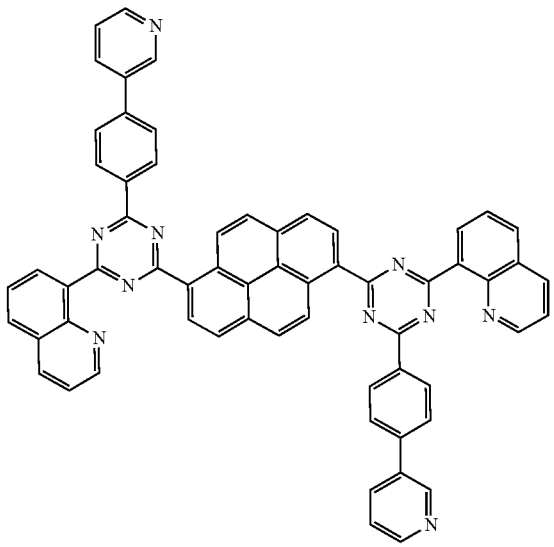
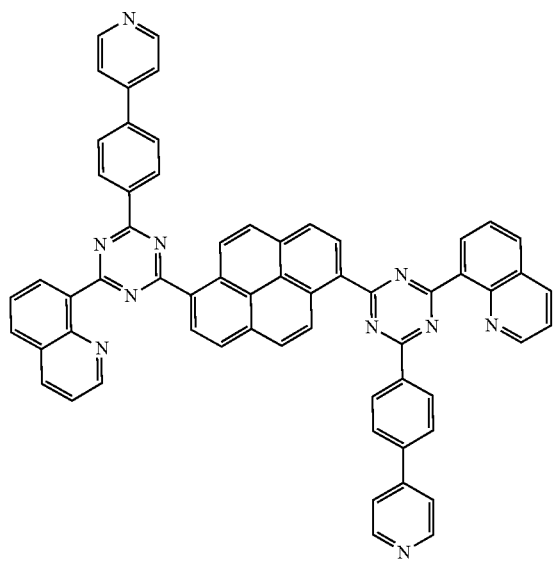
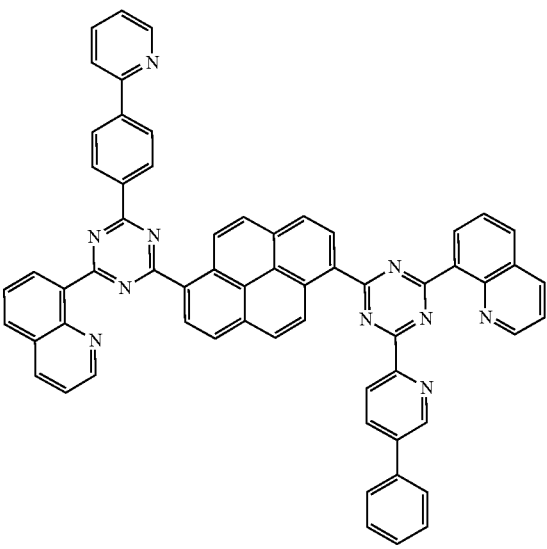
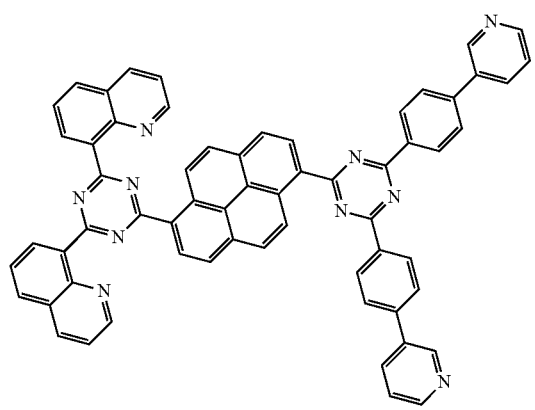
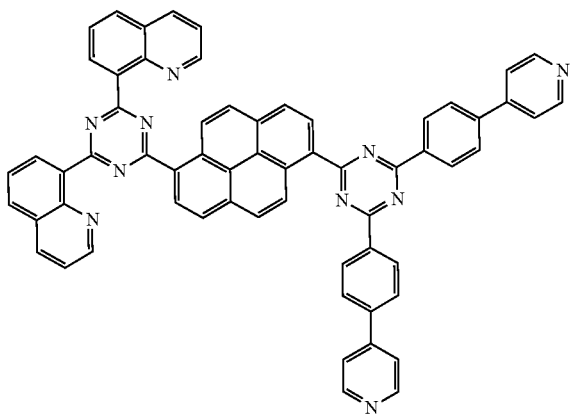

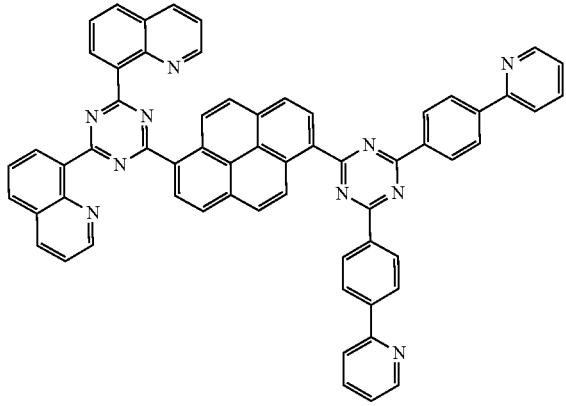
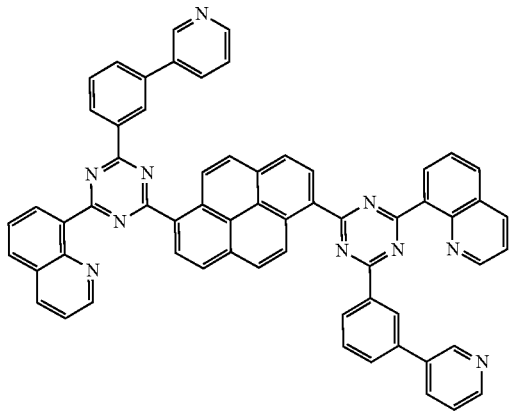
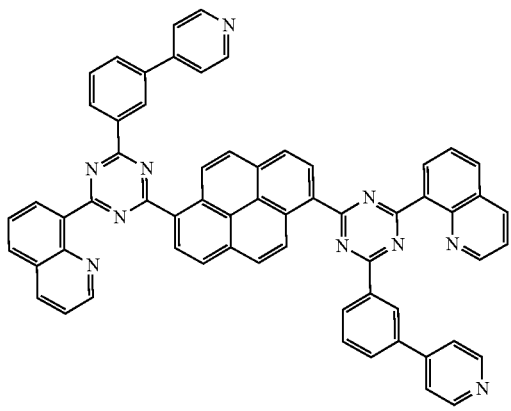
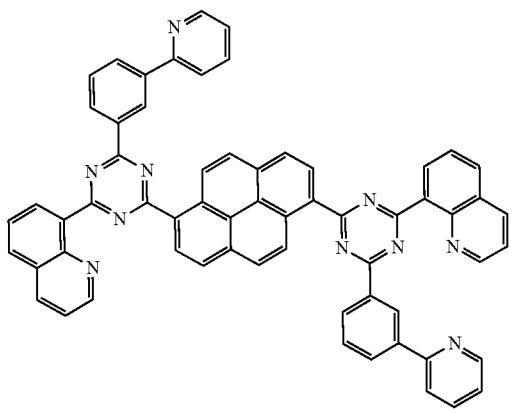
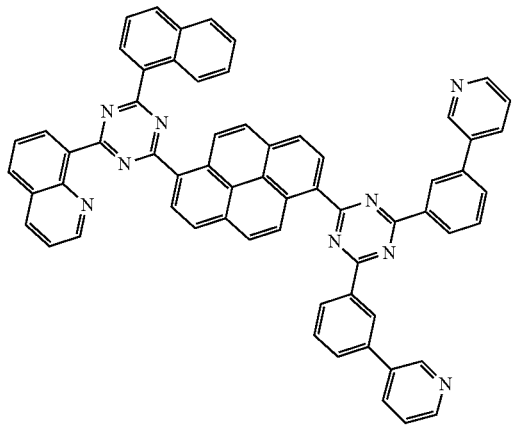
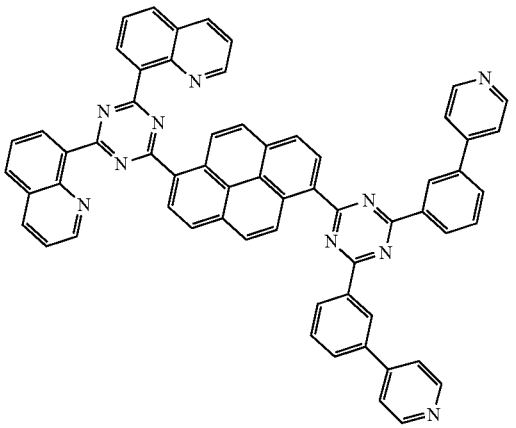
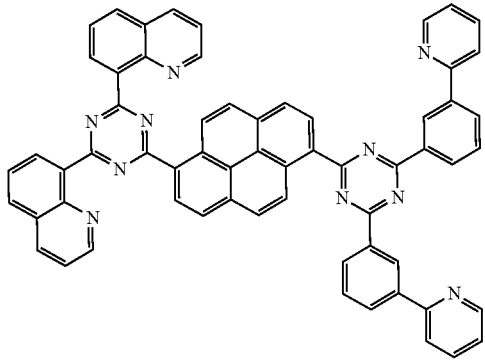
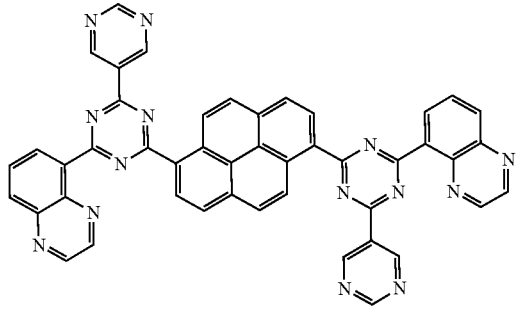

85 86
-continued
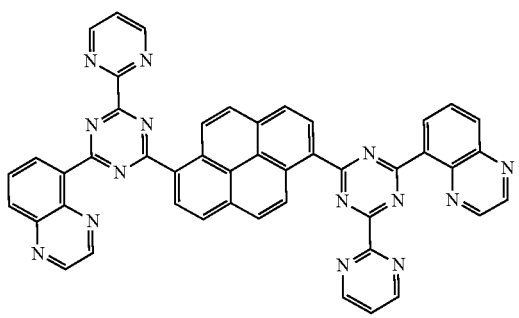
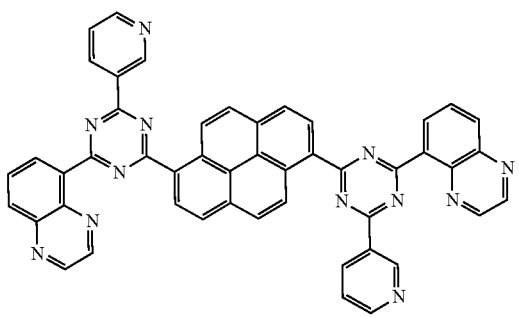
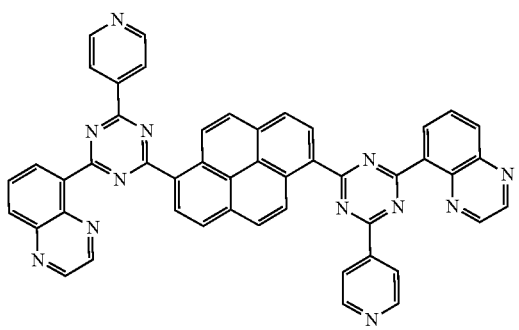
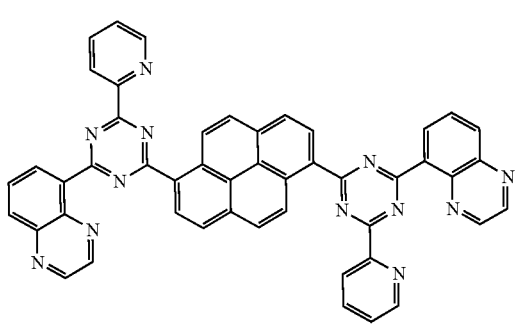
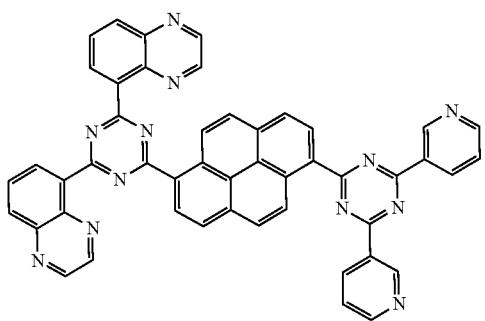
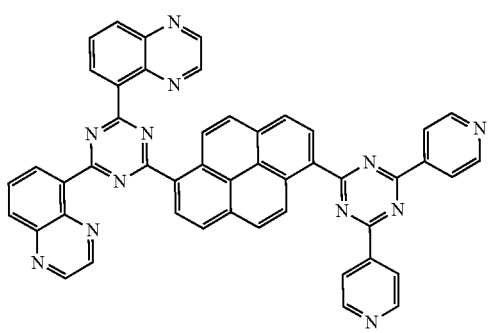
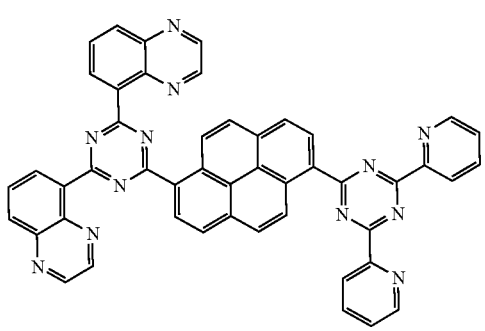
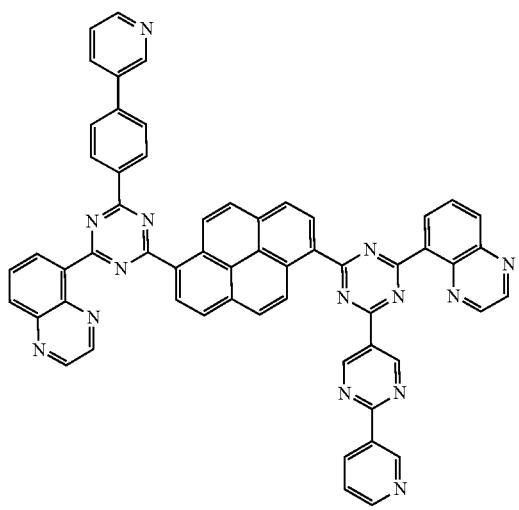

-continued
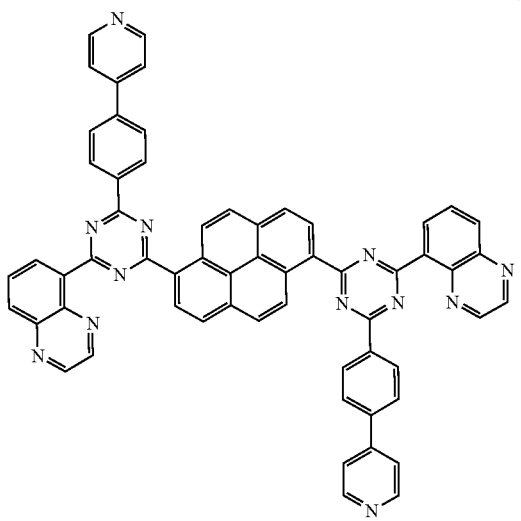
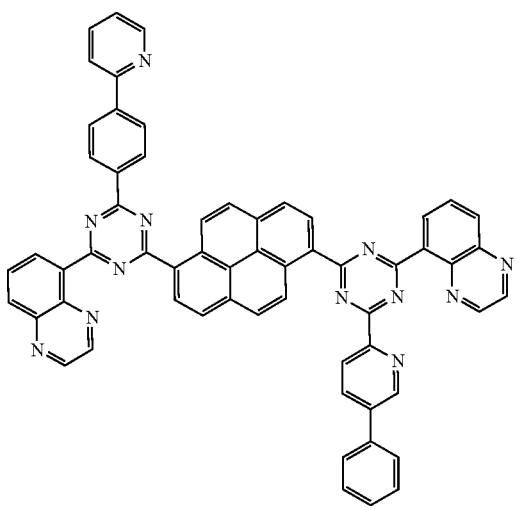
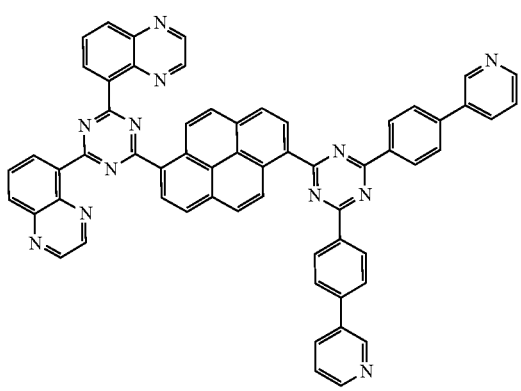
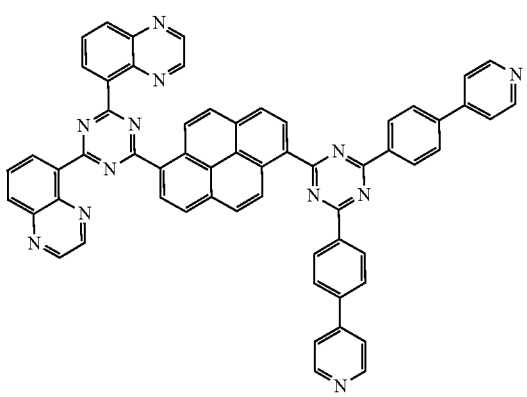
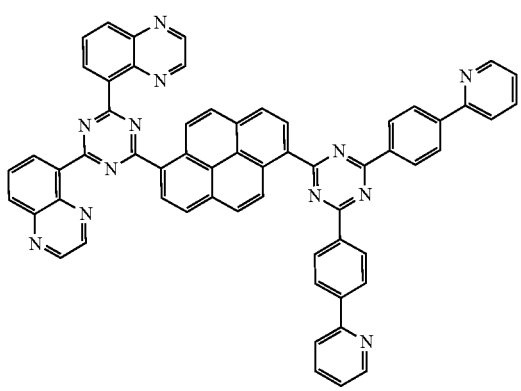
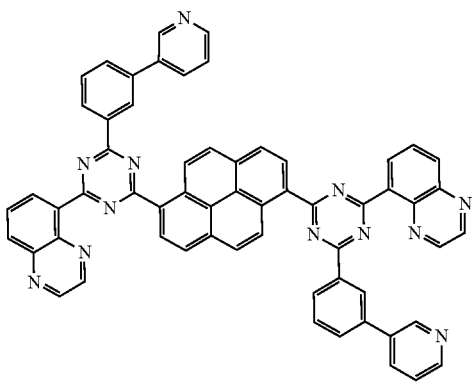
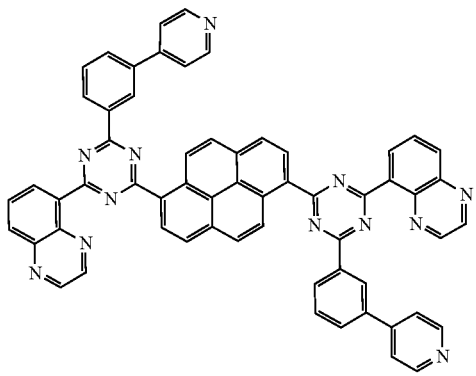
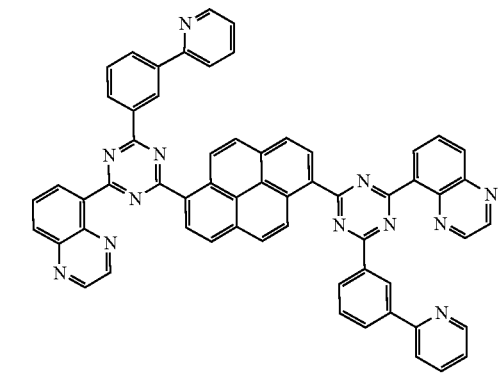

89
90
-continued
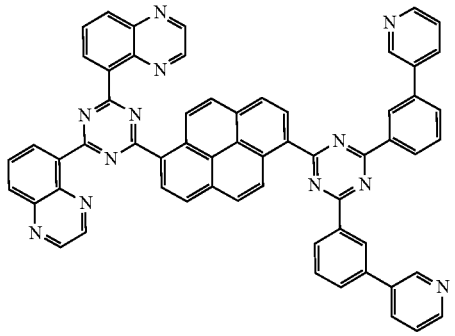
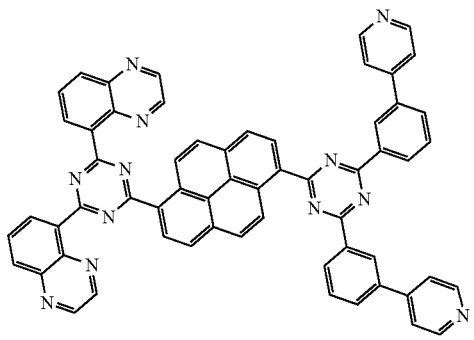
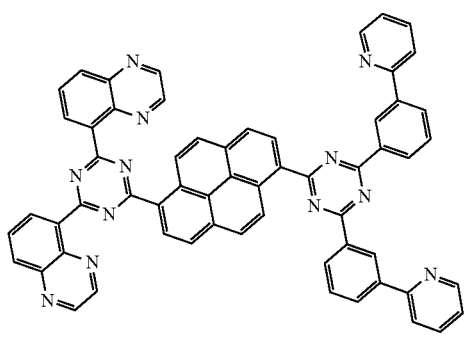
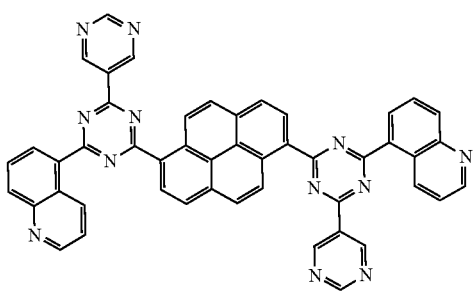
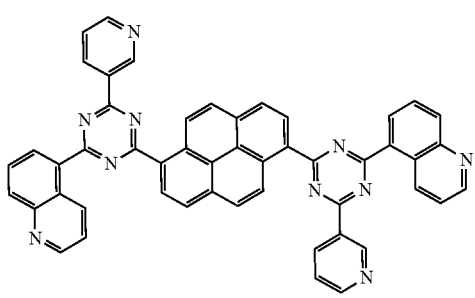
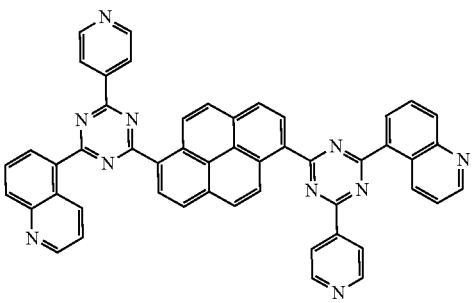
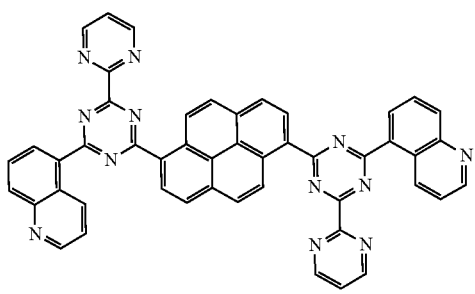
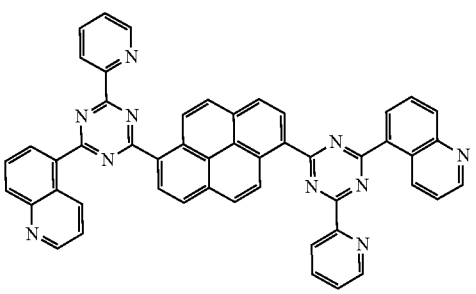
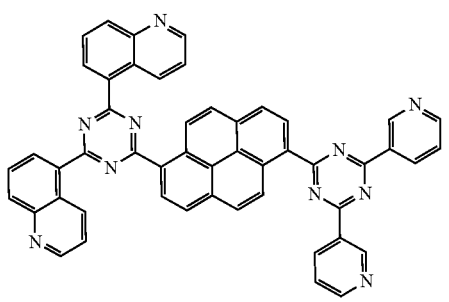
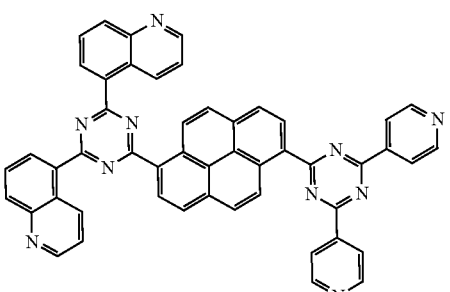

-continued
| 91 | 92 |
|---|---|
| 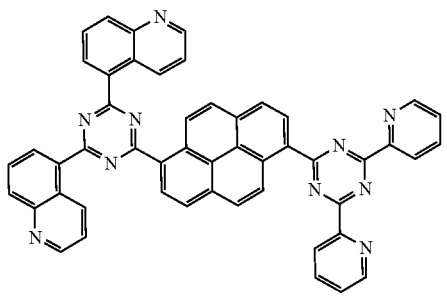 | 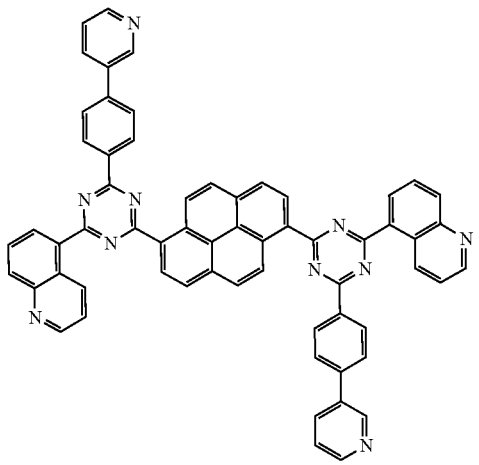 |
| 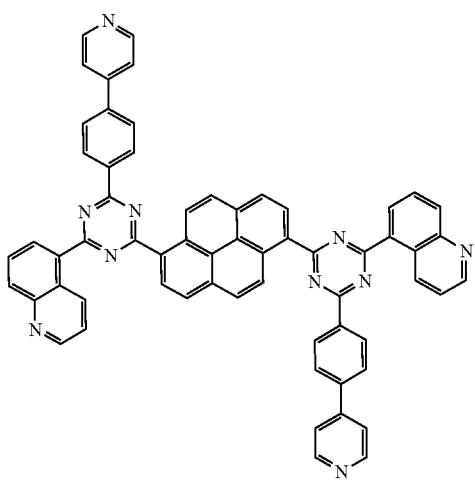 | 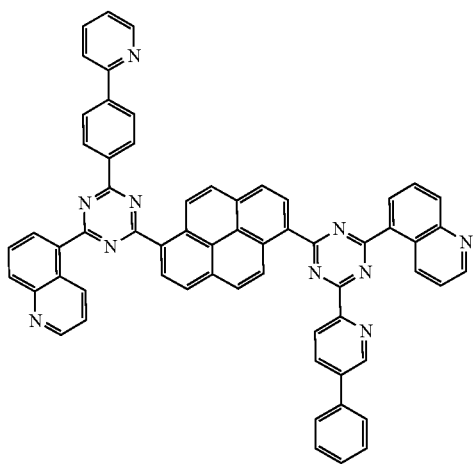 |
| 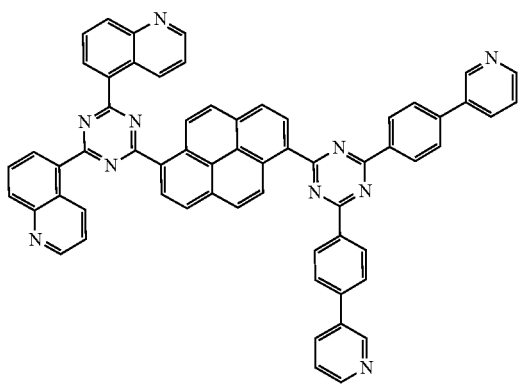 | 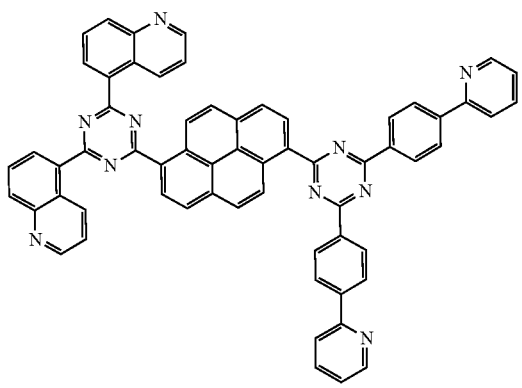 |
| 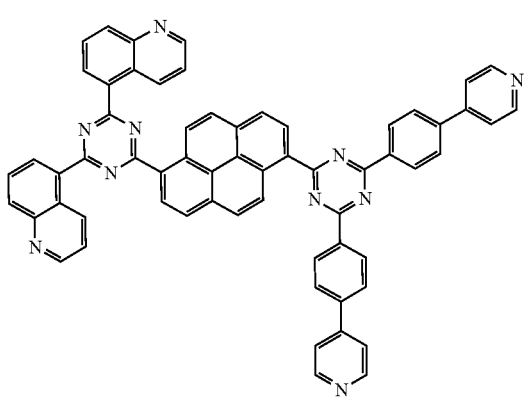 | 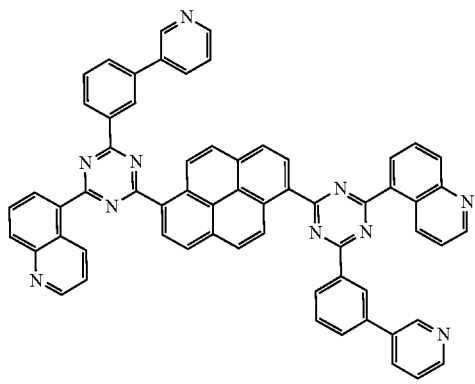 |

-continued
| 93 | 94 |
|---|---|
| 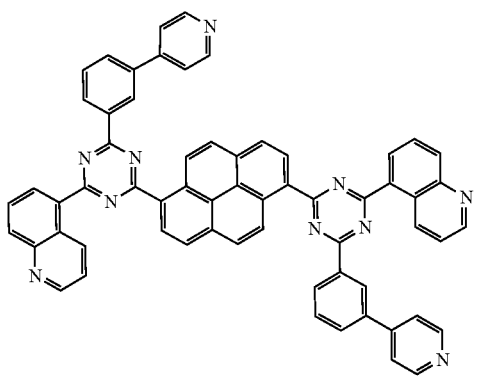 | 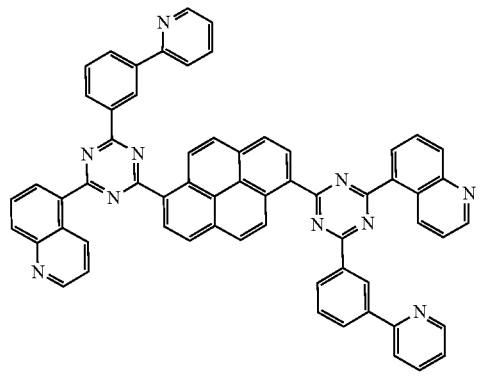 |
| 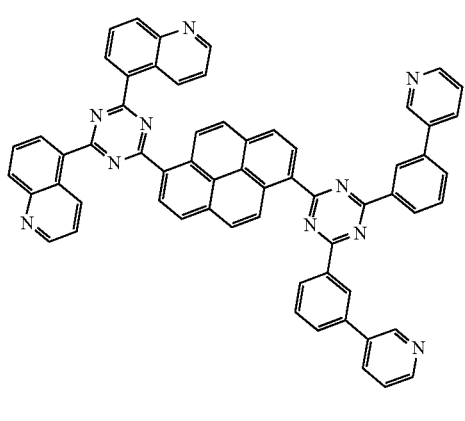 | 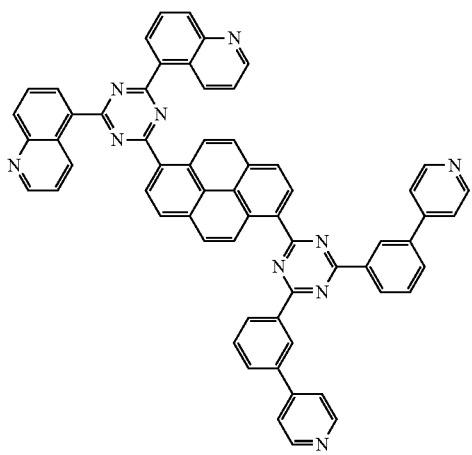 |
| 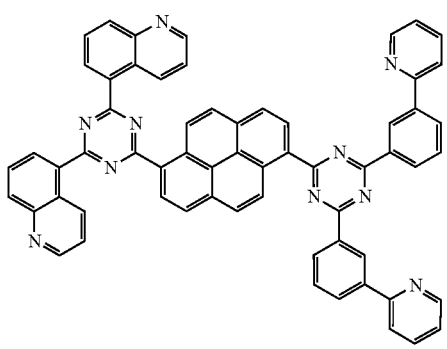 | 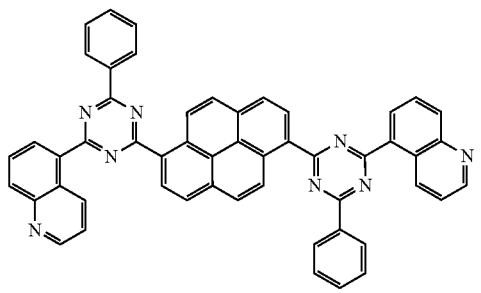 |
| 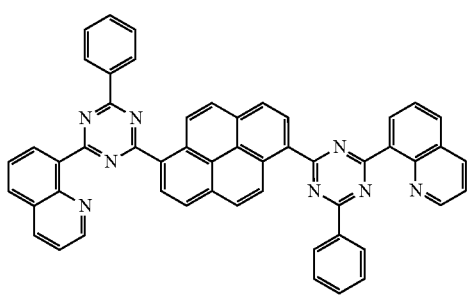 | 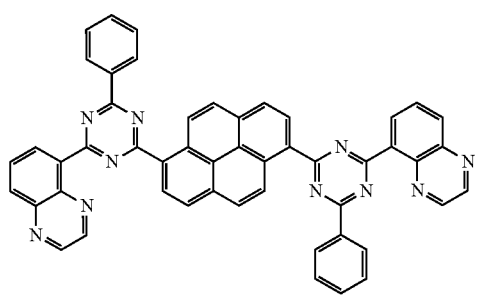 |

95
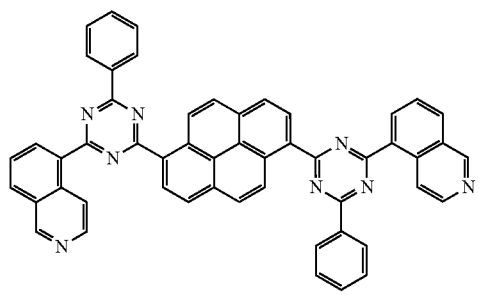
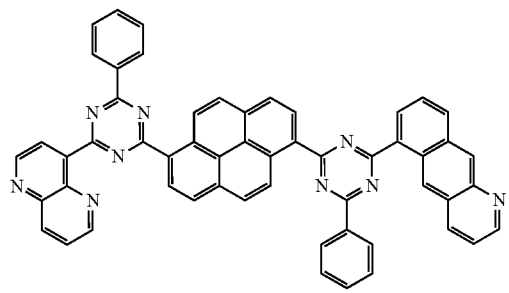
96
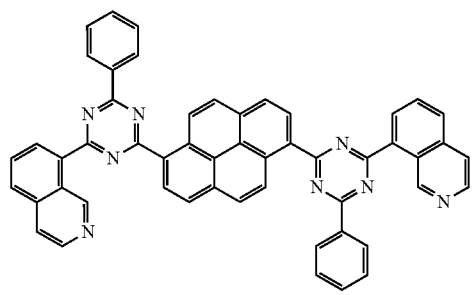
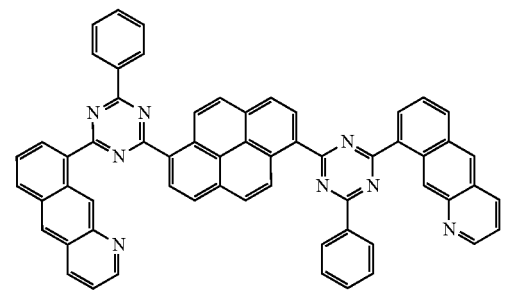
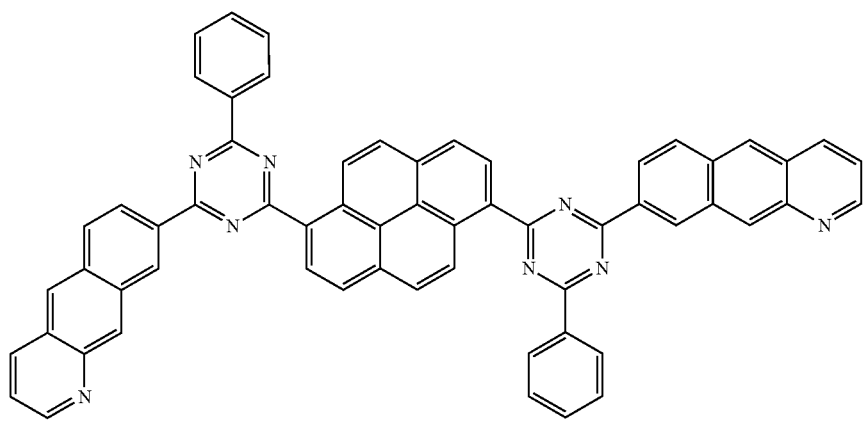
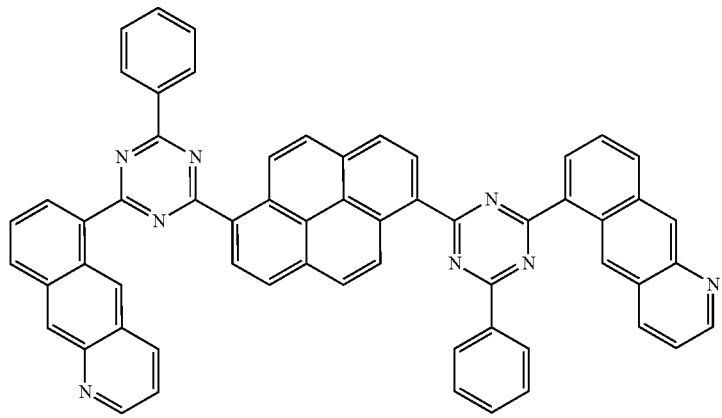

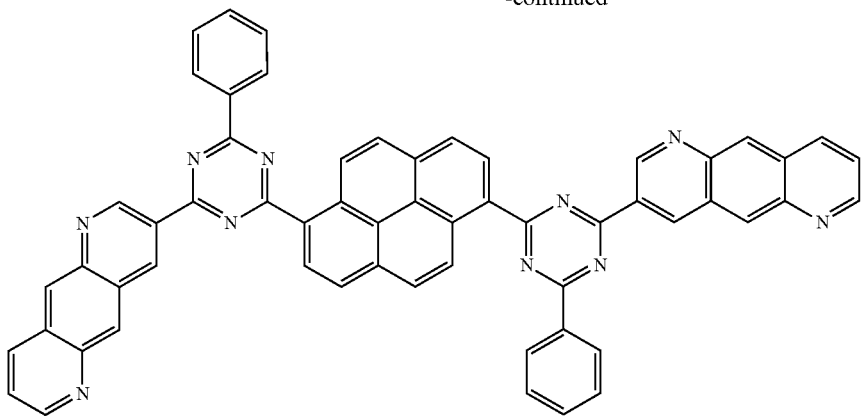

In an embodiment, the organic compound according to the present disclosure is a small molecule material.

The term "small molecule" as defined herein refers to a molecule that is not a polymer, oligomer, dendrimer, or blend. In particular, there are no repeating structures in the small molecule. The molecular weight of the small molecule is less than or equal to 3000 g/mol, further less than or equal to 2000 g/mol, and even further less than or equal to 1500 g/mol.

Polymer includes homopolymer, copolymer, and block copolymer. In addition, in the present disclosure, the polymer also includes dendrimer. The synthesis and application of dendrimers can be found in Dendrimers and Dendrons, Wiley-VCH Verlag GmbH & Co. KGaA, 2002, Ed. George R. Newkome, Charles N. Moorefield, Fritz Vogtle.

Conjugated polymer is a polymer whose backbone is primarily formed by the sp2 hybrid orbital of C atoms. Taking polyacetylene and poly (phenylene vinylene) as famous examples, the C atoms on the backbones of which may also be substituted by other non-C atoms, and which are still considered to be conjugated polymers when the sp2 hybridization on the backbones is interrupted by some natural defects. In addition, the conjugated polymer in the present disclosure may also comprise aryl amine, aryl phosphine and other heteroarmotics, organometallic complexes, and the like on the backbone.

The present disclosure also relates to a polymer comprising a repeating unit comprising a structural unit of a pyrene-triazine compound represented by the general formula (1). In certain embodiments, the polymer is a non-conjugated polymer, wherein the structural unit of the pyrene-triazine compound represented by the general formula (1) is on the side chain. In another embodiment, the polymer is a conjugated polymer.

The present disclosure also relates to a mixture comprising at least one of the organic compounds or polymers according to the present disclosure, and at least one another organic functional material.

The another organic functional material described here includes: hole (also called electronic hole) injection or transport materials (HIM/HTM), hole blocking materials (HBM), electron injection or transport materials (EIM/ETM), electron blocking materials (EBM), organic matrix material (Host), singlet emitters (fluorescent emitters), thermally activated delayed fluorescent material (TADF), triplet emitters (phosphorescent emitters), specially light-emitting organometallic complexes and organic dyes. Various organic functional materials are described in detail, for example, in WO2010135519A1, US20090134784A1 and WO2011110277A1, and the entire contents of these three patent documents are hereby incorporated herein by reference.

The organic functional materials may be small molecules or polymer materials.

In certain embodiments, in the mixture according to the present disclosure, the content of the compound is in a range from 50 wt % to 99.9 wt %, further in a range from 60 wt % to 97 wt %, still further in a range from 60 wt % to 95 wt %, even further in a range from 70 wt % to 90 wt %.

In an embodiment, the mixture according to the present disclosure comprises a compound or a polymer according to the present disclosure and a fluorescent emitting material (a singlet emitter).

In another embodiment, the mixture according to the present disclosure comprises a compound or a polymer according to the present disclosure and a thermally activated delayed fluorescent material (TADF).

In another embodiment, the mixture according to the present disclosure comprises a compound or a polymer according to the present disclosure, a fluorescent emitting material and a TADF material.

In another embodiment, the mixture according to the present disclosure comprises a compound or a polymer according to the present disclosure and another electron transport material.

The fluorescent emitting material or singlet emitter (fluorescent emitting material), and the TADF material are described in more detail below (but not limited thereto).

1. Singlet Emitter

The singlet emitter tends to have a longer conjugate π-electron system. To date, there have been many examples, such as, styrylamine and derivatives thereof disclosed in JP2913116B and WO2001021729A1, and indenofluorene and derivatives thereof disclosed in WO2008/006449 and WO2007/140847.

In an embodiment, the singlet emitter can be selected from the group consisting of mono-styrylamine, di-styrylamine, tri-styrylamine, tetra-styrylamine, styryl phosphine, styryl ether, and arylamine.

A mono-styrylamine is a compound comprising an unsubstituted or substituted styryl group and at least one amine, particularly an aromatic amine. A di-styrylamine is a compound comprising two unsubstituted or substituted styryl groups and at least one amine, particularly an aromatic amine. A tri-styrylamine is a compound comprising three unsubstituted or substituted styryl groups and at least one amine, particularly an aromatic amine. A tetra-styrylamine is a compound comprising four unsubstituted or substituted styryl groups and at least one amine, particularly an aromatic amine. In one embodiment, a styrene is stilbene, which may be further substituted. The definitions of the corresponding phosphines and ethers are similar to those of amines. An aryl amine or aromatic amine refers to a compound comprising three unsubstituted or substituted aromatic cyclic or heterocyclic systems directly coupled to nitrogen. In one embodiment, at least one of such aromatic or heterocyclic ring systems is selected from fused ring system, and particularly has at least 14 aromatic ring atoms. Suitable examples are aromatic anthramine, aromatic anthradiamine, aromatic pyrenamine, aromatic pyrenediamine, aromatic chryseneamine or aromatic chrysenediamine. An aromatic anthramine refers to a compound in which a diarylamino group is directly coupled to anthracene, particularly at position 9. An aromatic anthradiamine refers to a compound in which two diarylamino groups are directly coupled to anthracene, particularly at positions 9, 10. Aromatic pyrenamine, aromatic pyrenediamine, aromatic chryseneamine and aromatic chrysenediamine are similarly defined, wherein the diarylamino group is particularly coupled to position 1 or 1, 6 of pyrene.

The examples of singlet emitters based on vinylamine and arylamine are also suitable examples which may be found in the following patent documents: WO 2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1 957 606 A1 and US 2008/0113101 A1, the entirety of the patent documents listed above are hereby incorporated herein by reference.

Examples of singlet emitters based on stilbene and derivatives thereof can be found in U.S. Pat. No. 5,121,029.

Further suitable singlet emitters may be selected from indenofluorene-amine and indenofluorene-diamine, as disclosed in WO 2006/122630, benzoindenofluorene-amines and benzoindenofluorene-diamine, as disclosed in WO 2008/006449, dibenzoindenofluorene-amine and dibenzofluorenone-diamine, as disclosed in WO2007/140847.

Other materials that may be used as singlet emitters are polycyclic aromatic hydrocarbon compounds, particularly the derivatives of the following compounds: anthracene such as 9,10-di(2-naphthanthracene), naphthalene, tetracene, xanthene, phenanthrene, pyrene (such as 2,5,8,11-tetra-t-butylperylene), indenopyrene, phenylene (such as 4,4'-(bis (9-ethyl-3-carbazovinylene)-1,1'-biphenyl), periflanthene, decacyclene, coronene, fluorene, spirobifluorene, arylpyrene (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4 (dicyanomethylene)-6-(4-dimethylaminostyryl-2-methyl)-4H-pyrane (DCM), thiapyran, bis (azinyl) imine-boron compound (US 2007/0092753 A1), bis (azinyl) methene compound, carbostyryl compound, oxazone, benzoxazole, benzothiazole, benzimidazole and diketopyrrolopyrrole. Examples of materials of some singlet emitters can be found in the following patent documents: US 20070252517 A1, U.S. Pat. Nos. 4,769,292, 6,020,078, US 2007/0252517 A1, US 2007/0252517 A1. The entirety of the patent documents listed above is hereby incorporated herein by reference.

Examples of suitable singlet emitters are listed in table below:

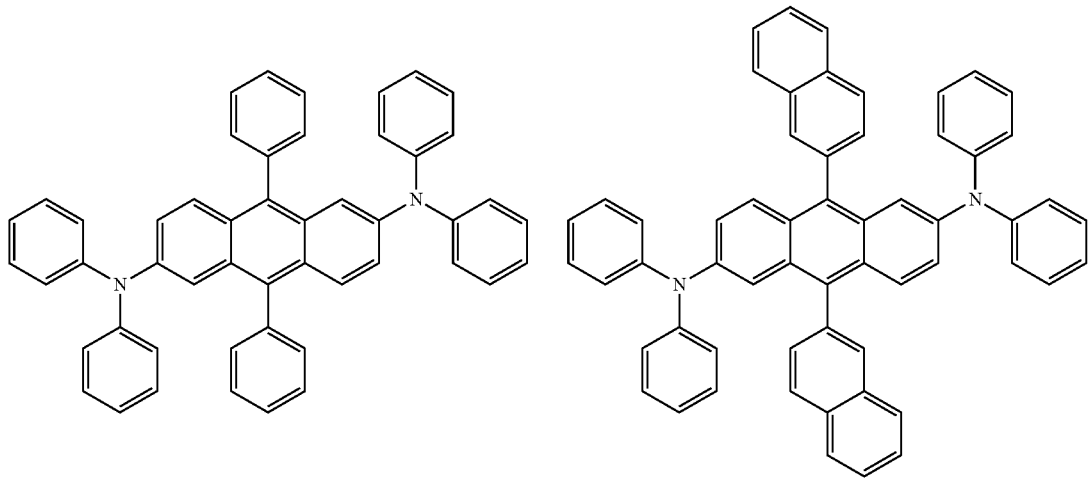

101 102
-continued
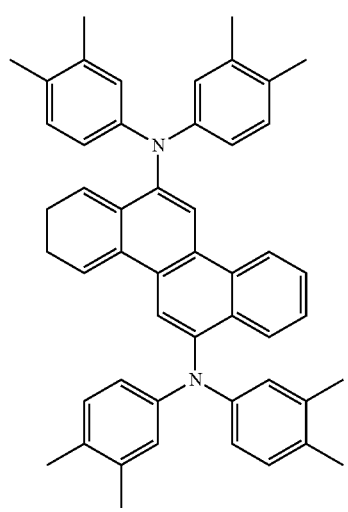
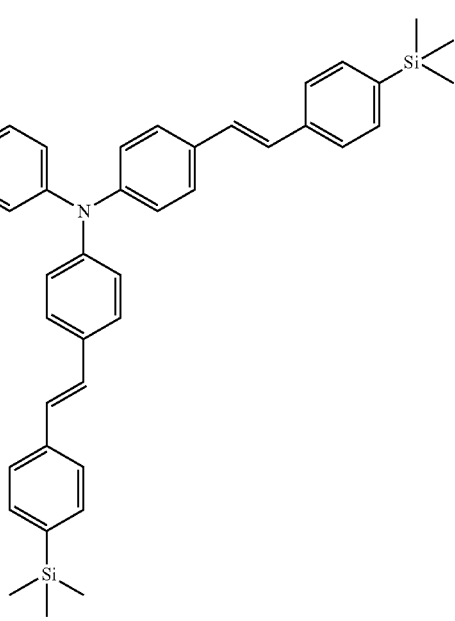
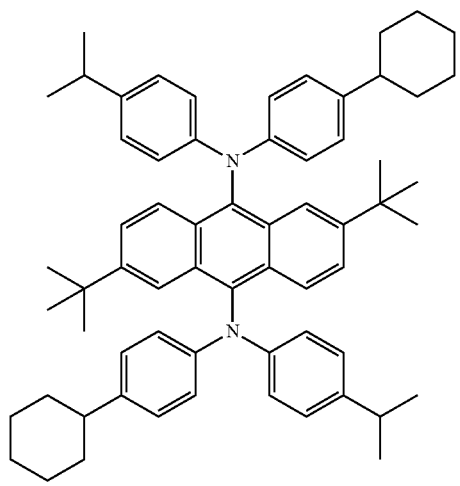
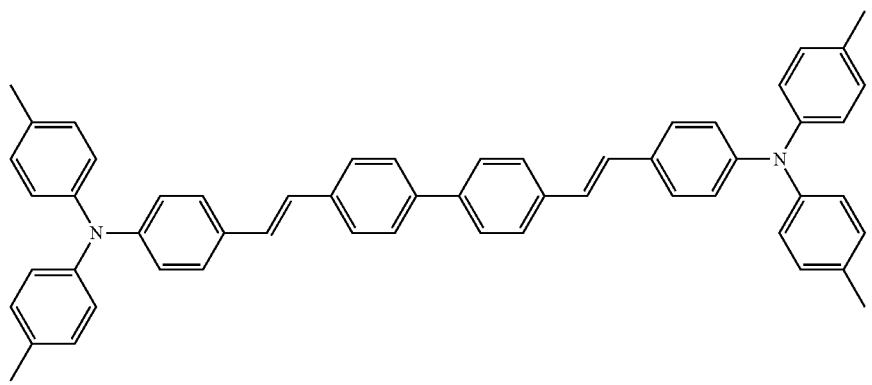

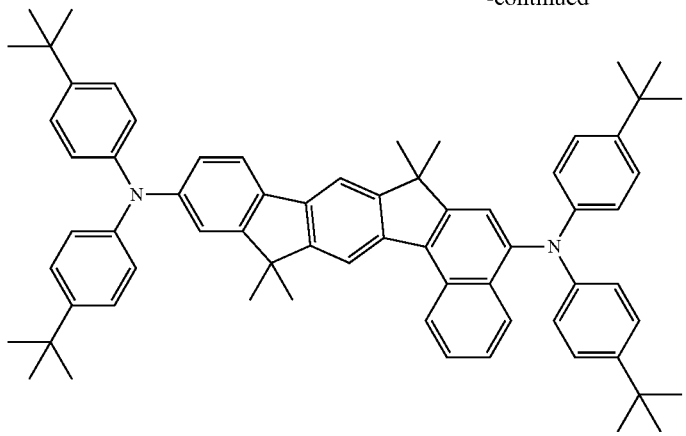

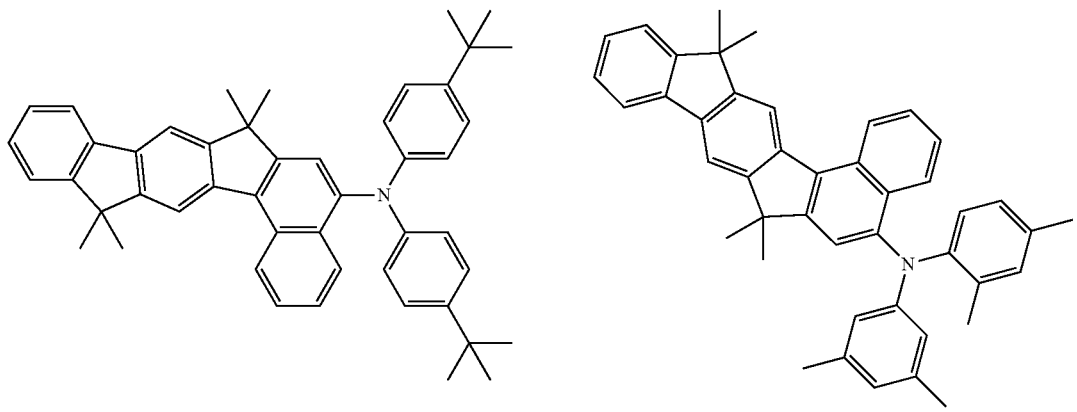

2. Thermally Activated Delayed Fluorescent Materials (TADF):

Traditional organic fluorescent materials can only emit light using 25% singlet exciton formed by electrical excitation, and the devices have relatively low internal quantum efficiency (up to 25%). The phosphorescent material enhances the intersystem crossing due to the strong spin-orbit coupling of the heavy atom center, the singlet exciton and the triplet exciton formed by the electric excitation can be effectively utilized to emit light, so that the internal quantum efficiency of the device can reach 100%. However, the phosphor materials are expensive, the material stability is poor, and the device efficiency roll-off is a serious problem, which limit its application in OLED. The thermally activated delayed fluorescent material is the third generation of organic light-emitting material developed after the organic fluorescent material and the organic phosphorescent material. This type of materials generally have a small singlet-triplet excited state energy level difference (ΔEst), and triplet excitons can be converted to singlet excitons by intersystem crossing to emit light. Thus, singlet excitons and triplet excitons formed under electric excitation can be fully utilized. The internal quantum efficiency of the device can reach 100%.

The TADF material needs to have a smaller singlet-triplet energy level difference, typically ΔEst<0.3 eV, further ΔEst<0.2 eV, still further ΔEst<0.1 eV, and even further ΔEst<0.05 eV. In an embodiment, TADF has better fluorescence quantum efficiency. Some TADF materials can be found in the following patent documents: CN103483332(A), TW201309696(A), TW201309778(A), TW201343874(A), TW201350558(A), US20120217869(A1), WO2013133359 (A1), WO2013154064(A1), Adachi, et. al. Adv. Mater., 21, 2009, 4802, Adachi, et. al. Appl. Phys. Lett., 98, 2011, 083302, Adachi, et. al. Appl. Phys. Lett., 101, 2012, 093306, Adachi, et. al. Chem. Commun., 48, 2012, 11392, Adachi, et. al. Nature Photonics, 6, 2012, 253, Adachi, et. al. Nature, 492, 2012, 234, Adachi, et. al. J. Am. Chem. Soc, 134, 2012, 14706, Adachi, et. al. Angew. Chem. Int. Ed, 51, 2012, 11311, Adachi, et. al. Chem. Commun., 48, 2012, 9580, Adachi, et. al. Chem. Commun., 48, 2013, 10385, Adachi, et. al. Adv. Mater., 25, 2013, 3319, Adachi, et. al. Adv. Mater., 25, 2013, 3707, Adachi, et. al. Chem. Mater., 25, 2013, 3038, Adachi, et. al. Chem. Mater., 25, 2013, 3766, Adachi, et. al. J. Mater. Chem. C., 1, 2013, 4599, Adachi, et. al. J. Phys. Chem. A., 117, 2013, 5607, the contents of the above-listed patents or article documents are hereby incorporated herein by reference in their entirety.

Some examples of suitable TADF light-emitting materials are listed in the table below:

105 106
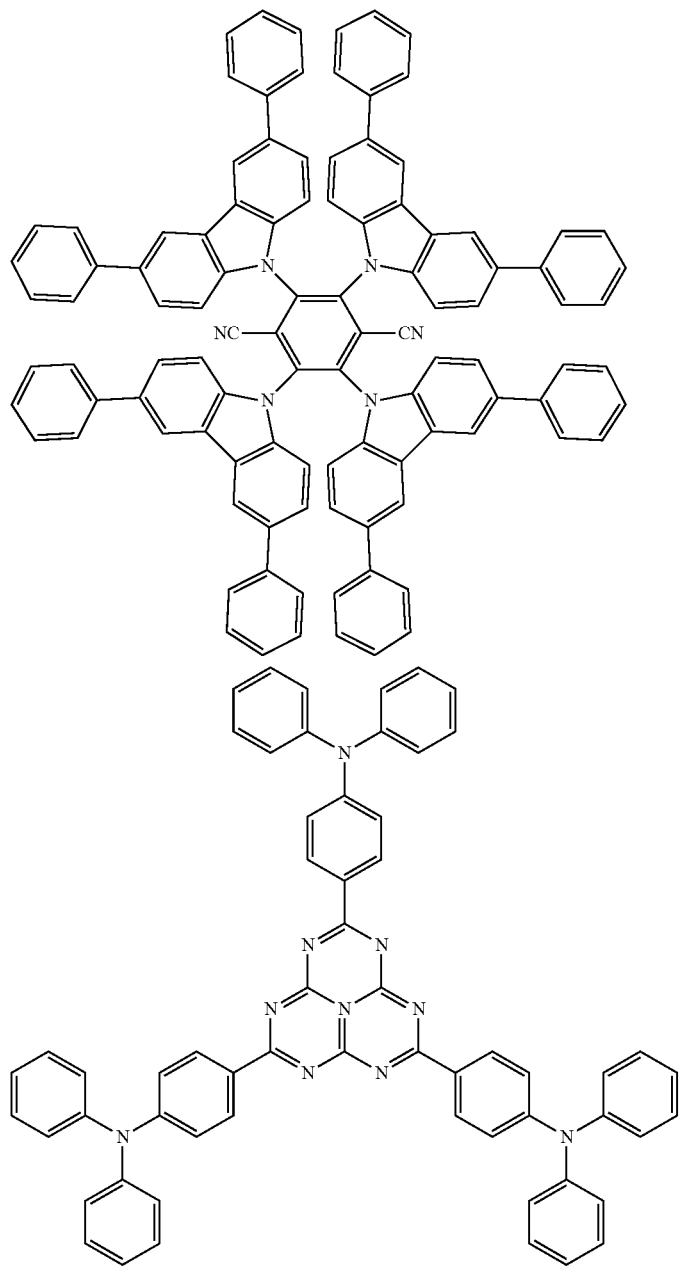 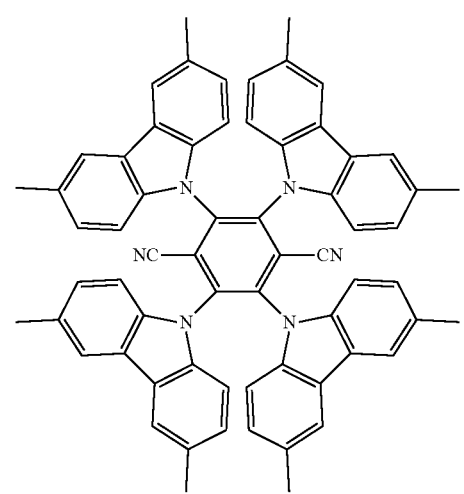

107 108
-continued
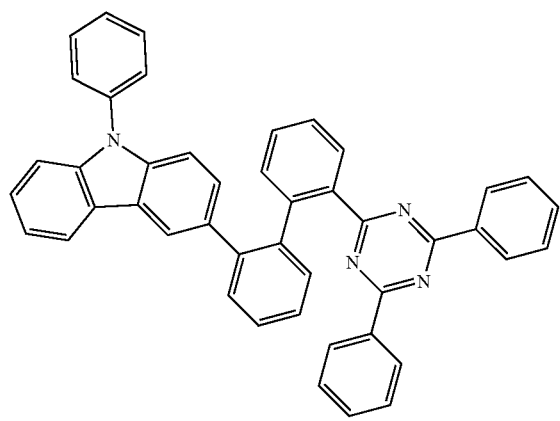
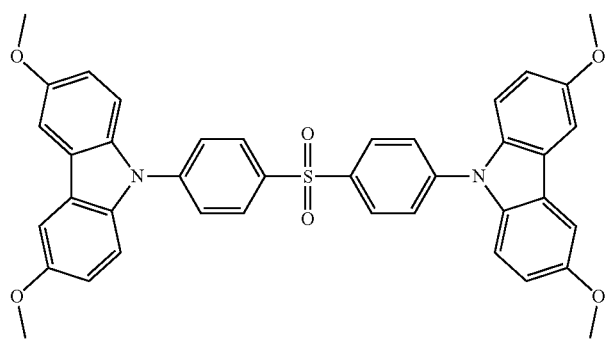
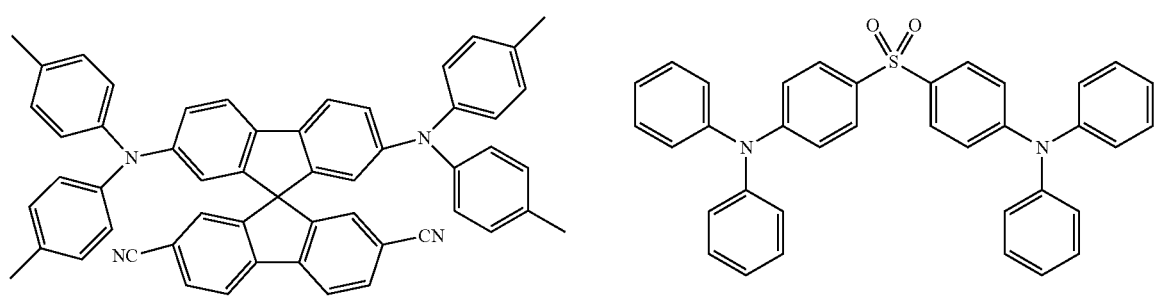
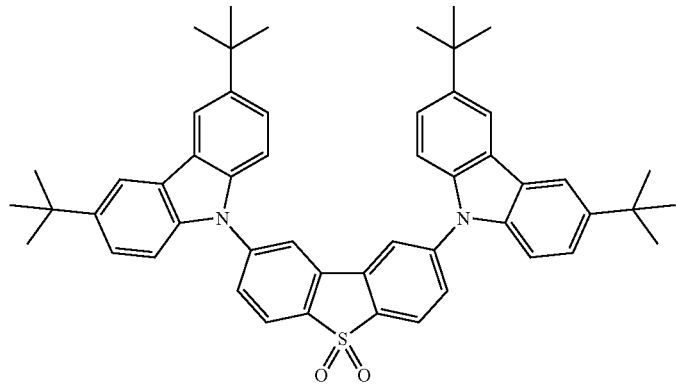

-continued
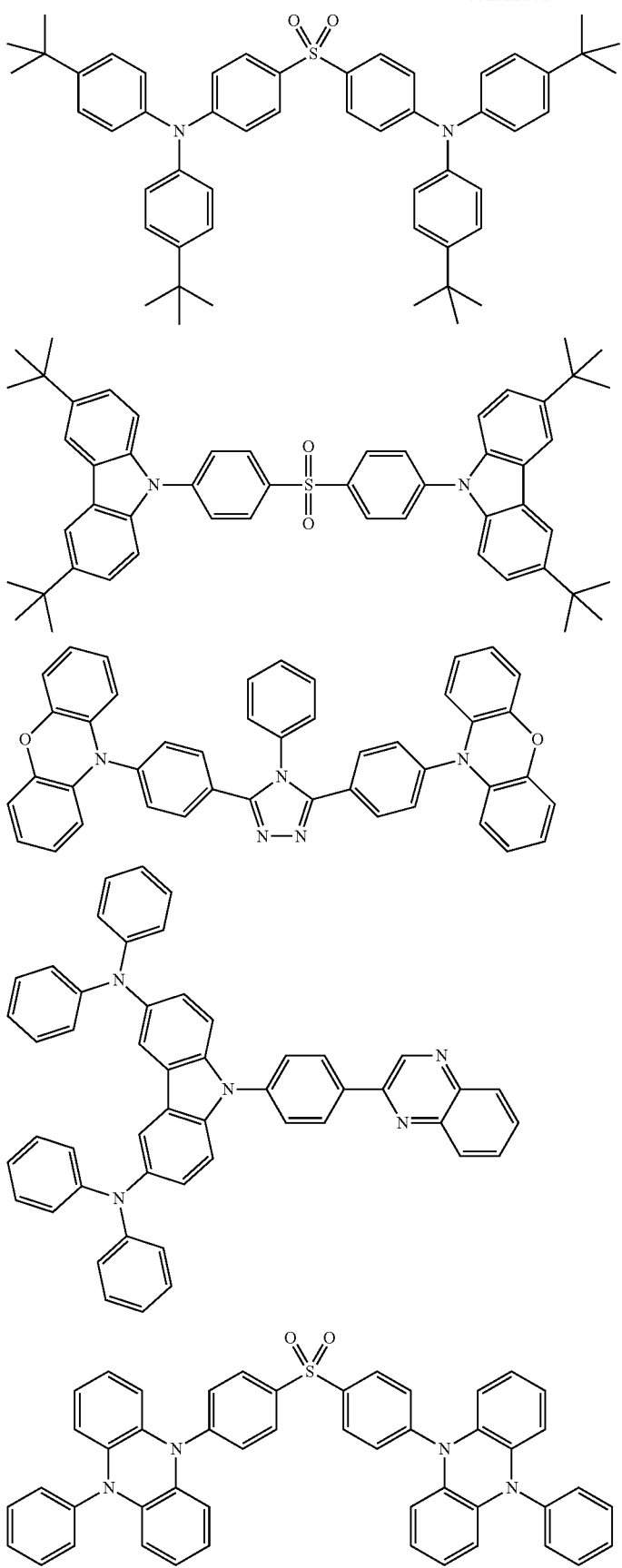

111 112
-continued
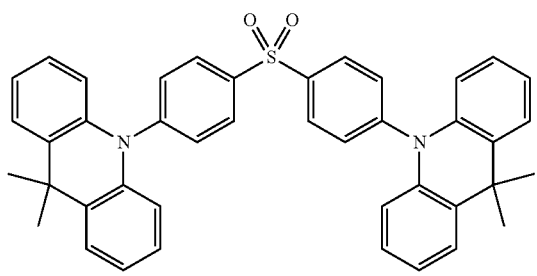
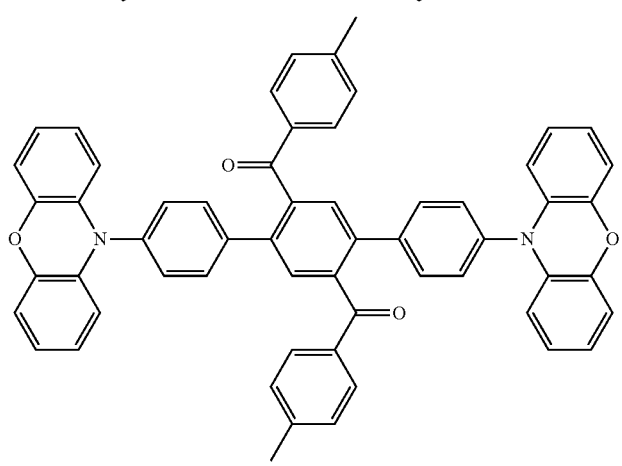
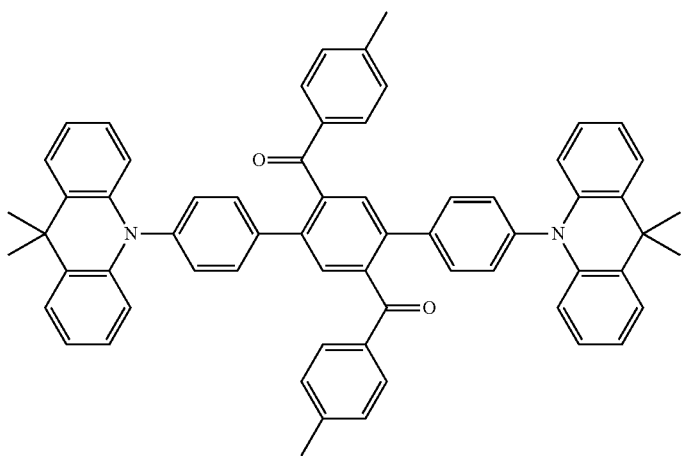
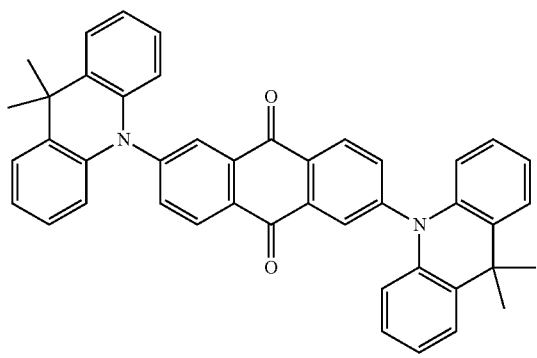 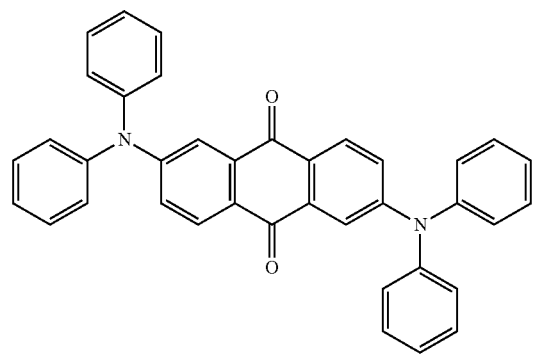

113 114
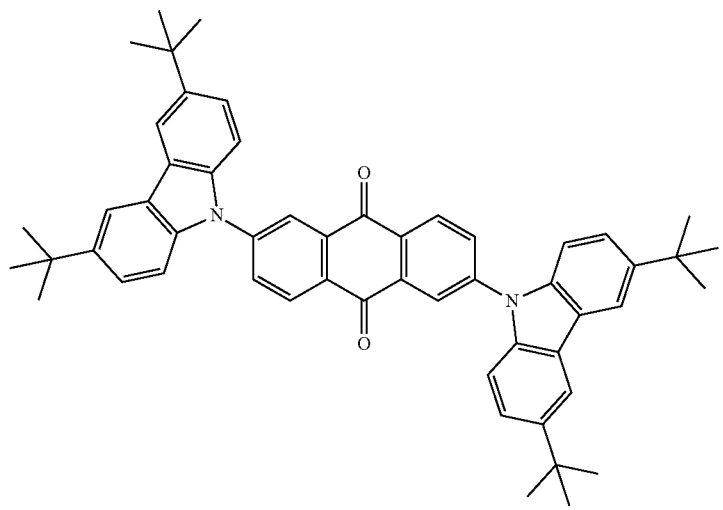
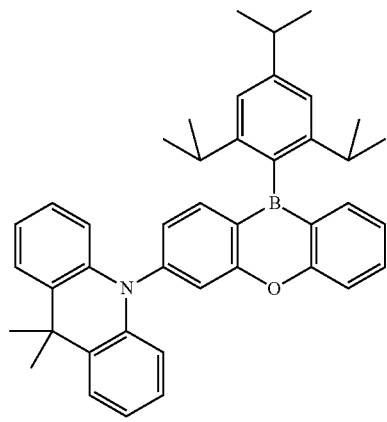
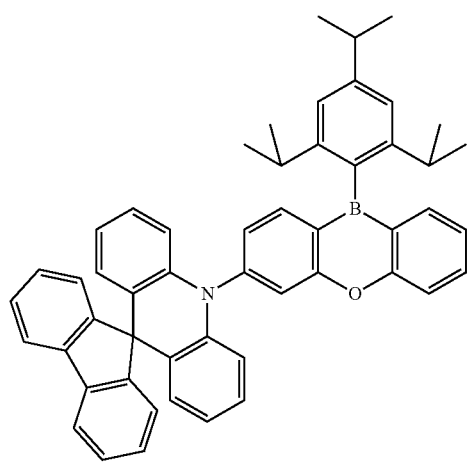
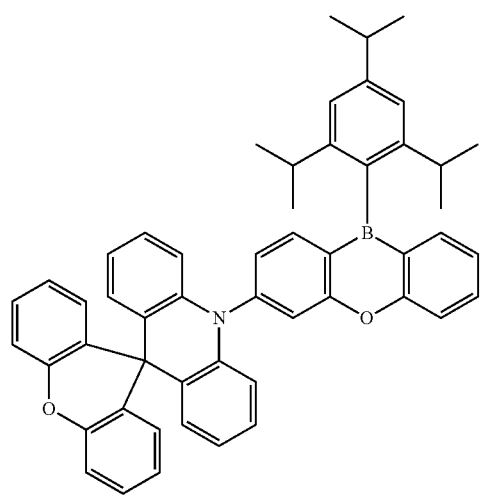
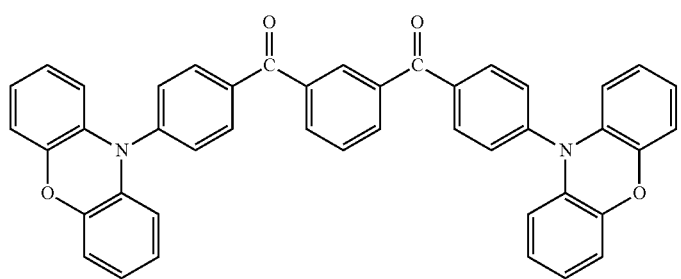
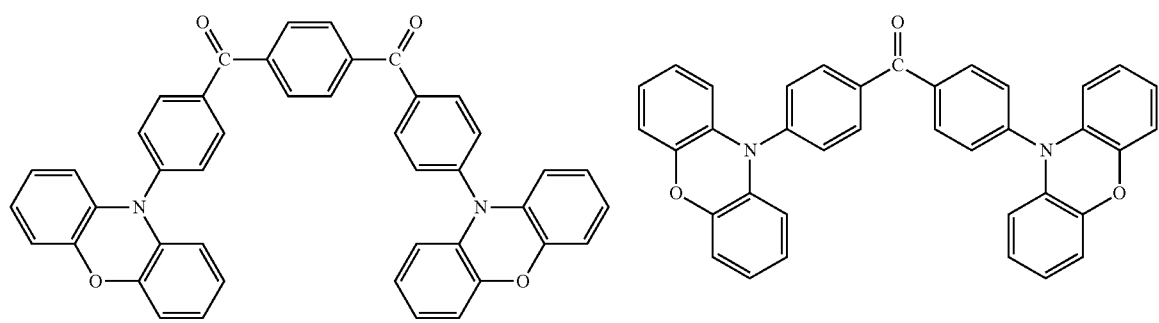

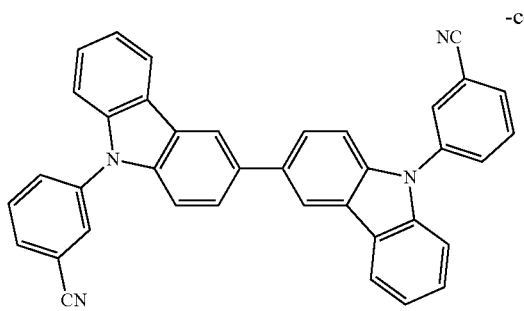

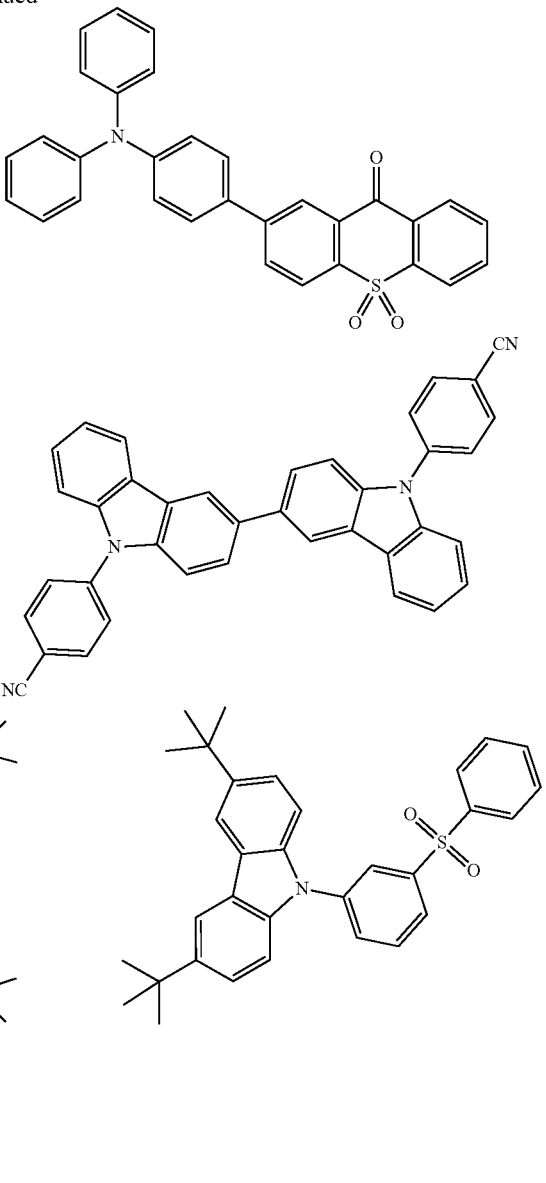

The publications of organic functional materials mentioned above are incorporated herein by reference for the purpose of disclosure.

In an embodiment, the compound according to the present disclosure is used for evaporated OLED devices. For this purpose, the compound according to the present disclosure has a molecular weight≤1000 g/mol, further≤900 g/mol, still further≤850 g/mol, still further≤800 g/mol, even further≤700 g/mol.

Another purpose of the present disclosure is to provide material solutions for printing OLED.

In certain embodiments, the compound according to the present disclosure has a molecular weight≥700 g/mol, further≥800 g/mol, still further≥900 g/mol, still further≥1000 g/mol, even further≥1100 g/mol.

In other embodiments, the compound according to the present disclosure has solubility in toluene≥10 mg/mL, further≥15 mg/mL, and even further≥20 mg/mL at 25° C.

The present disclosure further relates to a formulation or ink which comprises a compound or a polymer or a mixture according to the present disclosure, and at least one organic solvent. The present disclosure further provides a thin film comprising the compound or polymer according to the present disclosure prepared from a solution.

The viscosity and surface tension of ink are important parameters when the ink is used in the printing process. The suitable surface tension parameters of ink are suitable for a particular substrate and a particular printing method.

In an embodiment, the surface tension of the ink according to the present disclosure at working temperature or at 25° C. is in the range of about 19 dyne/cm to 50 dyne/cm, further in the range of 22 dyne/cm to 35 dyne/cm, and still further in the range of 25 dyne/cm to 33 dyne/cm.

In another embodiment, the viscosity of the ink according to the present disclosure at the working temperature or at 25° C. is in the range of about 1 cps to 100 cps, further in the range of 1 cps to 50 cps, still further in the range of 1.5 cps to 20 cps, and even further in the range of 4.0 cps to 20 cps. The formulation so formulated will be suitable for inkjet printing.

The viscosity can be adjusted by different methods, such as by the selection of appropriate solvent and the concentration of functional materials in the ink. The ink according to the present disclosure comprising the compound or the polymer can facilitate the adjustment of the printing ink in an appropriate range according to the printing method used. In general, the weight ratio of the functional material contained in the formulation according to the present disclosure is in the range of 0.3 wt % to 30 wt %, further in the range of 0.5 wt % to 20 wt %, still further in the range of 0.5 wt % to 15 wt %, still further in the range of 0.5 wt % to 10 wt %, and even further in the range of 1 wt % to 5 wt %.

In some embodiments, according to the ink of the present disclosure, the at least one organic solvent is selected from aromatic or heteroaromatic based on solvents, in particular from aromatic solvents or aromatic ketone solvents or aromatic ether solvents substituted by aliphatic chain/ring.

Examples suitable for solvents of the present disclosure include, but not limited to, aromatic or heteroaromatic based on solvents: p-diisopropylbenzene, pentylbenzene, tetrahydronaphthalene, cyclohexyl benzene, chloronaphthalene, 1,4-dimethylnaphthalene, 3-isopropylbiphenyl, p-cymene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-cymene, 1-methylnaphthalene, 1,2,4-trichlorobenzene, 1,3-dipropoxybenzene, 4,4-difluorodiphenylmethane, 1,2-dimethoxy-4-(1-propenyl)benzene, diphenylmethane, 2-phenylpyridine, 3-phenylpyridine, N-methyldiphenylamine 4-isopropylbiphenyl, α,α-dichlorodiphenylmethane, 4-(3-phenylpropyl)pyridine, benzylbenzoate, 1,1-di(3,4-dimethylphenyl)ethane, 2-isopropylnaphthalene, dibenzylether, and the like; solvents based on ketones: 1-tetralone, 2-tetralone, 2-(phenylepoxy)tetralone, 6-(methoxyl)tetralone, acetophenone, phenylacetone, benzophenone, and derivatives thereof, such as 4-methylacetophenone, 3-methylacetophenone, 2-methylacetophenone, 4-methylphenyl acetone, 3-methylphenylacetone, 2-methylphenyl acetone, isophorone, 2,6,8-trimethyl-4-nonanone, fenchone, 2-nonanone, 3-nonanone, 5-nonanone, 2-decanone, 2,5-hexanedione, phorone, 6-undecanone; aromatic ether solvents: 3-phenoxytoluene, butoxybenzene, benzylbutylbenzene, p-anisaldehyde dimethyl acetal, tetrahydro-2-phenoxy-2H-pyran, 1,2-dimethoxy-4-(1-propenyl)benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, pentyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether; and ester solvents: alkyl octoate, alkyl sebacate, alkyl stearate, alkyl benzoate, alkyl phenylacetate, alkyl cinnamate, alkyl oxalate, alkyl maleate, alkyl lactone, alkyl oleate, and the like.

Further, according to the ink of the present disclosure, the at least one solvent can be selected from: aliphatic ketones, such as 2-nonanone, 3-nonanone, 5-nonanone, 2-decanone, 2,5-hexanedione, 2,6,8-trimethyl-4-nonanone, phorone, 6-undecanone, and the like, or aliphatic ethers, such as pentyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether, and the like.

In other embodiments, the printing ink further comprises another organic solvent. Examples of another organic solvent comprise, but not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin, indene, and/or mixtures thereof.

In an embodiment, the formulation according to the present disclosure is a solution.

In another embodiment, the formulation according to the present disclosure is a suspension.

The present disclosure also relates to the use of the formulation as printing ink during the preparation of organic electronic devices, particularly by the preparation method of printing or coating.

Suitable printing or coating techniques include, but are not limited to, inkjet printing, nozzle printing, letterpress printing, screen printing, dip coating, spin coating, blade coating, roller printing, torsion roll printing, lithography, flexography, rotary printing, spraying, brushing or pad printing, nozzle printing, slot die coating, etc, preferably inkjet printing, slot die coating, nozzle printing and gravure printing.

The solution or suspension may additionally comprise one or more components such as surface-active compound, lubricant, wetting agent, dispersant, hydrophobic agent, binder, etc., for adjusting viscosity and film-forming performance, and enhancing adhesion, and the like. For more detailed information about printing technologies and relevant requirements thereof on related solutions, such as solvents and concentration, viscosity, etc., see Handbook of Print Media: Technologies and Production Methods, ISBN 3-540-67326-1, edited by Helmut Kipphan.

Based on the above compound, the present disclosure also provides an application of the compound or the polymer as described above in organic electronic devices. The organic electronic devices may be selected from, but not limited to, an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, an organic sensor, and an organic plasmon emitting diode, and the like, specially OLED. In an embodiment of the present disclosure, the organic compound is particularly used in the electron transport layer, electron injection layer or light-emitting layer of the OLED devices.

The present disclosure further relates to an organic electronic device comprising at least one of the compounds or the polymers as described above. Generally, such organic electronic device comprises at least one cathode, one anode, and one functional layer located between the cathode and the anode, wherein the functional layer comprises at least one of the compounds or the polymers as described above. The organic electronic devices may be selected from, but not limited to, an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, an organic sensor, and an organic plasmon emitting diode.

In a relatively embodiment, the organic electronic device is an electroluminescent device, in particular an OLED, comprising a substrate, an anode, a cathode, and at least one light-emitting layer located between the anode and the cathode, optionally may also comprise a hole transport layer or an electron transport layer. In an embodiment, the organic electronic device comprises an electron transport layer or an electron injection layer in which comprises the compound or the polymer according to the present disclosure. In another embodiment, the organic electronic device comprises a hole blocking layer in which comprises the compound or the polymer according to the present disclosure. In another embodiment, the organic electronic device comprises a light-emitting layer in which comprises the compound or the polymer according to the present disclosure, particularly, the light-emitting layer comprises the compound or the polymer according to the present disclosure and at least one light-emitting material which may be selected from fluorescent emitter, or TADF material.

The device structure of the electroluminescent device is described below, but it is not limited thereto.

The substrate can be opaque or transparent. A transparent substrate can be used to fabricate a transparent light-emitting device. See, e.g., Bulovic et al. Nature 1996, 380, p29 and Gu et al. ppl. Phys. Lett. 1996, 68, p2606. The substrate may be rigid or elastic. The substrate may be plastic, metal, semiconductor wafer or glass. In one embodiment, the substrate has a smooth surface. The substrate without any surface defects is a particularly desirable choice. In an embodiment, the substrate is flexible and may be selected from polymer thin film or plastic which have the glass transition temperature $T_g$ of greater than 150° C., further greater than 200° C., still further greater than 250° C., even further greater than 300° C. Suitable examples of the flexible substrate are poly(ethylene terephthalate) (PET) and polyethylene(2,6-naphthalate) (PEN).

The anode may comprise a conductive metal or a metal oxide, or a conductive polymer. The anode can inject holes easily into the hole injection layer (HIL), or the hole transport layer (HTL), or the light-emitting layer. In one embodiment, the absolute value of the difference between the work function of the anode and the HOMO energy level or the valence band energy level of the emitter in the light-emitting layer or of the p-type semiconductor material as the HIL or HTL or the electron blocking layer (EBL) is less than 0.5 eV, further less than 0.3 eV, even further less than 0.2 eV Examples of anode materials include, but not limited to, Al, Cu, Au, Ag, Mg, Fe, Co, Ni, Mn, Pd, Pt, ITO, aluminum doped zinc oxide (AZO), and the like. Other suitable anode materials are known and may be easily selected by one of ordinary skill in the art. The anode material may be deposited using any suitable technique, such as a suitable physical vapor deposition method, including radio frequency magnetron sputtering, vacuum thermal evaporation, e-beam, and the like. In some embodiments, the anode is patterned. Patterned ITO conductive substrates are commercially available and can be used to prepare the device according to the present disclosure.

The cathode may comprise a conductive metal or a metal oxide. The cathode can inject electrons easily into the EIL or ETL, or directly injected into the light-emitting layer. In one embodiment, the absolute value of the difference between the work function of the cathode and the LUMO energy level or the conduction band energy level of the emitter in the light-emitting layer or of the n type semiconductor material as the electron injection layer (EIL) or the electron transport layer (ETL) or the hole blocking layer (HBL) is less than 0.5 eV, further less than 0.3 eV, still further less than 0.2 eV. In principle, all materials that can be used as cathodes for OLED can be used as cathode materials for the devices of the present disclosure. Examples of the cathode materials include, but not limited to: Al, Au, Ag, Ca, Ba, Mg, LiF/Al, MgAg alloy, $BaF_2$/Al, Cu, Fe, Co, Ni, Mn, Pd, Pt, ITO, and the like. The cathode material may be deposited using any suitable technique, such as a suitable physical vapor deposition method, including radio frequency magnetron sputtering, vacuum thermal evaporation, e-beam, and the like.

OLED can also comprise other functional layers such as a hole injection layer (HIL), a hole transport layer (HTL), an electron blocking layer (EBL), an electron injection layer (EIL), an electron transport layer (ETL), and a hole blocking layer (HBL). Materials suitable for use in these functional layers are well known to those skilled in the art and are readily found in the literatures.

In an embodiment, in the light-emitting device according to the present disclosure, the electron transport layer or the electron injection layer thereof comprises the organic compound or the polymer of the present disclosure.

In another embodiment, the light-emitting device according to the present disclosure comprises a hole blocking layer in which comprises a compound or a polymer according to the present disclosure.

In another embodiment, in the light-emitting device according to the present disclosure, the light-emitting layer thereof comprises the organic compound or the polymer of the present disclosure.

According to the light-emitting device of the present disclosure, the light-emitting wavelength thereof is between 300 and 1000 nm, further between 350 and 900 nm, and still further between 400 and 800 nm.

The present disclosure also relates to the application of the organic electronic device according to the present disclosure in various electronic equipments, comprising, but not limited to display equipment, lighting equipment, light source, sensor, and the like.

The present disclosure will be described below with reference to the preferred embodiments, but the present disclosure is not limited to the following embodiments. It should be understood that the appended claims summarize the scope of the present disclosure. Those skilled in the art should realize that certain changes to the embodiments of the present disclosure that are made under the guidance of the concept of the present disclosure will be covered by the spirit and scope of the claims of the present disclosure.

Detailed Examples

1. Examples are given according to the method of synthesizing the compound of the present disclosure, but the present disclosure is not limited to the following examples.

Example 1: Synthesis of 1,6-bis(4-phenyl-6-(pyridine-3)-1,3,5-triazine-2-)pyrene (1)

Example 2: Synthesis of 1,6-bis(4,6-bis(pyridine-3)-1,3,5-triazine-2-)pyrene (2)

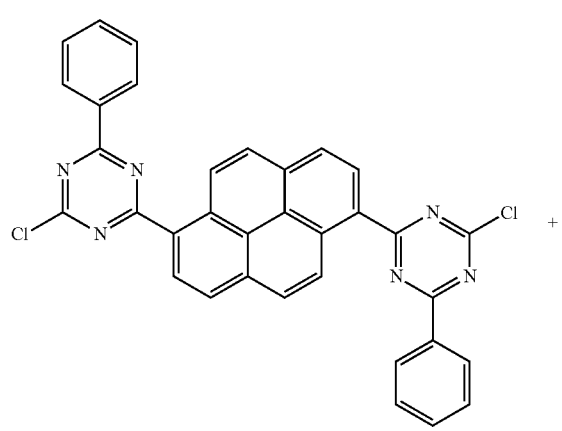

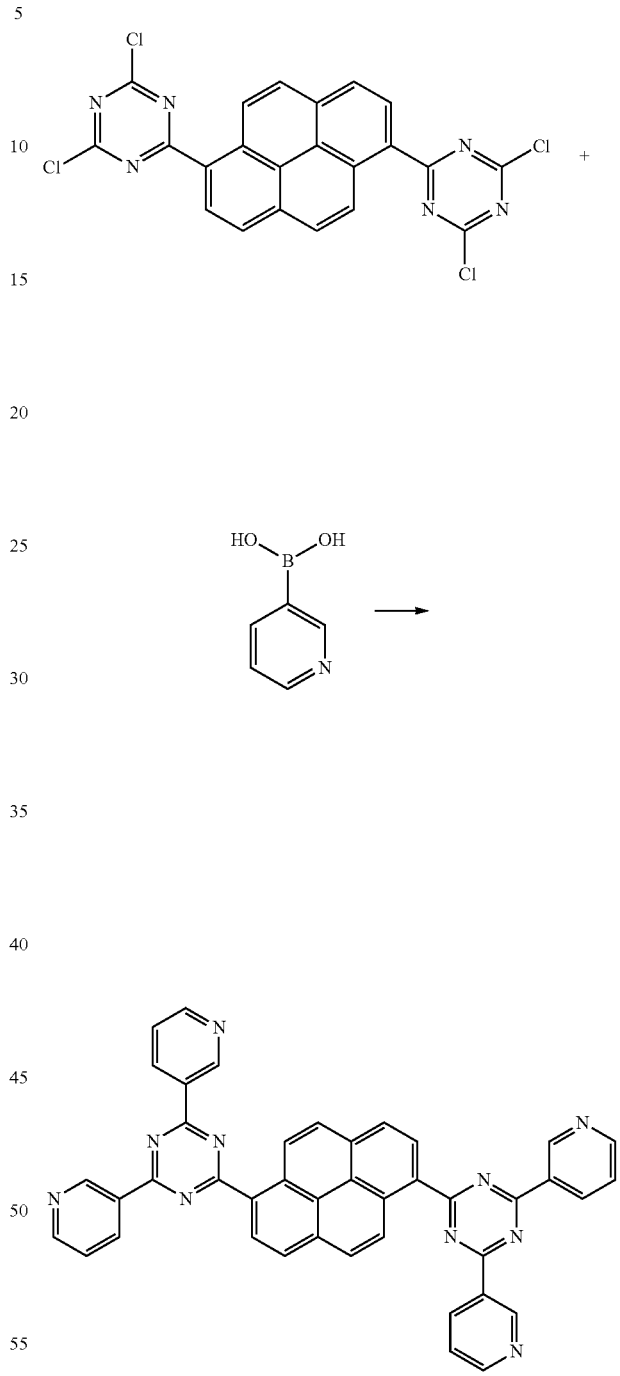

To a 1 L three-necked flask, 1,6-bis(4,6-dichloro-1,3,5-triazine-2-)pyrene (29 g, 0.05 mol), potassium carbonate (27.8 g, 0.2 mol), 3-pyridinyl boronic acid (12.3 g, 0.1 mol), Pd(PPh$_3$)$_4$ (2.89 g, 0.0025 mol), 500 mL of 1, 4-dioxane and 100 mL of water were added under the protection of nitrogen. The solution was heated to 120° C., reacted for 12 hours, cooled, extracted, dried, concentrated, and purified to give 1,6-bis(4-phenyl-6-(pyridine-3)-1,3,5-triazine-2-)pyrene with the yield of 73%.

To a 1 L three-necked flask, 1,6-bis(4,6-dichloro-1,3,5-triazine-2-)pyrene (25 g, 0.05 mol), potassium carbonate (27.8 g, 0.2 mol), 3-pyridinyl boronic acid (24.6 g, 0.2 mol), Pd(PPh$_3$)$_4$ (2.89 g, 0.0025 mol), 500 mL of 1, 4-dioxane and 100 mL of water were added under the protection of nitrogen. The solution was heated to 120° C., reacted for 12 hours, cooled, extracted, dried, concentrated, and purified to give 1,6-bis(4,6-bis(pyridine-3)-1,3,5-triazine-2-)pyrene with the yield of 75%.

Example 3: Synthesis of 1,6-bis(4-phenyl-6-(quinolin-6)-1,3,5-triazine-2-)pyrene (3)

Example 4: Synthesis of 1,6-bis(4,6-bis(quinolin-6)-1,3,5-triazine-2-)pyrene (4)

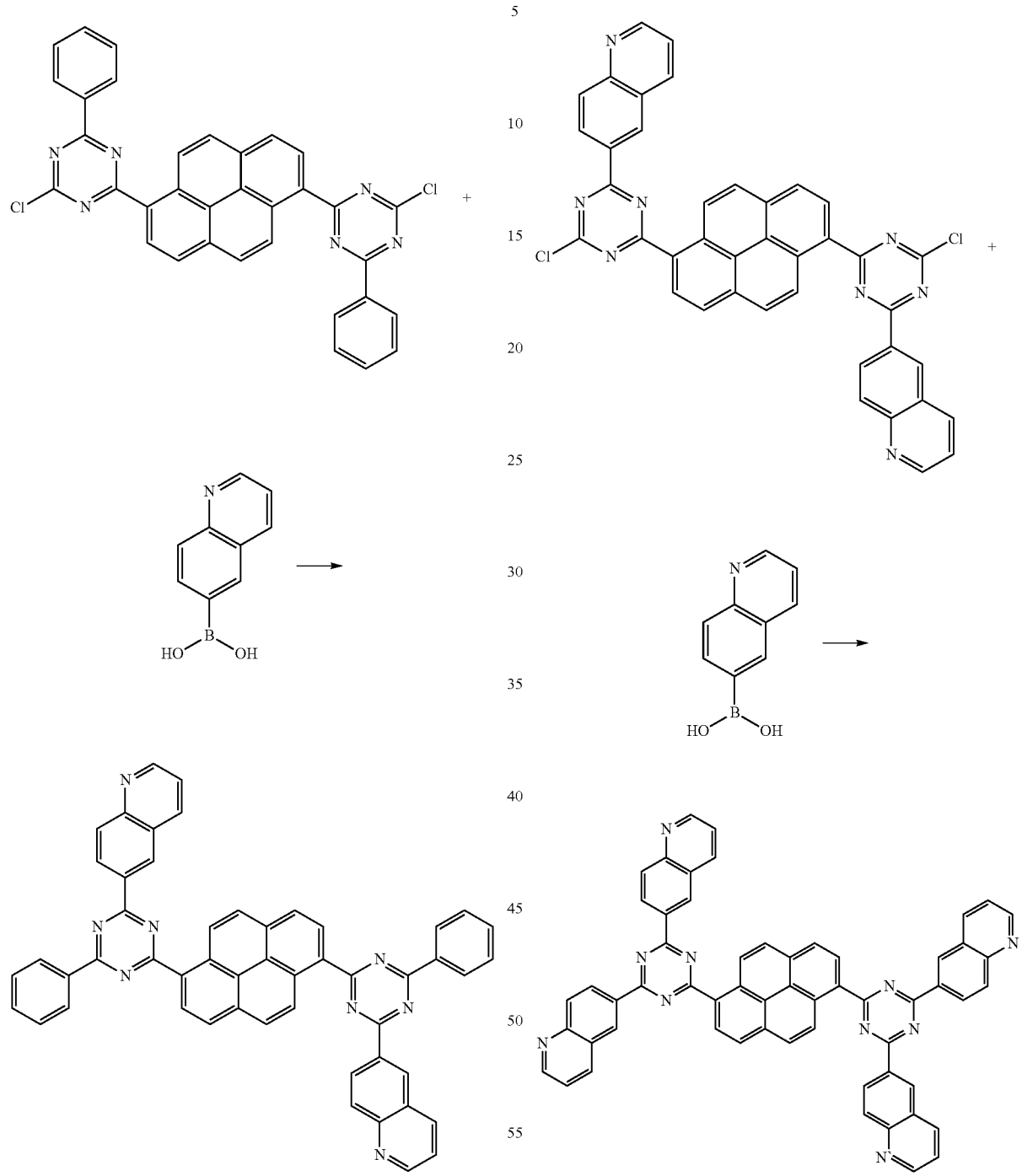

To a 1 L three-necked flask, 1,6-bis(4-chloro-6-phenyl-1,3,5-triazine-2-)pyrene (29.05 g, 0.05 mol), quinoline-6-boronic acid (17.3 g, 0.1 mol), potassium carbonate (27.8 g, 0.2 mol), Pd(PPh$_3$)$_4$ (2.89 g, 0.0025 mol), 500 mL of 1, 4-dioxane and 100 mL of water were added under the protection of nitrogen. The solution was heated to 120° C., reacted for 12 hours, cooled, extracted, dried, concentrated, and purified to give 1,6-bis(4-phenyl-6-(quinolin-6)-1,3,5-triazine-2-)pyrene with the yield of 80%.

To a 1 L three-necked flask, 1,6-bis(4-chloro-6-(quinolin-6-)-1,3,5-triazine-2)pyrene (34 g, 0.05 mol), quinoline-6-boronic acid (17.3 g, 0.1 mol), potassium carbonate (27.8 g, 0.2 mol), Pd(PPh$_3$)$_4$ (2.89 g, 0.0025 mol), 500 mL of 1, 4-dioxane and 100 mL of water were added under the protection of nitrogen. The solution was heated to 120° C., reacted for 12 hours, cooled, extracted, dried, concentrated, and purified to give 1,6-bis(4,6-bis(quinolin-6)-1,3,5-triazine-2-)pyrene with the yield of 70%.

Example 5: Synthesis of 1,6-bis(4-phenyl-6-(4-(pyridine-3-)phenyl)-1,3,5-triazine-2-)pyrene

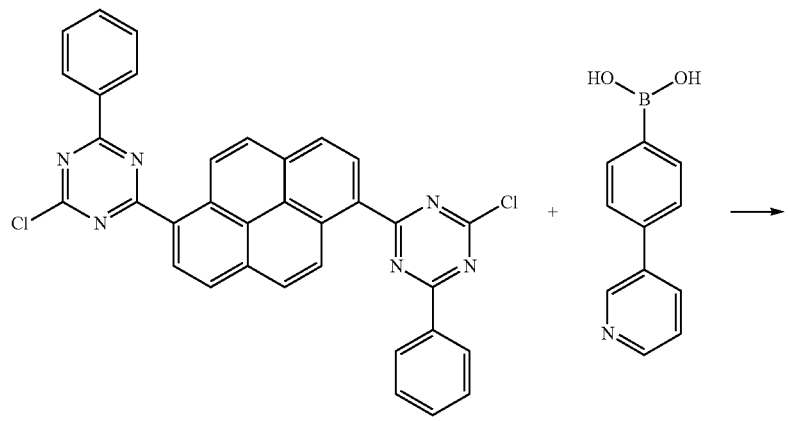

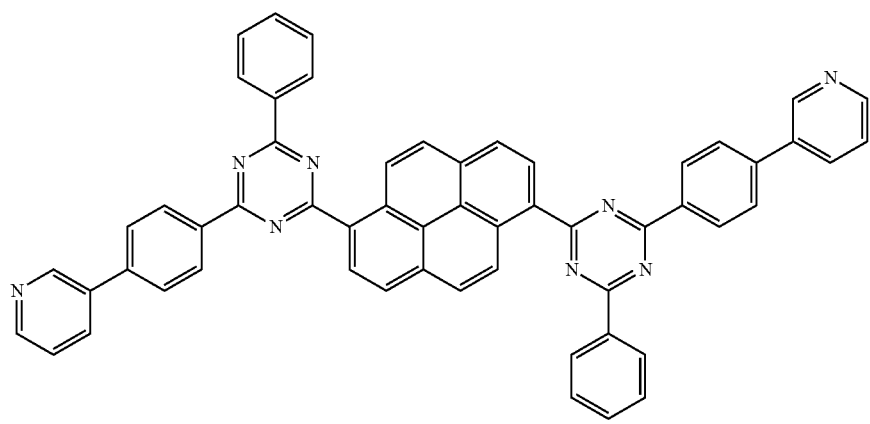

To a 1 L three-necked flask, 1,6-bis(4-chloro-6-phenyl-1,3,5-triazine-2)pyrene (29.0 g, 0.05 mol), 4-(3-pyridyl)phenyl boronic acid (20.0 g, 0.1 mol), potassium carbonate (27.8 g, 0.2 mol), Pd(PPh$_3$)$_4$ (2.89 g, 0.0025 mol), 500 mL of 1, 4-dioxane and 100 mL of water were added under the protection of nitrogen. The solution was heated to 120° C., reacted for 12 hours, cooled, extracted, dried, concentrated, and purified to give 1,6-bis(4-phenyl-6-(4-(pyridine-3-)phenyl)-1,3,5-triazine-2-)pyrene with the yield of 79%.

Example 6: Synthesis of 1,6-bis(4,6-bis(4-(pyridyl-3-)phenyl)-1,3,5-triazine-2-)pyrene (6)

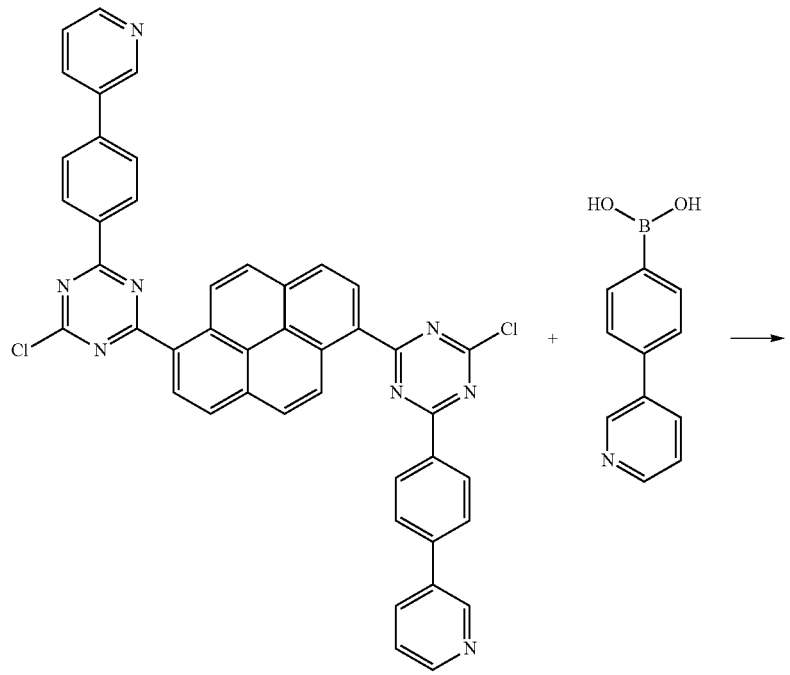

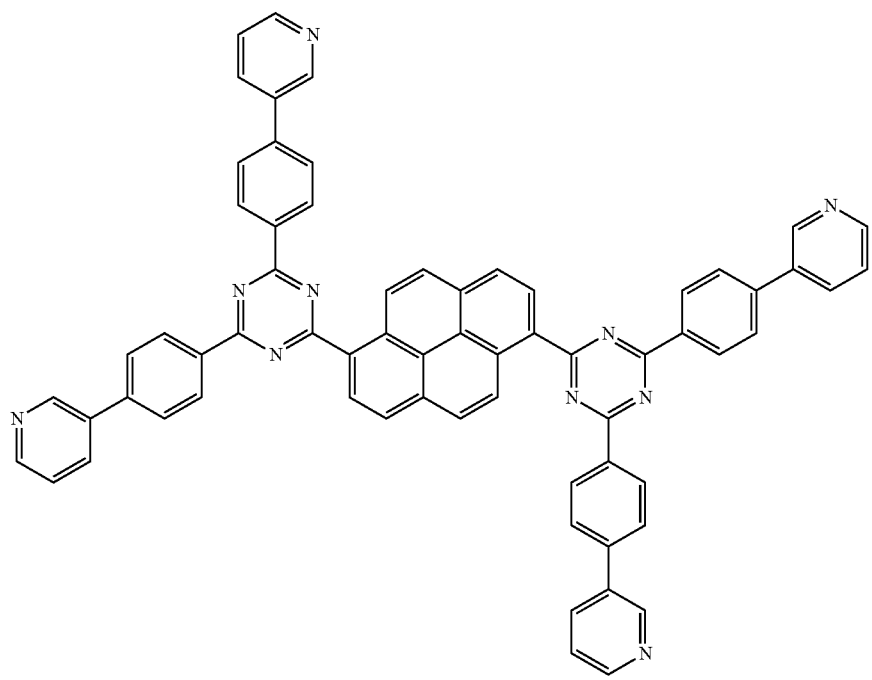

To a 1 μL three-necked flask, 1,6-bis(4-chloro-6-(4-(pyridine-3-)phenyl)-1,3,5-triazine-2-)pyrene (36.78 g, 0.05 mol), 4-(3-pyridyl)phenyl boronic acid (20.0 g, 0.1 mol), potassium carbonate (27.8 g, 0.2 mol), Pd(PPh$_3$)$_4$ (2.89 g, 0.0025 mol), 500 mL of 1, 4-dioxane and 100 mL of water were added under the protection of nitrogen The solution was heated to 120° C., reacted for 12 hours, cooled, extracted, dried, concentrated, and purified to give 1,6-bis (4,6-bis(4-(pyridyl-3-)phenyl)-1,3,5-triazine-2-)pyrene with the yield of 75%.

Comparative Example 1: Synthesis of the Comparative Compound 2-(4-(9,10-bis(2-naphthalene)anthracene-2-)phenyl)-1-phenyl-1-H-benzimidazole (comparative 1)

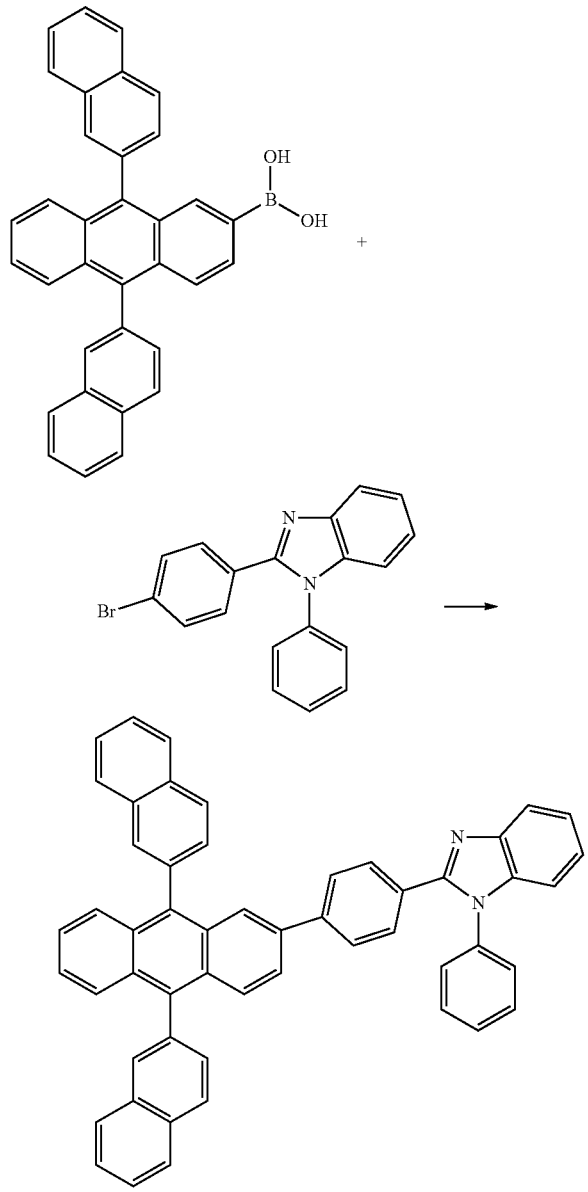

To a 1 L double-necked round-bottom flask, 9,10-bis(2-naphthalene)anthracene-2-boronic acid (47.4 g, 0.1 mol), and 2-(4-bromobenzene)-1-phenyl-1-H-benzimidazole (34.9 g, 0.1 mol) were added, followed by 500 mL of toluene as a solvent. The equipment was installed. Potassium carbonate (20.7 g, 0.15 mol) was completely dissolved in 100 mL of water, the solution was added into the round-bottom flask, and finally Pd(PPh$_3$)$_4$ (3.4 g, 0.003 mol) was put into the flask. Air in the flask was evacuated by an oil pump, and nitrogen gas was introduced thereto. The mixture was heated at constant temperature under reflux for 12 hours, and then cooled. The reaction solution was transferred to a rotary evaporator flask and evaporated most of the solvent away by rotary evaporation, extracted with dichloromethane, washed three times with water, dried over anhydrous magnesium sulfate, filtered, spin-dried, then purified to give 2-(4-(9,10-dis(2-naphthalene) anthracene-2-)phenyl)-1-phenyl-1-H-benzimidazole, with the yield of 74%.

Energy Structure of Organic Compounds

The energy levels of organic materials can be obtained by quantum calculations, such as using TD-DFT (Time Dependent-Density Functional Theory) by Gaussian03W (Gaussian Inc.), and the specific simulation methods can be found in WO2011141110. Firstly, the molecular geometry is optimized by semi-empirical method "Ground State/Semi-empirical/Default Spin/AM1" (Charge 0/Spin Singlet), and then the energy structure of organic molecules is calculated by TD-DFT (time-density functional theory) for "TD-SCF/DFT/Default Spin/B3PW91" and the basis set "6-31G (d)" (Charge 0/Spin Singlet). The HOMO and LUMO levels are calculated according to the following calibration formulas, and S1 and T1 are used directly.

HOMO(eV)=((HOMO(G)×27.212)−0.9899)/1.1206

LUMO(eV)=((LUMO(G)×27.212)−2.0041)/1.385 wherein HOMO(G) and LUMO(G) in the unit of Hartree are the direct calculation results of Gaussian 03W. The results were shown in Table 1:

TABLE 1

| | HOMO [eV] | ΔHOMO [eV] | LUMO [eV] | T1 [eV] | S1 [eV] |
|---|---|---|---|---|---|
| Example 1 | −5.93 | 0.79 | −3.04 | 2.04 | 3.01 |
| Example 2 | −6.02 | 0.79 | −3.17 | 2.04 | 2.92 |
| Example 3 | −5.91 | 0.78 | −3.00 | 2.04 | 3.02 |
| Example 4 | −5.99 | 0.77 | −3.12 | 2.04 | 2.68 |
| Example 5 | −5.91 | 0.76 | −3.01 | 2.04 | 3.07 |
| Example 6 | −5.96 | 0.74 | −3.07 | 2.04 | 2.96 |
| Comparative Example 1 | −5.56 | 0.53 | −2.83 | 1.66 | 2.83 |

2. Preparation and Characterization of OLED Devices:
HIL: a triarylamine derivative;
HTL: a triarylamine derivative;
Host: anthracene derivative;
Dopant: a triarylamine derivative;
ETL: Compound 1—Compound 6, Comparative Compound 1.

The preparation steps of an OLED device having ITO/HIL (50 nm)/HTL (35 nm)/Host: 5% Dopant (25 nm)/ETL (28 nm)/LiQ (1 nm)/Al (150 nm)/cathode are as follows:

a. cleaning of conductive glass substrate: when the conductive glass substrate is used for the first time, various solvents such as chloroform, ketone, and isopropanol can be used for cleaning, then treating with UV and ozone plasma;

b. HIL (50 nm), HTL (35 nm), EML(25 nm), ETL (28 nm): formed by thermal evaporation in high vacuum (1×10$^{-6}$ mbar).

c. cathode: LiQ/Al (1 nm/150 nm) was formed by thermal evaporation in high vacuum (1×10$^{-6}$ mbar);

d. encapsulation: the device was encapsulated with ultraviolet curable resin in a nitrogen glove box.

The current-voltage (J-V) characteristics of each OLED device were characterized by characterization equipment while important parameters such as efficiency, lifetime and external quantum efficiency were recorded. After testing, the blue light-emitting device prepared by using the compound 1 to compound 6 as the electron transfer layer ETL has a better color coordinate than that prepared by using the comparative compound 1. For example, the device prepared by using the compound 1 to compound 6 has a color coordinate with X<0.15 and Y<0.10. In addition, the blue light-emitting device prepared by using the compound 1 to compound 6 as the ETL layer has luminous efficiency in the range of 5-8 cd/A, which is more excellent luminous efficiency; in terms of lifetime of the device, the blue light-emitting device prepared by using the compound 1 to compound 6 as the ETL layer has a much better lifetime than that prepared by using the comparative compound 1. For example, the $T_{95}$ lifetime of the device prepared by using the compound 1 to compound 6 is at least twice that prepared by using the comparative compound 1 at 1000 nits. The test results are shown in table 2.

TABLE 2

| | Efficiency (cd/A) | Lifetime (T95, 1000 nits) relative to the comparative example 1 | Color coordinate (CIE, 1931) |
| --- | --- | --- | --- |
| Example 1 | 4.3 | 2.24 | (0.14, 0.08) |
| Example 2 | 4.5 | 2.41 | (0.14, 0.09) |
| Example 3 | 5.1 | 3.13 | (0.12, 0.08) |
| Example 4 | 4.7 | 3.11 | (0.12, 0.09) |
| Example 5 | 5.8 | 3.25 | (0.13, 0.08) |
| Example 6 | 6.1 | 3.41 | (0.12, 0.08) |
| Comparative Example 1 | 3.6 | 1 | (0.18, 0.15) |

In the present disclosure, a triazine structure containing three strong electron-accepting nitrogen atoms is linked to a planar pyrene aromatic fused ring, achieving better carrier transport performance and photoelectric response, and thus achieving higher efficiency, longer lifetime and bluer color coordinates due to the large planar conjugated structure of the molecule.

The technical features of the above-described embodiments may be combined arbitrarily. To simplify the description, not all of the possible combinations of the technical features in the above embodiments are described. However, all of the combinations of these technical features should be considered as within the scope of the present disclosure, as long as such combinations do not contradict with each other.

The above-described embodiments merely represent several embodiments of the present disclosure, and the description thereof is more specific and detailed, but it should not be construed as limiting the scope of the present disclosure. It should be noted that, for those skilled in the art, several variations and improvements may be made without departing from the concept of the present disclosure, and these are all within the protection scope of the present disclosure. Therefore, the scope of the present disclosure shall be defined by the appended claims.

What is claimed is:

1. A pyrene-triazine compound represented by general formula (1):

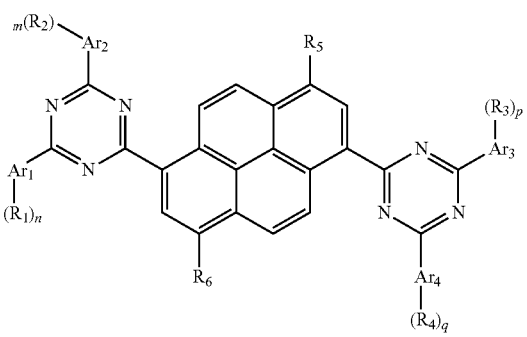

wherein

Ar$_1$ and Ar$_3$ each is a heterocyclic aromatic group having a nitrogen atom selected from the following structures:

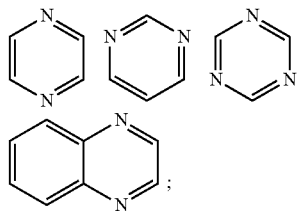

Ar$_2$ and Ar$_4$ are selected from the following structures:

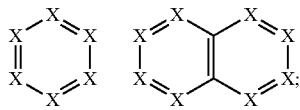

X is CR$_{13}$ or N, but two adjacent X are not simultaneously N; R$_1$ to R$_7$ and R$_{13}$ are selected from group consisting of H, D, F, —CN, —NO$_2$, —CF$_3$, alkenyl, alkynyl, amino, acyl, amide group, cyano, isocyano, alkoxy, hydroxy, carbonyl, sulfonyl, an alkyl group containing 1 to 60 carbon atoms, a cycloalkyl group containing 3 to 60 carbon atoms, an aromatic group containing 6 to 60 carbon atoms, and a heterocyclic aromatic group containing 3 to 60 carbon atoms; and m, n, p, and q are integers from 0 to 20.

2. A mixture comprising the pyrene-triazine compound of claim 1, and at least one organic solvent or at least one organic functional material, which is selected from a hole injection material, a hole transport material, a hole blocking material, an electron injection material, an electron transport material, an electron blocking material, a light-emitting host material, a fluorescent emitter, a phosphorescent emitter, a thermally activated delayed fluorescent material or an organic dye.

3. An organic electronic device comprising the pyrene-triazine compound of claim 1.

4. The organic electronic device according to claim 3, wherein the organic electronic device is an organic light emitting diode, an organic photovoltaic cell, an organic light-emitting electrochemical cell, an organic field effect transistor, an organic light emitting field effect transistor, an organic laser, an organic spintronic device, an organic sensor or an organic plasmon emitting diode.

5. The organic electronic device according to claim 3, wherein the organic electronic device is an organic electroluminescence device, and the organic electronic device comprises an electron transport layer, an electron injection layer or a light-emitting layer, the electron transport layer, the electron injection layer or the light-emitting layer comprising the pyrene-triazine compound.

6. The pyrene-triazine compound according to claim 1, wherein the lowest unoccupied molecular orbital energy level (LUMO) is less than or equal to −3.05 eV.

7. The pyrene-triazine compound according to claim 1, wherein the highest occupied molecular orbital energy level (HOMO) is less than or equal to −6.0 eV.

8. The pyrene-triazine compound according to claim 1, wherein the triplet excited state energy level (T1) is greater than or equal to 1.8 eV.

9. The pyrene-triazine compound according to claim 1, wherein the ΔHOMO is greater than or equal to 0.5 eV, ΔHOMO=|(HOMO−1)−HOMO|, (HOMO−1) represents the second highest occupied molecular orbital energy level, HOMO represents the highest occupied molecular orbital energy level.

* * * * *